US008354378B2

(12) United States Patent
Kuliopulos et al.

(10) Patent No.: US 8,354,378 B2
(45) Date of Patent: *Jan. 15, 2013

(54) G PROTEIN COUPLED RECEPTOR ANTAGONISTS AND METHODS OF ACTIVATING AND INHIBITING G PROTEIN COUPLED RECEPTORS USING THE SAME

(75) Inventors: Athan Kuliopulos, Winchester, MA (US); Lidija Covic, Somerville, MA (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/394,715

(22) Filed: Feb. 27, 2009

(65) Prior Publication Data

US 2009/0270322 A1    Oct. 29, 2009

Related U.S. Application Data

(63) Continuation of application No. 10/251,703, filed on Sep. 20, 2002, now Pat. No. 7,696,168, which is a continuation-in-part of application No. 09/841,091, filed on Apr. 23, 2001, now Pat. No. 6,864,229.

(60) Provisional application No. 60/198,993, filed on Apr. 21, 2000.

(51) Int. Cl.
*A61K 38/17* (2006.01)
*A61K 38/04* (2006.01)
*C07K 14/705* (2006.01)
*C12P 21/04* (2006.01)

(52) U.S. Cl. ...... 514/20.6; 435/69.7; 530/300; 530/402; 514/16.4

(58) Field of Classification Search .................. None
See application file for complete search history.

(56) References Cited

U.S. PATENT DOCUMENTS

| | | | |
|---|---|---|---|
| 5,508,384 A | 4/1996 | Murphy et al. |
| 5,747,267 A | 5/1998 | Mulvihill et al. |
| 5,750,370 A | 5/1998 | Li et al. |
| 5,925,549 A | 7/1999 | Hsueh et al. |
| 5,935,936 A | 8/1999 | Fasbender et al. |
| 6,096,868 A | 8/2000 | Halsey et al. |
| 6,111,075 A | 8/2000 | Xu et al. |
| 6,111,076 A | 8/2000 | Fukusumi et al. |
| 6,162,808 A | 12/2000 | Kindon et al. |
| 6,548,499 B1 | 4/2003 | Carson |
| 6,864,229 B2 | 3/2005 | Kuliopulos et al. |
| 7,304,127 B2 | 12/2007 | Saxinger |
| 2003/0148449 A1 | 8/2003 | Kuliopulos et al. |
| 2006/0166274 A1 | 7/2006 | Kuliopulos et al. |
| 2007/0179090 A1 | 8/2007 | Kuliopulos et al. |
| 2008/0234183 A1 | 9/2008 | Hallbrink et al. |

FOREIGN PATENT DOCUMENTS

| | | |
|---|---|---|
| AU | 7201010 | 3/2007 |
| AU | 1257169 | 5/2007 |
| CA | 2406839 A1 | 11/2001 |
| EP | 1278777 A2 | 1/2003 |
| JP | 2003530875 | 10/2003 |
| WO | WO-9800538 A2 | 1/1998 |
| WO | WO-9834948 A1 | 8/1998 |
| WO | WO-9943711 A1 | 9/1999 |
| WO | WO-9962494 A2 | 12/1999 |
| WO | WO-0181408 A2 | 11/2001 |
| WO | WO2006052723 A2 | 5/2006 |

OTHER PUBLICATIONS

Anand-Srivastava et al., *J. Biol. Chem.*, 271:19324-19329 (1996).
Andrade-Gordon, et al., "Design, Synthesis, and Biological Characterization of a Peptide-Mimetic Antagonist for a Tethered-Ligand Receptor", *Proc. Natl. Acad. Sci. U.S.A.*, 96(22J:12257-12262 (1999).
Aoki et al., "A novel human G-protein-coupled receptor, EDG7, for lysophosphatidic acid with unsaturated fatty-acid moiety", *Annals of the New York Academy of Sciences: Lysophospholipids and Eicosanoids in Biology and Pathophysiologi*, pp. 263-266 (2000).
Bernatowicz et al., "Development of Potent Thrombin Receptor Antagonist Peptides", *J. Med. Chem.*, 39:4879-4887 (1996).
Cotecchia et al., "Discrete Amino Acid Sequences of the .alpha.1-Adrenergic Receptor Determine the Selectivity of Coupling to Phosphatidylinositol Hydrolysis", *J Biol. Chem.*, 267:1633-1639 (1992).
Coughlin, et al, 2003, *J. Clin. Invest.*, 111(1): 25-27.
Covic et al., "Activation and inhibition of G protein-coupled receptors by cell-penetrating membrane-tethered peptides", *Proc. Natl. Acad. Sci. U.S.A.*, 99(2): 643-648 (2002).
Covic et al., "Intracellular liganding of the PAR1 thrombin receptor by a novel class of cell penetrating peptides", *Blood*, 96(11): 244a. Abstract #1050 (2000).
Covic, L., Gresser, A. L., Kuliopulos, A., "Biphasic Kinetics of Activation and Signaling for PAR1 and PAR4 Thrombin Receptors in Platelets", *Biochemistry*, 39:5458-5467 (2000).
Dalman, et al., *J. Biol. Chem.*, 266:11025-11029 (1991).
Elliot et al., "Maleimide-Functionalized Lipids that Anchor Polypeptides to Lipid Bilayers and Membranes", *Bioconjugate Chem.*, 11(6):832-841 (2000).
Faruqi et al., "Structure-Function Analysis of Protease-activated Receptor 4 Tethered Ligand Peptides", *J. Biol. Chem.*, 275(26):19728-19734 (2000).
George et al., "A Transmembrane Domain-Derived Peptide Inhibits D1 Dopamine Receptor Function without Affecting Receptor Oligomerization", *J. Biol. Chem.*, 273(46):30244-30248 (1998).
Gether et al., "G Protein-coupled Receptors", *J. Biol. Chem.*, 273:17979-17982. (1998).
Gilman, A. G., "G Proteins: Transducers of Receptor-Generated Signals", *Ann. Rev. Biochem.*, 56:615-649 (1987).

(Continued)

*Primary Examiner* — Marianne P Allen
(74) *Attorney, Agent, or Firm* — McDermott Will & Emery LLP

(57) ABSTRACT

The invention relates generally to G protein coupled receptors and in particular to agonists and antagonists of G protein receptors and methods of using the same.

30 Claims, 28 Drawing Sheets

OTHER PUBLICATIONS

Hammes et al., "Protease-Activated Receptor-1 Can Mediate Responses to SFLLRN in Thrombin-Desensitized Cells: Evidence for a Novel Mechanism for Preventing or Terminating Signaling by PAR1's Tethered Ligand", *Biochem.*, 38: 2486-2493 (1999).

Higashijima et al., "Mastoparan, a Peptide Toxin from Wasp Venom, Mimics Receptors by H Activating GTP-binding Regulatory Proteins (G Proteins)", *J Biol. Chem.*, 263:6491-6494 (1988).

Ishii et al., *J. Biol. Chem.*, 269:1125-1130 (1994).

Ishii, et al., "Determinants of Thrombin Receptor Cleavage", J. Biol. Chem., 270(27):16435-16440 (1995).

Kahn et al., "A Dual Thrombin Receptor System for Platelet Activation", *Nature*, 394:690-694 (1998).

Kjelsberg et al., "Constiutive Activator of the .alpha..sub.1B-Adrenergic Receptor by Acid Substitutions at a Single Site", *J. Biol. Chem.*, 267:1430-1433 (1992).

Kostenis et al., "Molecular Basis of Receptor/G Protein Coupling Sensitivity Studies by Coexpression of Wild Type and Mutant m2 Muscarinic Receptors with Mutant G.alpha..sub.q Subunits", *Biochem.*, 36:1487-1495 (1997).

Kuliopulos et al., "Plasmin Desensitization of the PAR1 Thrombin Receptor: Kinetics, Sites of Truncation, and Implications for Thrombolytic Therapy", *Biochem.*, 38:4572-4585 (1999).

Luttrell et al., "Antagonism of Catecholamine Receptor Signaling by Expression of Cytoplasmic Domains of the Receptors", *Science*, 259:1453-1457 (1993).

Megaritis et al., "Functional Domains of δ- and —µ-Opioid Receptors Responsible for Adenylyl Cyclase Inhibition", *Receptors and Channels*, 7:199-212.

Merkouris et al., "Identification of the Critical Domains of the δ-Opioid Receptor Involved in G Protein Coupling Using Site-Specific Synthetic Peptides", *Mol. Pharmacol.*, 50:985-993 (1996).

Milligan, G., "Receptors as Kissing Cousins", *Science*, 288:65-67 (2000).

Moro et al., "Hydrophobic Amino Acid in the i2 Loop Plays a Key Role in Receptor-G Protein Coupling", *J. Biol. Chem..*, 268(30): 22273-22276 (1993).

Nystedt et al., "Molecular Cloning of a Potential Proteinase Activated Receptor", *Proc. Natl. Acad. Sci. U.S.A.*, 91:9208-9212 (1994).

Okamoto et al., "Identification of a G.sub.S Activator Region of the .beta.2-Adrenergic Receptor That is Autoregulated via Protein Kinase A-Dependent Phosphorylation", *Cell*, 67:723-730 (1991).

Oosterom et al., "Common Structure for Melanocortin-4 Receptor Selectivity of Structurally Unrelated MelanocortinAgonist and Endogenous Antagonist, Agouti Protein", *J. Biol. Chem.*, 276:931-936 (2001).

Palczewski et al., "Crystal Structure of Rhodopsin: A G Protein-Coupled Receptor", *Science*, 289:739-745 (2000).

Pfeiffer et al., "Homo- and Heterodimerization of Somatostatin Receptor Subtypes", *J. Biol. Chem.*, 276:14027-14036 (2001).

Rojas et al., "Genetic Engineering of Proteins with Cell Membrane Permeability", *Nature Biotech.*, 16:370-375 (1998).

Schwarze et al., "In Vivo Protein Transduction: Delivery of a Biologically Active Protein into the Mouse", *Science*, 285:1569-1572 (1999).

Stephens et al., "A Sequence within the Cytoplasmic Tail of GpIIb Independently Activates Platlet Aggregation and Thromboxane Synthesis", *J. Biol. Chem.*, 273:20317-20322 (1998).

Swift et al., "PAR1 Thrombin Receptor-G Protein Interactions", *J. Biol. Chem.*, 275(4):2627-2635 (2000).

Tarasova, N., "Inhibition of G-Protein-coupled Receptor Function by Disruption of Transmembrane Domain Interactions", *J. Biol. Chem.*, 274:34911-34915 (1999).

Trejo et al., "The Cytoplasmic Tails of Protease-activated Receptor-1 and Substance P Receptor Specify Sorting to Lysosomes versus Recycling", *J. Biol. Chem.*, 274(4):2216-2224 (1999).

Vergnolle et al., "Protease-Activated Receptors in Inflammation, Neuronal Signaling and Pain", *Trends Pharma. Sci.*, 22:146-152.

Wikstrom et al., "The Properties of Peptidyl Diazoethanes and Chloroethanes as Protease Inactivators", *Arch. Biochem. Biophysics*, 270:286-293 (1989).

Xu et al., "Cloning and Characterization of Human Protease-Activated Receptor 4", *Proc. Natl. Acad. Sci. U.S.A.*, 95:6642-6646 (1998).

Arora et al., "Mediation of Cyclic AMP Signaling by the First Intracellular Loop of the Gonadotropin-releasing Hormone Receptor," The Journal of Biological Chemistry, 273:25581-25586 (1998).

Ballesteros et al., "Integrated Methods for the Construction of Three-Dimensional Models and Computational Probing of Structure-Function Relations in G Protein-Coupled Receptors," Methods in Neurosciences, 25:366-428 (1995).

Bommakanti et al., "Extensive Contact between $G_{i2}$ and N-Formyl Peptide Receptor of Human Neutrophils: Mapping of Binding Sites Using Receptor-Mimetic Peptides," Biochemistry, 34:6720-6728 (1995).

Gether, "Uncovering Molecular Mechanisms Involved in Activation of G Protein-Coupled Receptors," Endocrine Reviews, 21:90-113 (2000).

Kaneider et al., "Reversing systemic inflammatory response syndrome with chemokine receptor pepducins," Nat. Med., 11(6):661-665 (2005).

Keane et al., "Depletion of CXCR2 inhibits tumor growth and angiogenesis in a murine model of lung cancer," J. Immunol., 172(5):2853-2860 (2004).

Kuliopulos et al., "Blocking receptors on the inside: pepducin-based intervention of PAR signaling and thromobosis", Life Sci., 74(2-3):255-262 (2003).

Leger et al., "Blocking the Protease-Activated Receptor 1-4 Heterodimer in Platelet-Mediated Thrombosis," Circulation, 113:1244-1254 (2006).

Mirzadegan et al., "Sequence Analyses of G-Protein-Coupled Receptors: Similarities to Rhodopsin," Biochemistry, 42:2759-2767 (2003).

Nussenzveig et al., "Inhibition of Inositol Phosphate Second Messenger Formation by Intracellular Loop One of a Human Calcitonin Receptor," The Journal of Biological Chemistry, 269:28123-28129 (1994).

Tarzami et al., "Opposing effects mediated by the chemokine receptor CXCR2 on myocardial ischemia-reperfusion injury: recruitment of potentially damaging neutrophils and direct myocardial protection", Circulation, 108(19):2387:2392 (2003).

Wank, "G Protein-Coupled Receptors in Gastrointestinal Physiology. CCK Receptors: An Exemplary Family," Am. J. Physiol. 274:G607-G613 (1998).

Wu et al., "First Intracellular Loop of the Human Cholecystokinin-A Receptor is Essential for Cyclic AMP Signaling in Transfected HEK-293 Cells," The Journal of Biological Chemistry, 272:9037-9042 (1997).

Chackalamannil, "Thrombin receptor antagonists as novel therapeutic targets," Current Opinion in Drug Discovery & Development, 4(4):417-427 (2001).

Patterson et al., "New Tricks for Old Dogs: Nonthrombotic Effects of Thrombin in Vessel Wall Biology," Circulation Research, 88:987-997 (2001).

Brass, "Platelets and proteases," Nature, 413:26-27 (2001).

Riewald, et al., "Orchestration of Coagulation Protease Signaling by Tissue Factor," Trends Cardiovascular Med., 12:149-154 (2002).

Aebischer et al., "Intrathecal Delivery of CNTF using Encapsulated Genetically Modified Xenogeneic Cells in Amyotrophic Lateral Sclerosis Patients," Nature Medicine, 2:696-699 (1996).

Agarwal et al., "Identification of a Metalloprotease-Chemokine Signaling System in the Ovarian Cancer Microenvironment: Implications for Antiangiogenic Therapy," Cancer Research, 70:5880-5890 (2010).

Agarwal et al., "Targeting a Metalloprotease-PAR1 Signaling System with Cell-Penetrating Pepducins Inhibits Angiogenesis, Ascites, and Progression of Ovarian Cancer," Mol. Cancer Ther. 7:2746-2757 (2008).

Appleyard et al., "Tyrosine Phosphorylation of the κ-Opioid Receptor Regulates Agonist Efficacy," The Journal of Biological Chemistry, 275:38281-38285 (2000).

Benovic et al., "Synthetic Peptides of the Hamster $β_2$-Adrenoceptor as Substrates and Inhibitors of the β-Adrenoceptor Kinase," Br. J. Clin. Pharmoc., 30:3S-125 (1990).

Boire et al., "PAR1 is a Matrix Metalloprotease-1 Receptor that Promotes Invasion and Tumorigenesis of Breast Cancer Cells," Cell, 120:303-313 (2005).

Calandra et al., "Dual Intracellular Signaling Pathways Mediated by the Human Cannabinoid $CB_1$ Receptor," European Journal of Pharmacology, 374:445-455 (1999).

Cassina et al., "Dual Intracellular Pathways in Gonadotropin Releasing Hormone (GNRH) Induced Desensitization of Luteinizing Hormone (LH) Secretion," Life Sciences, 64:2215-2223, (1999).

Cheung et al., "Specific Activation of $G_s$ by Synthetic Peptides Corresponding to an Intracellular Loop of the β-Adrenergic Receptor," FEBS Letters, 279:277-280 (1991).

Cummings, et al., "Expression and Function of the Chemokine Receptors CXCR1 and CXCR2 in Sepsis," J. Immunol., 162:2341-2346 (1999).

Cypess et al., "Two Cytoplasmic Loops of the Glucagon Receptor are Required to Elevate cAMP or Intracellular Calcium," The Journal of Biological Chemistry, 274:19455-19464 (1999).

Damaj et al., "Identification of G-Protein Binding Sites of the Human Interleukin-8 Receptors by Functional Mapping of the Intracellular Loops," FASEB J., 10:1426-1434 (1996).

DeAlmeida et al., "Identification of Binding Domains of the Growth Hormone-Releasing Hormone Receptor by Analysis of Mutant and Chimeric Receptor Proteins," Molecular Endocrinology, 12:750-765 (1998).

Eisenstein et al., "GPCRs: Insane in the Membrane," Nature Methods, 6:929-933 (2009).

Gaudin et al., "Constitutive Activation of the Human Vasoactive Intestinal Peptide 1 Receptor, a Member of the New Class II Family of G Protein-Coupled Receptors," The Journal of Biological Chemistry, 273:4990-4996 (1998).

Halford et al., "Functional Role and Sequence Analysis of a Lymphocyte Orphan Opioid Receptor," Journal of Neuroimmunology, 59:91-101 (1995).

Kai et al., "G-Protein Binding Domains of the Angiotensin II $AT_{1A}$ Receptors Mapped with Synthetic Peptides Selected from the Receptor Sequence," Biochem J., 332:781-787 (1998).

Kaneider et al., "'Role Reversal' for the Receptor PAR1 in Sepsis-Induced Vascular Damage," Nature Immunology, 8:1303-1312 (2007).

Kilpatrick et al., "7TM Receptors: The Splicing on the Cake," Elsevier Science, 20:294-301 (1999).

Miller et al., "Insider Access: Pepducin Symposium Explores a New Approach to GBCR Modulation," Annals of the New York Academy of Sciences, 1180:E1-E12 (2009).

Milligan, "Receptors as Kissing Cousins," Science. 288:65-67 (2000).

Mukherjee et al., "β-Arrestin-Dependent Desensitization of Luteinizing Hormone/Choriogonadotropin Receptor is Prevented by a Synthetic Peptide Corresponding to the Third Intracellular Loop of the Receptor," The Journal of Biological Chemistry, 274:12984-12989 (1999).

Nabhan et al., "The Alternatively Spliced Type II Corticotropin-Releasing Factor Receptor, Stably Expressed in LLCPK-1 Cells, is Not Well Coupled to the G Protein(s), Biochemical and Biophysical Research Communications," 212:1015-1021 (1995).

Nakamura et al., "A New Type of Human Calcitonin Receptor Isoform Generated by Alternative Splicing," Biochemical and Biophysical Research Communications, 209:744-751 (1995).

Nakamura et al., "Signaling and Phosphorylation-Impaired Mutants of the Rat Follitropin Receptor Reveal an Activation- and Phosphorylation-Independent but Arrestin-Dependent Pathway for Internalization," The Journal of Biological Chemistry, 273:24346-24354 (1998).

Nakamura et al., "The Agonist-Induced Phosphorylation of the Rat Follitropin Receptor Maps to the First and Third Intracellular Loops," Molecular Endocrinology, 12:580-591 (1998).

Naro et al., "Phospholipase D- and Protein Kinase C Isoenzyme-Dependent Signal Transduction Pathways Activated by the Calcitonin Receptor," Endocrinology, 139:3241-3248 (1998).

Okamoto et al., "A Simple Structure Encodes G Protein-Activating Function of the IGF-II/Mannose 6-Phosphate Receptor," Cell, 62:709-717 (1990).

Palm et al., "Mapping of β-Adrenoceptor Coupling Domains to $G_s$-Protein by Site-Specific Synthetic Peptides," FEBS Letters, 254:89-93 (1989).

Peluso et al. "Distribution of Nociceptin/Orphanin FQ Receptor Transcript in Human Central Nervous System and Immune Cells," Journal of Neuroimmunology, 81:184-192 (1998).

Schipani et al., "A Constitutively Active Mutant PTH-PTHrP Receptor in Jansen-Type Metaphyseal Chondrodysplasia," Science, 268:98-100 (1995).

Schneider et al., "A C-Terminally Truncated Human Parathyroid Hormone Receptor is Functional and Activates Multiple G Proteins," FEBS Letters, 351:281-285 (1994).

Schöneberg et al., "Plasma Membrane Localization and Functional Rescue of Truncated Forms of a G Protein-Coupled Receptor," The Journal of Biological Chemistry, 270:18000-18006 (1995).

Shinagawa et al., "Circular Dichroism Studies of the Interaction between Synthetic Peptides Corresponding to Intracellular Loops of β-Adrenergic Receptors and Phospholipid Vesicles," J. Biochem, 115:463-468 (1994).

Tardieu, "Second Messengers' Accumulation Assays Advanced Tools to Investigate All Compound Classes of GPCR Activations", Genetic Engineering Biotechnology News, Assay Tutorials, vol. 29 (2009).

Taylor et al., "Binding of an α2 Adrenergic Receptor Third Intracellular Loop Peptide to Gβ and the Amino Terminus of Gα," The Journal of Biological Chemistry, 269:27618-27624 (1994).

Taylor et al., "Peptides as Probes for G Protein Signal Transduction," Cellular Signaling, 6:841-849 (1994).

Tressel et al., "Pharmacology. Biodistribution, and Efficacy of GPCR-Based Pepducins in Disease Models," Methods in Molecular Biology, 683:259-275 (2011).

Trivedi et al., "Platelet Matrix Metalloprotease-1 Mediates Thrombogenesis by Activating PAR1 at a Cryptic Ligand Site," Cell, 137:332-343 (2009).

Varrault et al., "5-Hydroxytryptamine$_{1A}$ Receptor Synthetic Peptides," The Journal of Biological Chemistry, 269:16720-16735 (1994).

Vitiello et al., "Development of a Lipopeptide-Based Therapeutic Vaccine to Treat Chronic HBV Infection," J. Clin. Invest., 95:341-349 (1995).

Voss et al., "Amphipathic α-Helical Structure Does Not Predict the Ability of Receptor-Derived Synthetic Peptides to Interact with Guanine Nucleotide-Binding Regulatory Proteins," The Journal of Biological Chemistry, 268:4637-4642 (1993).

Wagner et al., "Differential Regulation of G Protein α-Subunit GTPase Activity by Peptides Derived from the Third Cytoplasmic Loop of the α2-Adrenergic Receptor," FEBS Letters, 365:13-17 (1995).

Wakamatsu et al., "Interaction of Peptide Fragments Corresponding to Cytoplasmic Loops of G Protein-Coupled Receptors with G Protein and Phospholipid Membrane," Pept. Chem., 1992:677-680 (1993).

Wilson et al., "Orphan G-Protein-Coupled Receptors: The Next Generation of Drug Targets," British Journal of Pharmacology, 125:1387-1392 (1998).

Wu et al., "Single Amino Acid Substitution of Serine82 to Asparagine in First Intracellular Loop of Human Cholecystokinin (CCK)—B Receptor Confers Full Cyclic AMP Responses to CCK and Gastrin," The American Society for Pharmacology and Experimental Therapeutics, 55:795.

Yu et al., "Intrathecal $CGRP_{8-37}$—Induced Bilateral Increase in Hindpaw Withdrawal Latency in Rats with Unilateral Inflammation," British Journal of Pharmacology, 117:43-50 (1996).

Adachi et al., "Functional Domains of Human Endothelin Receptor.," J. Cardiovasc. Pharmacol., 8:S121-S124(1993).

Al-Obeidi et al., "Peptide and Peptidomimetic Libraries. Molecular Diversity and Drug Design," Mol. Biotechnol., 9:205-223 (1998).

An et al., "Identification of cDNAs Encoding Two G Protein-Coupled Receptors for Lysosphingolipids," FEBS Lett., 417:279-282 (1997).

Attwood et al., "Design of a Discriminating Fingerprint for G-Protein-Coupled Receptors," Protein Engineering, 6:167-176 (1993).

Attwood et al., "Fingerprinting G-Protein-Coupled Receptors," Protein Engineering, 7:195-203 (1994).

Bischoff et al., "Lysosphingolipid Receptor-Mediated Diuresis and Natriuresis in Anaesthetized Rats," British Journal of Pharmacology, 132:1925-1933 (2001).

Bockaert et al., "Molecular Tinkering of G Protein-Coupled Receptors: An Evolutionary Success," The EMBO Journal, 18:1723-1729 (1999).

Chun et al., "A Growing Family of Receptor Genes for Lysophosphatidic Acid (LPA) and Other Lysophospholipids (LPs)," Cell Biochem. Biophys.;30:213-242 (1999).

Colombo et al., "Gs Regulation of Endosome Fusion Suggests a Role for Signal Transduction Pathways in Endocytosis," The Journal of Biological Chemistry, 269:14919-14923 (1994).

Covic et al, "Pepducin-Based Intervention of Thrombin-Receptor Signaling and Systemic Platelet Activation," Nature Medicine, 8:1161-1165 (2002).

Cunningham et al., "High-Resolution Epitope Mapping of hGH-Receptor Interactions by Alanine-Scanning Scanning Mutagenesis," Science, 244:1081-1085 (1989).

Eder et al., "Constitutive and Lysophosphatidic Acid (LPA)-induced LPA Production: Role of Phospholipase D and Phospholipase A21," Clinical Cancer Research, 6:2482-2491 (2000).

Eichler et al., "Peptide, Peptidomimetic, and Organic Synthetic Combinatorial Libraries," Med. Res. Rev., 15:481-496 (1995).

Harmer, "Family-B G-Protein-Coupled Receptors," Genome Biology, 21:1-10 (2001).

Heesen et al., "Cloning and Chromosomal Mapping of an Orphan Chemokine Receptor: Mouse RDC1," Immunogenetics, 47:364-370 (1998).

Hermanson, Bioconjugate Techniques, Book, Table of Contents and pp. 3-26 (1996).

Hogaboam et al., "The Therapeutic Potential in Targeting CCR5 and CXCR4 Receptors in Infectious and Allergic Pulmonary Disease," Pharmacology & Therapeutics, 107:314-328 (2005).

Hruby et al., "Synthesis of Oligopeptide and Peptidomimetic Libraries," Currant Opinion in Chemical Biology, 1:114-119 (1997).

Jung et al., "Conformation of a β-Adrenoceptor-Derived Signal Transducing Peptide as Inferred by Circular Dichroism and $^1$H NMR Spectroscopy," Biochemistry, 35:6399-6405 (1996).

Kahn et al., "Protease-activated receptors 1 and 4 mediate activation of human platelets by thrombin," Journal of Clinical Investigation, US, 103:879-887 (1999).

Kolakowski, "GCRDb: A G-Protein-Coupled Receptor Database," Receptors and Channels, 2:1-7 (1994).

König et al., "Three Cytoplasmic Loops of Rhodopsin Interact with Transducin," Proc. Natl. Acad. Sci. USA, 86:6878-6882 (1989).

Ladoux et al., "Coordinated Up-Regulation by Hypoxia of Adrenomedullin and One of its Putative Receptors (RDC-1) in Cells of the Rat Blood-Brain Barrier," The Journal of Biological Chemistry, 275:39914-39919 (2000).

Lang et al., "Conserved Transducer Coupling but Different Effector Linkage Upon Expression of the Myeloid fMet-Leu-Phe Receptor in Insulin Secreting Cells," The EMBO Journal, 12:2671-2679 (1993).

Leger et al., "Protease-Activated Receptors in Cardiovascular Diseases," Circulation, 114:1070-1077 (2006).

Loetscher et al., "Cloning of a Human Seven-Transmembrane Domain Receptor, LESTR, That is Highly Expressed in Leukocytes," Journal of Biological Chemistry, 269:232-237 (1994).

Marin et al., "The Amino Terminus of the Fourth Cytoplasmic Loop of Rhodopsin Modulates Rhodopsin-Transducin Interaction," The Journal of Biological Chemistry, 275:1930-1936 (2000).

Mechoulam et al., "A Random Walk Through a Cannabis Field," Pharmacology Biochemistry & Behavior, 40:461-464 (1991).

Milligan et al., "Chimaeric G Proteins: Their Potential Use in Drug Discovery," TiPS, 20:118-124 (1999).

Moro et al., "Overlapping Multi-Site Domains of the Muscarinic Cholinergic Hm1 Receptor Involved in Signal Transduction and Sequestration," The Journal of Biological Chemistry, 269:6651-6655 (1994).

O'Dowd et al., "Palmitoylation of the Human β2-Adrenergic Receptor," The Journal of Biological Chemistry, 264:7564-7569 (1989).

Postma et al., "Sphingosine-1-Phosphate Rapidly Induces Rho-Dependent Neurite Retraction: Action Through a Specific Cell Surface Receptor," The EMBO Journal, 15:2388-2395 (1996).

Probst et al., "Sequence Alignment of the G-Protein Coupled Receptor Superfamily," DNA and Cell Biology, 11:1-20 (1992).

Prossnitz et al., "The N-Formyl Peptide Receptor: A Model for the Study of Chemoattractant Receptor Structure and Function," Pharmacol. Ther., 74:73-102 (1997).

Qian et al., "Evidence for the Involvement of Several Intracellular Domains in the Coupling of Oxytocin Receptor to Gαq/11," Cell. Signal., 10:101-105 (1998).

Reggio, "Ligand-Ligand and Ligand-Receptor Approaches to Modeling the Cannabinoid CB1 and CB2 Receptors: Achievements and Challenges," Curr. Med. Chem., 6:665-683 (1999).

Ripka et al., "Peptidomimetic Design," Current Opinion in Chemical Biology 2:441-452 (1998).

Robbins et al., "Myristoylation and Differential Palmitoylation of the HCK Protein-Tyrosine Kinases Govern Their Attachment to Membranes and Association with Caveolae," Molecular Cellular Biology, 15:3507-3515 (1995).

Seitz et al, "Synthetic Peptide Conjugates-Tailor-Made Probes for the Biology of Protein Modification and Protein Processing," Tetrahedron, 57:2247-2277 (2001).

Sharpe, "Cannabis: Time for Scientific Evaluation of This Ancient Remedy?," Anesth. Analg., 90:237-240 (2000).

Shimizu et al., "A Putative G Protein-Coupled Receptor, RDC1, Is a Novel Coreceptor for Human and Simian Immunodeficiency Viruses," Journal of Virology, 74:619-626 (2000).

Stephens et al., "A Sequence within the Cytoplasic Tail of Gpllb Independently Activates Platelet Aggregation and Thromboxane Synthesis," The Journal of Biological Chemistry, 273:20317-20322 (1998).

Takuwa et al., "Subtype-Specific, Differential Activities of the EDG Family Receptors for Sphingosine-1-Phospate, a Novel Lysophospholipid Mediator," Molecular and Cellular Endocrinology, 177:3-11 (2001).

Taylor et al., "Coupling an α2-Adrenergic Receptor Peptide to G-Protein: A New Photolabeling Agent," Peptides, 15:829-834 (1994).

Thomas et al., "Molecular Cloning of the fMet-Leu-Phe Receptor from Neutrophils," The Journal of Biological Chemistry, 265:20061-20064 (1990).

Trejo et al, "Protease-Activated Receptors: New Concepts in Regulation of G Protein-Coupled Receptor Signaling and Trafficking," The Journal of Pharmacology and Experimental Therapeutics, 307:437-442 (2003).

Wong et al., "Chimeric Muscarinic Cholinergic:β-Adrenergic Receptors That Are Functionally Promiscuous Among G Proteins," The Journal of Biological Chemistry, 269:18968-18976 (1994).

i3 LOOP

```
PAR1   RCLSSSAVANRS------------------------------------------------------KKSRALF    SEQ ID NO:1
PAR2   RMLRSSAMDENS------------------------------------------------------EKGKGRALK  SEQ ID NO:7
CCKB   RELYLGLRFDGDSDSQSRVRNQGGLPGAVHQNGRCRPETGAVG--EDSDGCYVQLPRSRPALELTALTAPGPGSGSR----PTQAKLLAKKRVVR  SEQ ID NO:19
CCKA   -------------------------------------------KPSTTSSGKYEDSDGCYLQKTRPPRKCLELRQLSTGSSSRANRIRSNSSAANLMAKKRVIR  SEQ ID NO:20
Sub P  LELYQGIKFEASQKKSAKER-----------------------------------------------SDRYHEQVSAKRKVVK  SEQ ID NO:21
SSTR2  ITLWASEIPGDS------------------------------------------------------IRVGSSKRKKSEKKVTR  SEQ ID NO:22
PAR4   KVKSSG------------------------------------------------------------RRYGHALR    SEQ ID NO:9
       HTLAASG
```

Fig. 6A

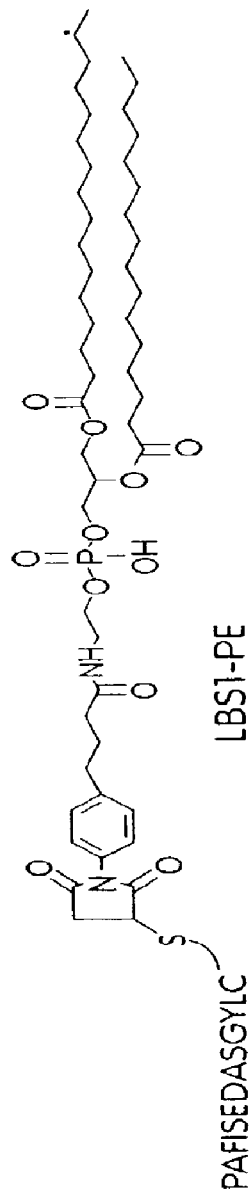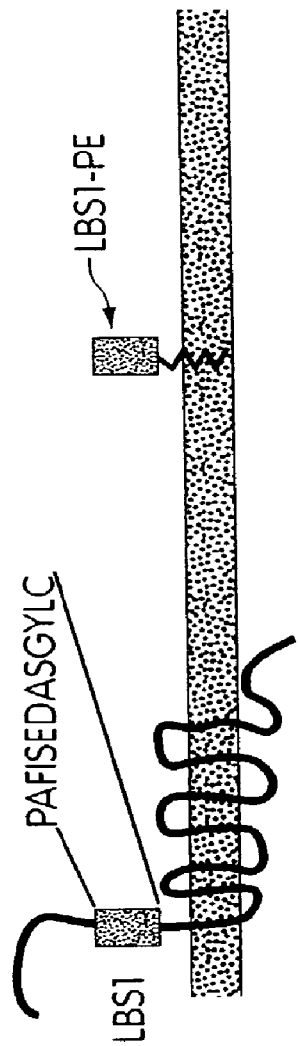

| Y12pal-18 | Pal-YVRTRGVGKVPRKKVNVF-$NH_2$ | SEQ ID NO:33 |
| Y12pal-24 | Pal-KELYRSYVRTRGVGKVPRKKVNVF-$NH_2$ | SEQ ID NO:34 |

G1pal-15    Pal-ANLMSKTDIKCRLAF-*NH₂*      SEQ ID NO:35

G1pal-23    Pal-SIVVSKLKANLMSKTDIKCRLAF-*NH₂*    SEQ ID NO:36

G PROTEIN COUPLED RECEPTOR ANTAGONISTS AND METHODS OF ACTIVATING AND INHIBITING G PROTEIN COUPLED RECEPTORS USING THE SAME

RELATED APPLICATIONS

This application is a continuation of U.S. Ser. No. 10/251,703, filed on Sep. 20, 2002, now U.S. Pat. No. 7,696,168, which is a continuation-in-part of U.S. Ser. No. 09/841,091, filed on Apr. 23, 2001, now U.S. Pat. No. 6,864,229, which claims the benefit of U.S. Ser. No. 60/198,993, filed on Apr. 21, 2000, each of which is incorporated herein in its entirety.

STATEMENT AS TO FEDERALLY SPONSORED RESEARCH

This invention was made with U.S. Government support under National Institutes of Health grants R01HL64701 and R01HL57905. The government has certain rights in the invention.

FIELD OF THE INVENTION

The invention relates generally to G protein coupled receptors and in particular to agonists and antagonists of G protein receptors and methods of using the same.

BACKGROUND OF THE INVENTION

A variety of hormones, neurotransmitters and biologically active substances control, regulate, or adjust the functions of living bodies via specific receptors located in cell membranes. Many of these receptors mediate the transmission of intracellular signals by activating guanine nucleotide-binding proteins (G proteins) to which the receptor is coupled. Such receptors are generically referred to as G protein coupled receptors ("GPCR"s). Binding of a specific signaling molecule to the GPCR can cause a conformational change in the receptor, resulting in a form that is able to bind and activate a G protein, thereby triggering a cascade of intracellular events that eventually leads to a biological response. Typically, GPCRs interact with G proteins to regulate the synthesis of intracellular second messengers such as cyclic AMP, inositol phosphates, diacylglycerol and calcium ions.

GPCRs play a vital role in the signaling processes that control cellular metabolism, cell growth and motility, adhesion, inflammation, neuronal signaling, and blood coagulation. G protein coupled receptor proteins also have a very important role as targets for a variety of signaling molecules which control, regulate, or adjust the functions of living bodies.

Known GPCR agonists and antagonists act on the extracellular surface of the GPCR. However, there are currently no effective strategies to directly study the mechanism of receptor-G protein coupling in a controlled fashion under in vivo conditions. Nor is there an understanding of the selective contacts between receptors and G proteins, or the elucidation of the mechanisms of G protein activation by receptors.

A need remains in the art for compositions which are useful to modulate GPCR activity, and also to elucidate and further define a general strategy for development and screening of novel therapeutics targeted to G-protein coupled receptor-effector interfaces.

SUMMARY OF THE INVENTION

The present invention is based on the discovery that attachment of a cell-penetrating or cell membrane-associating moiety to peptides derived from a GPCR produces agonists and/or antagonists of receptor-G protein signaling. These modified peptides—termed pepducins—exhibit selectivity for their cognate receptor. Pepducins for protease-activated receptors (PARs), e.g., PAR1, PAR2, and PAR4, cholecystokinins A and B (CCKA, CCKB), somatostatin-2 (SSTR2), melanocortin-4 (MC4R), glucagon-like peptide-1 receptor (GLP-1R), and $P2Y_{12}$ ADP receptor are agonists and/or antagonists for the receptors from which they are derived. These compositions are useful to activate or inhibit the activity of a broad range of GPCRs. Human PARs include PAR1 (Genbank Accession Number AF019616); PAR2 (Genbank Accession Number XM_003671); PAR3 (Genbank Accession Number NM_004101); and PAR4 (Genbank Accession Number NM 003950.1), the sequences of which are hereby incorporated by reference.

Accordingly, the invention provides a composition containing a polypeptide component which includes an isolated fragment of a G-protein coupled receptor (GPCR) linked to a cell penetrating component or a component that associates with a cell surface membrane (a membrane tethering moiety).

A naturally-occurring GPCR is a cell surface molecule that crosses a cell membrane at least once. For example, many naturally-occurring GPCRs cross a cell membrane seven times and contain several intracellular domains. Preferably, the isolated fragment of a GPCR includes an intracellular domain of a GPCR, e.g., one of more of the following domains: a first intracellular loop, a second intracellular loop, a third intracellular loop, and a C-terminal cytoplasmic domain. The intracellular portion is selected from an intracellular domain of a one-transmembrane domain G-protein coupled receptor of a cytokine GPCR, or a fragment thereof, or an intracellular domain of a multi-polypeptide-GPCR, such as a GPIb/V/IX receptor or a collagen receptor.

Alternatively, the isolated GPCR fragment includes an extracellular portion of a GPCR which can include a portion of the N-terminal extracellular domain, the second extracellular loop, the third extracellular loop, or the fourth extracellular loop. In other embodiments, the GPCR fragment includes the cytoplasmic tail of the GPCR or a portion of the ligand binding site of the GPCR.

Thus, the invention provides a composition containing a polypeptide which includes an isolated fragment of a G-protein coupled receptor (GPCR) linked to a non-peptidic cell penetrating moiety. Alternatively, the invention provides a composition containing a polypeptide which includes an isolated fragment of a G-protein coupled receptor (GPCR) linked to a non peptidic membrane-tethering moiety.

The invention also provides a composition containing a polypeptide which includes an isolated intracellular fragment of a G-protein coupled receptor (GPCR) or an isolated extracellular fragment of a G-protein coupled receptor (GPCR) linked to a cell penetrating moiety. Additionally, a composition which includes polypeptide which is an isolated intracellular fragment of a G-protein coupled receptor (GPCR) or an isolated extracellular fragment of a G-protein coupled receptor (GPCR) linked to a membrane-tethering moiety.

In one aspect, the extracellular or intracellular fragment of the GPCR is at least 3 contiguous amino acid residues, and more preferably, at least 5 contiguous amino acid residues.

The invention also includes soluble chimeric polypeptides. These peptides include a first domain which includes an extracellular or an intracellular fragment of a GPCR, and a second domain, linked to the first domain, which includes a cell-penetrating or a membrane-tethering moiety. The cell-penetrating- or membrane-tethering moiety optionally includes a naturally occurring contiguous amino acid from a transmembrane domain adjacent to the extracellular or intracellular fragment. For example, the construct contains at least 3, but less than 16 contiguous amino acids of a GPCR transmembrane helix domain. The transmembrane domain is not transmembrane domain 1-7 of the CXCR4, transmembrane domain 1-7 of CCKA receptor, or transmembrane 2 of the CCR5 receptor.

In one embodiment, the soluble chimeric polypeptide has a first domain which includes an extracellular or an intracellular fragment of a GPCR, and a second domain containing cell-penetrating or a membrane-tethering moiety, linked to the first domain. The second domain includes 1-15 contiguous amino acids of a naturally-occurring transmembrane helix domain immediately adjacent to the extracellular or intracellular fragment.

A GPCR is a membrane protein which binds to a signaling molecule. Upon binding, a conformational change occurs, which allows binding of the GPCR to, and activation of, a G-protein. The activated G-protein then interacts with an effector molecule, which is typically involved in a second messenger pathway. A GPCR agonist is a composition that activates a GPCR to mimic the action of the endogenous signaling molecule specific to that receptor. A GPCR antagonist is a composition that inhibits GPCR activity. GPCR activity is measured by ability to bind to an effector signaling molecule such as G-protein. An activated GPCR is one, which is capable of interacting with, and activating a G-protein. An inhibited receptor has a reduced ability to bind extracellular ligand and/or productively interact with, and activate a G-protein.

The present invention also provides an inhibitor of platelet activation, comprising a polypeptide comprising an isolated platelet-inhibitory fragment of a protease activated receptor and a cell penetrating moiety linked to said polypeptide.

In one embodiment, the inhibitor of platelet activation comprises an isolated platelet-inhibitory fragment of a protease activated receptor, wherein the protease activated receptor is a thrombin receptor, a trypsin receptor, a clotting factor Xa receptor, an activated protein C receptor, a tryptase receptor, or a plasmin receptor. In another embodiment, the thrombin receptor is PAR-4 or PAR-1. In yet another embodiment, the said polypeptide is SEQ ID NO: 29 or SEQ ID NO: 4. In yet another embodiment, the inhibitor of platelet activation further comprises P4pal10. In yet another embodiment, the inhibitor of platelet activation further comprises P1pal12.

The present invention also provides methods of inhibiting platelet aggregation, comprising contacting a platelet with a composition comprising an isolated fragment of a protease activated receptor linked to a cell penetrating moiety. In one embodiment, the protease activated receptor is a thrombin receptor. Optionally, the thrombin receptor is a PAR-1 receptor or a PAR-4 receptor.

The present invention also provides methods of inhibiting thrombus formation in a mammal, comprising administering to said mammal a composition comprising an isolated fragment of a thrombin receptor linked to a cell penetrating moiety. In one embodiment, the isolated fragment of a thrombin receptor is a PAR-4 or a PAR-1 receptor. In one embodiment, said composition is infused into a vascular lumen. For example, the lumen is in a jugular vein or a peripheral vein. In yet another embodiment, said composition is infused into a perivascular space. In another embodiment, said composition is administered transdermally, subdermally, or subcutaneously. In one example, said composition is administered to a lung tissue of said mammal. In another embodiment, said composition is administered into the peritoneal cavity of said mammal. In yet another embodiment, said composition is administered vaginally or rectally to said mammal.

The present invention also provides a vascular endoprosthetic device, comprising an inhibitor of thrombus formation, said inhibitor comprising an isolated fragment of a thrombin receptor linked to a cell penetrating moiety. In one embodiment, said device is a stent. In another embodiment, said device is a catheter.

In another embodiment, said device is impregnated with said inhibitor. In yet another embodiment, said device is coated with said inhibitor.

The present invention also provides a method of inhibiting migration or invasion of a tumor cell, comprising contacting said tumor cell with an isolated fragment of a protease activated receptor linked to a cell penetrating moiety. In one embodiment, the isolated fragment of a protease activated receptor is a PAR-4, PAR-2 or a PAR-1 receptor. In another embodiment, the isolated fragment of a protease activated receptor comprises SEQ ID NO:3, SEQ ID NO:4, SEQ ID NO:7, SEQ ID NO:8, or SEQ ID NO:29. In another embodiment, method of inhibiting migration or invasion of a tumor cell, comprises contacting said tumor cell with an isolated fragment of a protease activated receptor linked to a cell penetrating moiety, which comprises P4pal10, P1pal12, P2pal21, P2pal21F, or P1pal7.

The present invention also provides a method of inhibiting metastases of a tumor cell, comprising contacting said tumor cell with an isolated fragment of a protease activated receptor linked to a cell-penetrating moiety. In one embodiment, the isolated fragment of a protease activated receptor is a PAR-4, PAR 2, or a PAR-1 receptor. In another embodiment, the isolated fragment of a protease activated receptor comprises SEQ ID NO:3, SEQ ID NO:4, SEQ ID NO:7, SEQ ID NO:8, or SEQ ID NO:29. In yet another embodiment, the instant method of inhibiting metastases of a tumor cell, comprises contacting said tumor cell with an isolated fragment of a protease activated receptor linked to a cell-penetrating moiety which comprises P4pal10, P1pal12, P2pal21, P2pal21F, or P1pal7. In yet another embodiment, the instant method of inhibiting metastases of a tumor cell applies to tumor cell selected from the group consisting of a melanoma cell, a lung cancer cell, a breast cancer cell, a colon cancer cell, a central nervous system cancer cell, a liver cancer cell, a stomach cancer cell, a renal cancer cell, a prostate cancer cell, a sarcoma cell, a leukemia cell, or a lymphoma cell.

The present invention also provides a method of inhibiting asthma in a subject, comprising administering to said subject a composition comprising an isolated fragment of a thrombin or trypsin/tryptase GPCR linked to a cell penetrating moiety. In one embodiment, the isolated fragment of a GPCR is a PAR-1, PAR-2 or PAR-4 receptor. In another embodiment, the isolated fragment of a GPCR comprises SEQ ID NO:3, SEQ ID NO:4, SEQ ID NO:7, SEQ ID NO:8, or SEQ ID NO:29. In yet another embodiment, said composition comprises P4pal10, P1pal12, P2pal21, P2pal21F, or P1pal7. In yet another embodiment, said composition is infused into a vascular lumen. In another embodiment, said composition is introduced by aerosol into the lungs of said subject.

The present invention also provides an inhibitor of platelet activation, comprising a polypeptide comprising an isolated fragment of a nucleotide GPCR and a cell penetrating moiety linked to said polypeptide. In one embodiment, the inhibitor comprises an isolated fragment of a nucleotide GPCR, wherein the nucleotide receptor is a $P2Y_{12}$ receptor. In another embodiment, the inhibitor comprises a polypeptide wherein said polypeptide is SEQ ID NO:33 or SEQ ID NO:34. In yet another embodiment, said inhibitor comprises Y12Pal-18. In another embodiment, said inhibitor comprises Y12Pal-24.

The present invention also provides a method of inhibiting platelet aggregation, comprising contacting a platelet with a composition comprising an isolated fragment of a nucleotide receptor linked to a cell penetrating moiety. In one embodiment, the isolated fragment of a nucleotide receptor is a $P2Y_{12}$ receptor.

The present invention also provides a method of inhibiting thrombus formation in a mammal, comprising administering to said mammal a composition comprising an isolated fragment of a $P2Y_{12}$ receptor linked to a cell penetrating moiety. In one embodiment, said composition is infused into a vascular lumen. In one example, said lumen is a jugular vein or a peripheral vein. In yet another embodiment, said composition is infused into the lungs of said mammal. In another embodiment, said composition is injected into the peritoneal cavity of said mammal. In yet another embodiment, said composition is injected subdermally or subcutaneously into said mammal. In another embodiment, said composition is administered transdermally to said mammal.

The present invention also provides a vascular endoprosthetic device, comprising an inhibitor of thrombus formation, said inhibitor comprising an isolated fragment of a nucleotide receptor linked to a cell penetrating moiety. In one embodiment, said device is a stent. In another embodiment, said device is a catheter. In another embodiment, said device is impregnated with said inhibitor. In yet another embodiment, said device is coated with said inhibitor.

The present invention also provides a soluble chimeric polypeptide comprising: a first domain comprising an extracellular or an intracellular fragment of a GPCR; and a second domain comprising a cell-penetrating or a membrane-tethering moiety, linked to said first domain, wherein said second domain comprises a naturally occurring contiguous amino acid from a transmembrane domain adjacent to said extracellular or intracellular fragment, wherein said transmembrane domain is not transmembrane domain 1-7 of the CXCR4, transmembrane domain 1-7 of the CCKA receptor, or transmembrane 2 of the CCR5 receptor.

The present invention also provides a soluble chimeric polypeptide comprising: a first domain comprising an extracellular or an intracellular fragment of a GPCR; and a second domain comprising a cell-penetrating or a membrane-tethering moiety, linked to said first domain, wherein said second domain comprises 1-15 contiguous amino acids of a naturally-occurring transmembrane helix domain adjacent to said extracellular or intracellular fragment.

The present invention also provides a composition comprising a polypeptide, said polypeptide comprising an isolated intracellular or extracellular fragment of a G-protein coupled receptor (GPCR); and a non-peptidic cell penetrating, membrane tethering moiety linked to said polypeptide. In one embodiment, the compositions according to the present invention comprises cell penetrating moiety comprising at least 10 contiguous amino acids of a GPCR transmembrane helix domain. In another embodiment, the compositions according to the present invention comprises cell penetrating moiety comprises a $C_9$-$C_{24}$ fatty acid. In yet another embodiment, the compositions according to the instant invention comprises membrane-tethering moiety comprises 1-7 contiguous amino acids of a GPCR transmembrane helix domain. In one embodiment, said membrane-tethering moiety comprises the amino acid sequence VCYVSII (residues 1-7 of SEQ ID NO: 40). In another embodiment, said membrane-tethering moiety is selected from the group consisting of a $C_1$ acyl group, a $C_2$ acyl group, a $C_3$ fatty acid, a $C_4$ fatty acid, a $C_5$ fatty acid, a $C_6$ fatty acid, a $C_7$ fatty acid, and a $C_8$ fatty acid.

The present invention also provides chimeric polypeptide comprising a first domain comprising extracellular or intracellular portions of a G protein coupled receptor, and at least a second domain, attached to the first domain, wherein said second domain is a naturally or non-naturally occurring hydrophobic moiety, and wherein said first domain does not comprise a native extracellular ligand of said GPCR. In one embodiment of the chimeric polypeptide of the invention, the chimeric polypeptide the second domain or other domains are attached at either one end, at both ends, or at an internal position of said first domain.

In another embodiment of the chimeric polypeptide of the invention, the hydrophobic moiety is a lipid, an acyl or an amino acid. In yet another embodiment of the chimeric polypeptide of the invention, the hydrophobic moiety is selected from the group consisting of: phospholipids; steroids; sphingosines; ceramides; octyl-glycine; 2-cyclohexylalanine; benzolylphenylalanine; propionoyl ($C_3$); butanoyl ($C_4$); pentanoyl ($C_5$); caproyl ($C_6$); heptanoyl ($C_7$); capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phtanoyl (($CH_2$)$_4$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$); wherein said hydrophobic moiety is attached to said chimeric polypeptide with amide bonds, sulfhydryls, amines, alcohols, phenolic groups, or carbon-carbon bonds. In another embodiment, the hydrophobic moiety is a transmembrane domain of the GPCR or a fragment thereof.

In yet another embodiment of the chimeric polypeptide of the invention, the hydrophobic moiety is palmitate ($C_{16}$), myristoyl ($C_{12}$), capryl ($C_{10}$), caproyl ($C_6$), phospholipids, steroids, sphingosines, ceramides, octyl-glycine, 2-cyclohexylalanine, or benzolylphenylalanine, wherein the hydrophobic moiety is attached to chimeric polypeptide with amide bonds, sulfhydryls, amines, alcohols, phenolic groups, or carbon-carbon bonds.

In another embodiment of the chimeric polypeptide of the invention, the chimeric polypeptide comprises an extracellular portion selected from the group consisting of the first extracellular domain or a fragment thereof, the second extracellular loop or a fragment thereof, the third extracellular loop or a fragment thereof, and the fourth extracellular loop or a fragment thereof, of said G-protein coupled receptor.

In yet another embodiment of the chimeric polypeptide of the invention, the intracellular portion is selected from the group consisting of the first intracellular loop or a fragment thereof, the second intracellular loop or a fragment thereof, the third intracellular loop or a fragment thereof, and the fourth intracellular domain or a fragment thereof, of said G-protein coupled receptor.

In another embodiment of the chimeric polypeptide of the invention, the intracellular portion is selected from the group consisting of an intracellular domain of a one-transmembrane domain G-protein coupled receptor of the cytokine GPCR or a fragment thereof and an intracellular domain of a multi-polypeptide-GPCR. In yet another embodiment, the multi-polypeptide-GPCRs is selected from the group consisting of a GPIb/V/IX receptor and a collagen receptor.

In another embodiment of the chimeric polypeptide of the invention, the extracellular portion of the GPCR has at least 3 contiguous amino acid residues. In another embodiment, the intracellular portion has at least 3 contiguous amino acid residues or at least 5 contiguous amino acid residues. In yet another embodiment, said intracellular portion comprises the third intracellular loop of the GPCR. In another embodiment, said intracellular portion comprises at least 7 contiguous amino acid residues of the third intracellular loop.

In another embodiment of the chimeric polypeptide of the invention, the second domain of the chimeric polypeptide comprises a GPCR transmembrane domain or a fragment thereof. In another embodiment, the chimeric polypeptide comprises a transmembrane domain with at least 7 amino acid residues of TM5 or at least 14 amino acid residues of TM5. In another embodiment, the chimeric polypeptide comprises amino acid residues which are contiguous amino acid residues of TM5.

In another embodiment of the chimeric polypeptide of the invention, the G-protein coupled receptor involved is a mammalian G-protein coupled receptor. In some embodiments the G-protein coupled receptor or fragment thereof, is selected from the group consisting of a luteinizing hormone receptor, a follicle stimulating hormone receptor, a thyroid stimulating hormone receptor, a calcitonin receptor, a glucagon receptor, a glucagon-like peptide 1 receptor (GLP-1), a metabotropic glutamate receptor, a parathyroid hormone receptor, a vasoactive intestinal peptide receptor, a secretin receptor, a growth hormone releasing factor (GRF) receptor, protease-activated receptors (PARs), cholecystokinin receptors, somatostatin receptors, melanocortin receptors, ADP receptors, adenosine receptors, thromboxane receptors, platelet activating factor receptor, adrenergic receptors, 5-HT receptors, CXCR4, CCR5, chemokine receptors, neuropeptide receptors, opioid receptors, erythropoietin receptor, von Willebrand receptor, parathyroid hormone (PTH) receptor, vasoactive intestinal peptide (VIP) receptor, and collagen receptors.

In another embodiment of the chimeric polypeptide of the invention, the hydrophobic moiety is a lipid. In one aspect of this embodiment, the lipid is a palmitate lipid.

The present invention also provides a nucleic acid encoding a chimeric polypeptide comprising a first domain comprising extracellular or intracellular portions of a G protein coupled receptor, and at least a second domain, attached to the first domain, wherein said second domain is naturally or non-naturally occurring hydrophobic moieties, and wherein said first domain does not comprise a native extracellular ligand of said GPCR. The present invention also provides a recombinant vector comprising said nucleic acids encoding chimeric polypeptide and a host cell transformed with the said recombinant vector.

The present invention also provides a method for producing a chimeric polypeptide comprising cultivating the host cell transformed with the recombinant vector comprising a nucleic acid encoding chimeric polypeptide under conditions sufficient to express the GPCR receptor.

The present invention also provides a method for identifying a potential therapeutic agent for use in treatment of a pathology, wherein the pathology is related to aberrant expression or aberrant physiological interactions of a GPCR, comprising providing a cell having a GPCR or a property or function ascribable to said GPCR; contacting the cell with a composition comprising a candidate substance and further contacting the cell with a composition comprising the chimeric polypeptide, and determining whether the composition comprising the candidate substance alters the property or function ascribable to said GPCR, whereby, if an alteration observed in the presence of the substance is not observed when the cell is contacted with a composition devoid of the substance, the substance is identified as a potential therapeutic agent.

The present invention also provides a method of treating or preventing a pathology associated with a GPCR, comprising administering the chimeric polypeptide to a subject in which such treatment or prevention is desired in an amount sufficient to treat or prevent said pathology in said subject. In one embodiment, the subject is a human.

The present invention also provides a pharmaceutical composition comprising the chimeric polypeptide and a pharmaceutically acceptable carrier. In one embodiment, a pharmaceutical composition comprises the nucleic acid encoding the chimeric polypeptide and a pharmaceutically acceptable carrier.

The present invention also provides a kit comprising in one or more containers, the pharmaceutical composition comprising the chimeric polypeptide and a pharmaceutically acceptable carrier.

The present invention also provides the use of a therapeutic in the manufacture of a medicament for treating a syndrome associated with a human disease, the disease selected from a pathology associated with the chimeric polypeptide wherein said therapeutic is the chimeric polypeptide comprising a first domain comprising extracellular or intracellular portions of a G protein coupled receptor, and at least a second domain, attached to the first domain, wherein said second domain is naturally or non-naturally occurring hydrophobic moieties, and wherein said first domain does not comprise a native extracellular ligand of said GPCR.

The present invention also provides a method for screening for a modulator of activity of a GPCR comprising administering a test compound to a first test animal, wherein the test animal expresses a desired GPCR, administering a chimeric polypeptide to a second test animal, measuring the activity of said test compound in said first test animal and said polypeptide in said second test animal; and comparing the activity of said polypeptide in said second test animal with the activity of said test compound in said first test animal with the activity of the desired GPCR in a control animal not administered said polypeptide, wherein a change in the activity of said polypeptide in said first test animal relative to both said second test animal and said control animal indicates the test compound is a modulator of, an agonist of or an antagonist of said GPCR.

The present invention also includes a method of treating a pathological state in a mammal, the method comprising administering to the mammal a chimeric polypeptide comprising a first domain comprising extracellular or intracellular portions of a G protein coupled receptor, and at least a second domain, attached to the first domain, wherein said second domain is naturally or non-naturally occurring hydrophobic moieties, and wherein said first domain does not comprise a native extracellular ligand of said GPCR.

As used herein, a "fragment of a GPCR" means a peptide having a portion of the sequence of a GPCR protein which is less than the entire naturally-occurring amino acid sequence of the GPCR. An "isolated fragment of a GPCR" means a peptide having a portion of the sequence of a GPCR protein which is less than the entire sequence, and does not contain the naturally occurring flanking regions. An isolated GPCR fragment lacks one or more amino acids, which immediately flank the reference fragment in the naturally-occurring molecule. For example, an isolated fragment containing transmembrane region 5 of a reference GPCR sequence lacks at least one amino acid immediately flanking the amino terminus or carboxyterminus of transmembrane 5.

An "isolated intracellular fragment of a GPCR" means a peptide having an amino acid sequence of an intracellular loop of a GPCR protein, and does not contain a sequence from an extracellular loop or a transmembrane helix sequence flanking the intracellular loop. An "isolated extracellular fragment of a GPCR" means a peptide having an amino acid sequence of an extracellular loop of a GPCR protein and does not contain an amino acid of an intracellular loop or transmembrane sequence flanking regions of the extracellular loop.

An "isolated intracellular fragment of a GPCR" means a peptide having an amino acid sequence of an intracellular loop of a GPCR protein, and does not contain a sequence from an extracellular loop or a transmembrane helix sequence flanking the intracellular loop. An "isolated extracellular fragment of a GPCR" means a peptide having an amino acid sequence of an extracellular loop of a GPCR protein and does not contain an amino acid of an intracellular loop or transmembrane sequence flanking regions of the extracellular loop.

The invention also encompasses compositions containing an isolated transmembrane helix fragment or a hybrid transmembrane-intracellular loop or transmembrane-extracellular loop fragment linked to a membrane-tethering or a cell-penetrating moiety. An isolated transmembrane helix fragment is a peptide having an amino acid sequence of one or more contiguous amino acids, but less than all of the amino acids of a naturally-occurring GPCR transmembrane helix. A transmembrane-intracellular loop fragment contains at least 3 contiguous amino acids of a naturally-occurring intracellular loop and one or more contiguous amino acids from one or both flanking GPCR transmembrane domain(s). Preferably, a junctional residue an arginine (R), tryptophan (W) or lysine (K). A junctional residue that is located at a transition position between a hydrophobic transmembrane helix domain residues and a hydrophilic intracellular or extracellular loop domain. In some cases, this junctional residue is considered to terminate the transmembrane helix. For example, P1pal7 contains 3 amino acids of an intracellular loop (KKS) and RALF (SEQ ID NO:41) from the adjacent transmembrane domain. The 'R' is a junctional residue. In another example, P1pal19 (RCLSSSAVANRSKKSRALF) contains 14 intracellular loop residues (CLSSSAVANRSKKS), flanked by junctional arginines 'R' at both the N- and C-termini and terminating with ALF from the adjacent transmembrane domain 6.

As used herein "linked" means attached. For example, a peptide and a cell-penetrating (or membrane-tethering) moiety are attached to each other via a linkage. The linkage is a covalent bond. Preferably, the linkage is a labile bond, such as a thiol linkage or an ester linkage. One advantage of compounds with a labile linkage is reduced accumulation in body tissues, as compared to compounds with a non-labile linkage. Reduced accumulation in bodily tissues following administration to a subject is associated with decreased adverse side effects in the subject.

In addition to peptide-based pepducins, the invention encompasses compositions in which the GPCR fragment contains a peptidomimetic. For example, the invention includes pepducin compounds in which one or more peptide bonds have been replaced with an alternative type of covalent bond, which is not susceptible to cleavage by peptidases (a "peptide mimetic" or "peptidomimetic"). Where proteolytic degradation of peptides following injection into the subject is a problem, replacement of a particularly sensitive peptide bond with a noncleavable peptide mimetic renders the resulting peptide more stable and thus more useful as a therapeutic. Such mimetics, and methods of incorporating them into peptides, are well known in the art. Similarly, the replacement of an L-amino acid residue (e.g., with a D-amino acid) renders the peptide less sensitive to proteolysis.

Additionally, pepducin compounds of the invention can be synthesized as retro-inverso isomers, which include peptides of reverse sequence and chirality. Jameson et al., Nature, 368:744-746 (1994) and Brady et al., Nature, 368:692-693 (1994). The net result of combining D-enantiomers and reverse synthesis is that the positions of carbonyl and amino groups in each amide bond are exchanged, while the position of the side-chain groups at each alpha carbon is preserved. For example, if the peptide model is a peptide formed of L-amino acids having the sequence ABC, the retro-inverso peptide analog formed of D-amino acids would have the sequence CBA. The procedures for synthesizing a chain of D-amino acids to form the retro-inverso peptides are known in the art.

Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

An isolated GPCR fragment is derived from the sequence of a Class A GPCR or a Class B GPCR. The isolated GPCR fragment is a fragment from any known or unknown GPCR, including, but not limited to protease activated receptors (PARs, e.g., a thrombin receptor), a luteinizing hormone receptor, a follicle stimulating hormone receptor, a thyroid stimulating hormone receptor, a calcitonin receptor, a glucagon receptor, a glucagon-like peptide 1 receptor (GLP-1), a metabotropic glutamate receptor, a parathyroid hormone receptor, a vasoactive intestinal peptide (VIP) receptor, a secretin receptor, a growth hormone releasing factor (GRF) receptor, cholecystokinin receptors, somatostatin receptors, melanocortin receptors, nucleotide (e.g., ADP receptors), adenosine receptors, thromboxane receptors, platelet activating factor receptors, adrenergic receptors, 5-hydroxytryptamine (5-HT) receptors, chemokine receptors (e.g., CXCR4, CCR5), neuropeptide receptors, opioid receptors, erythropoietin receptor, and parathyroid hormone (PTH) receptor.

In preferred embodiments, the GPCR is a protease-activated receptor, a peptide receptor, or a nucleotide receptor. In particular embodiments, the GPCR is a PAR1, PAR2, PAR3, or a PAR4 receptor. In other embodiments, the GPCR is a glucagon-like receptor, a nucleotide receptor, such as a P2Y-$_{12}$ ADP receptor, a MC4 obesity receptor, a CXCR receptor (e.g., CXCR4) or CCR5 chemokine receptors, CCKA, or CCKB.

An isolated GPCR fragment includes a fragment of a GPCR which is less than 50 contiguous amino acid from the GPCR, and does not contain the native extracellular ligand of the GPCR. For example, the fragment contains between 3 and 30 contiguous amino acids of a GPCR. In preferred embodiments, the GPCR fragment comprises a fragment of a GPCR which is between 7 and 24 (inclusive) contiguous amino acids. For example, the fragment includes 7, 8, 9, 10, 11, 12, 13, 14, 15, 16, 17, 18, 19, 20, 21, 22, 23, or 24 contiguous amino acids of a GPCR.

Optionally, the amino acid sequence of a GPCR differs from a naturally-occurring amino acid sequence. For example, individual residues from a given domain, e.g., a transmembrane helix, extracellular, or intracellular loop, are mutated or substituted with a modified amino acid(s) to improve activity of the pepducin. Preferably, the amino acid sequence of such a GPCR analog differs solely by conservative amino acid substitutions, i.e., substitution of one amino acid for another of the same class, or by non-conservative substitutions, deletions, or insertions located at positions that do not destroy the function of the protein.

As used herein, a "cell-penetrating moiety" is a compound which mediates transfer of a substance from an extracellular space to an intracellular compartment of a cell. Cell-penetrating moieties shuttle a linked substance (e.g., a GPCR peptide) into the cytoplasm or to the cytoplasmic space of the cell membrane. For example, a cell penetrating moiety is a hydrophobic moiety. The hydrophobic moiety is, e.g., a mixed sequence peptide or a homopolymer peptide (e.g., polyleucine or polyarginine) which is at least 11 amino acids long. For example, the substance is a peptide such as a GPCR fragment or peptidomimetic. The cell penetrating moiety includes at least 10 contiguous amino acids e.g., 1-15 amino acids of a GPCR transmembrane helix domain. In particular embodiments, the hydrophobic moiety is a portion of a GPCR, such as a transmembrane region of a GPCR, e.g., transmembrane region 5 (TMR5) of a GPCR.

Cell-penetrating moieties include a lipid, cholesterol, a phospholipid, steroid, sphingosine, ceramide, or a fatty acid moiety. The fatty acid moiety can be, e.g., any fatty acid which contains at least eight carbons. For example, the fatty acid can be, e.g., a nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phytanoyl (methyl substituted $C_{15}$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); or a lignoceroyl ($C_{24}$) moiety. The cell-penetrating moiety can also include multimers (e.g., a composition containing more than one unit) of octylglycine, 2-cyclohexylalanine, or benzolylphenylalanine. The cell-penetrating moiety contains an unsubstituted or a halogen-substituted (e.g., chloro) biphenyl moiety. Substituted biphenyls are associated with reduced accumulation in body tissues, as compared to compounds with a non-substituted biphenyl. Reduced accumulation in bodily tissues following administration to a subject is associated with decreased adverse side effects in the subject.

Preferably, the cell penetrating moiety is a naturally-occurring or non-naturally occurring palmitoyl moiety. For example, the composition of the invention includes an intracellular loop 4 (i4) of a GPCR and a cys-palmitoyl moiety, e.g., the pepducin includes the i4 loop of PAR 1 or PAR4 linked to a palmitoyl moiety.

The cell-penetrating moiety is attached to the C-terminal amino acid, the N-terminal amino acid, or to an amino acid between the N-terminal and C-terminal amino acid of the GPCR fragment.

As used herein, a "membrane-tethering moiety" is a compound which associates with or binds to a cell membrane. Thus, the membrane-tethering moiety brings the substance to which the membrane-tethering moiety is attached in close proximity to the membrane of a target cell. The substance is a peptide such as a GPCR fragment or peptidomimetic. The cell membrane is a eucaryotic of procaryotic membrane. The membrane-tethering moiety, for example, is a hydrophobic moiety. The hydrophobic moiety can be, e.g., a mixed sequence peptide or a homopolymer peptide (e.g., polyleucine or polyarginine) which is less than 10 amino acids long. The membrane-tethering moiety can include at least 1-7 contiguous amino acids of a GPCR transmembrane helix domain, e.g., the membrane-tethering moiety includes the amino acid sequence VCYVSII (residues 1-7 of SEQ ID NO: 40), shown in FIG. 1A as P1-i3-26. Preferably, the membrane-tethering moiety is at least 10 contiguous amino acids (but less than 16 amino acids) of a GPCR transmembrane domain; more preferably, the membrane-tethering moiety is at least 15 contiguous amino acids of a GPCR transmembrane domain. Membrane-tethering moieties also include cholesterol, a phospholipid, steroid, sphingosine, ceramide, octyl-glycine, 2-cyclohexylalanine, benzolylphenylalanine. Other membrane-tethering moieties include a $C_1$ or $C_2$ acyl group, and a $C_3$-$C_8$ fatty acid moiety such as propionoyl ($C_3$); butanoyl ($C_4$); pentanoyl ($C_5$); caproyl ($C_6$); heptanoyl ($C_7$); and capryloyl ($C_8$).

Similar to the cell-penetrating moiety, the membrane-tethering moiety is attached to the C-terminal amino acid, the N-terminal amino acid, or to an amino acid between the N-terminal and C-terminal amino acid of the GPCR fragment in the pepducin.

Also within the invention is a composition which includes a polypeptide having an amino acid sequence of SEQ ID NOS:1-16, SEQ ID NOS:27-29, or SEQ ID NOS 33-36 linked to a cell penetrating moiety. Preferably, the cell-penetrating moiety is a palmitoyl group.

Another aspect of the invention relates to compositions according to Formula I:

$$A\text{-}X\text{-}B\text{-}Y_n \qquad (I),$$

wherein A is a cell penetrating moiety, X is a linking moiety, B is an isolated intracellular fragment or an isolated extracellular fragment of a G-protein coupled receptor (GPCR), Y is a hydrophobic peptide or a lipid, and n is zero or one. In some embodiments, X is a covalent bond between A and B, polyglycine, polyarginine, a mixed sequence hydrophobic peptide, amino acid, modified amino acid or a small molecule organic (i.e., aromatic) moiety. The covalent bond can be a labile covalent bond such as a thiol linkage or an ester linkage.

In various embodiments, the cell-penetrating moiety, A, is attached to the C-terminal amino acid, the N-terminal amino acid, or to an amino acid between the N-terminal and C-terminal amino acid of the GPCR fragment in the pepducin.

The compositions are used to treat, prevent, or ameliorate (reduce the severity of) one or more symptoms associated with diseases and conditions characterized by aberrant GPCR activity. Such diseases and conditions include thrombosis, heart attack, stroke, excessive bleeding, asthma, inflammation, pain, inflammatory pain, visceral pain, neurogenic pain, arthritis, diabetes, HIV infection, anxiety, depression, pulmonary insufficiency, and various types of cancer. Such methods are carried out by contacting a cell, which pathologically overexpresses a GPCR with a pepducin GPCR antagonist. For example, the method involves administering to a subject, e.g., a human patient, in which such treatment or prevention is desired a pepducin in an amount sufficient to reduce the severity of the pathology in the subject. The present invention also includes pharmaceutical compositions containing any of the pepducin compositions and a pharmaceutically acceptable carrier. The invention also includes kits containing the pharmaceutical compositions. The invention further includes methods of treating a pathological state in a mammal through the administration of any polypeptide of the invention.

The invention includes an inhibitor of platelet activation. The inhibitor contains an isolated fragment of a protease activated receptor and a cell penetrating moiety linked to the GPCR polypeptide. In some embodiments, the protease activated receptor is a thrombin receptor, a trypsin receptor, clotting factor Xa receptor, activated protein C receptor, tryptase receptor, or a plasmin receptor. The thrombin receptor is preferably PAR-4 or PAR-1. The isolated fragment of a thrombin receptor is preferably SEQ ID NO: 29 or SEQ ID NO: 4. For example, the inhibitor of platelet activation includes P4pal10 or P1pal12.

The invention also includes a method of inhibiting platelet aggregation, by contacting a platelet with a composition of an isolated fragment of a protease activated receptor linked to a cell penetrating moiety as described above. For example, the protease activated receptor is a thrombin receptor, such as a PAR-1 receptor or a PAR-4 receptor. Also within the invention is a method of inhibiting thrombus formation in a mammal by administering to the mammal a composition of the invention which includes an isolated fragment of a thrombin receptor linked to a cell penetrating moiety.

The methods of the invention are carried out by infusing into a vascular lumen, e.g., a jugular vein, peripheral vein or the perivascular space, the inhibitory compositions of the invention. The peripheral vein can be, e.g., a vein located in the extremities, such as the hand, wrist, or foot. In some embodiments, the composition is infused into the lungs of said mammal, e.g., as an aerosol. In other embodiments, the composition of the invention is administered by injection. In various embodiments, the injection can be into the peritoneal cavity of said mammal, subdermally, or subcutaneously. The composition of the invention can also be administered transdermally. In other embodiments, the composition of the invention is administered vaginally or rectally. The composition can be administered by implanting wound packing material or a suppository which is coated or impregnated with the composition of the invention.

Inhibitors of clot formation or platelet aggregation are used in medical devices, e.g., as coatings. For example, a vascular endoprosthetic device, e.g., a screen, stent or catheter, includes an inhibitor of thrombus formation which is an isolated fragment of a thrombin receptor linked to a cell penetrating moiety. The composition is impregnated in the device and diffuses into bodily tissues upon contact with a tissue or implantation of the device; alternatively, the device is coated with the pepducin.

Pepducins are also used to inhibit migration and invasion of a tumor cell by contacting the tumor cell with an isolated fragment of a protease activated receptor linked to a cell penetrating moiety. The protease activated receptor is a PAR-4, PAR-2, or a PAR-1 receptor, e.g., a receptor, which includes the amino acid sequence of SEQ ID NO: 3, SEQ ID NO: 4, SEQ ID NO:7, SEQ ID NO:8, or SEQ ID NO:29. In other embodiments, the composition comprises P4pal10, P1pal12, P2pal21, P2pal21F, or P1pal7. Methods of inhibiting metastases of a tumor cell are carried out by contacting the tumor cell with an isolated fragment of a protease activated receptor linked to a cell-penetrating moiety. The tumor cell is a melanoma cell, a breast cancer cell, a renal cancer cell, a prostate cancer cell, a lung cancer cell, a colon cancer cell, a central nervous system (CNS) cancer cell, a liver cancer cell, a stomach cancer cell, a sarcoma cell, a leukemia cell, or a lymphoma cell.

Symptoms of asthma are reduced by administering a thrombin or a trypsin/tryptase GPCR based pepducin. Accordingly, a method of inhibiting asthma is carried out by administering a composition containing an isolated fragment of a thrombin or a trypsin/tryptase GPCR linked to a cell penetrating moiety. Preferably, the trypsin/tryptase receptor is a PAR-1, PAR-2 or PAR-4 receptor. For example, the isolated fragment of a PAR includes SEQ ID NO: 3, SEQ ID NO: 4, SEQ ID NO: 7, SEQ ID NO: 8, or SEQ ID NO: 29. In other embodiments, the composition includes P4pal10, P1pall 2, P2pal21, P2pal21F, or P1pal7. In various embodiments, the composition is infused into a vascular lumen, such as a peripheral vein, is infused into the lungs of the mammal, e.g., by inhalation (e.g., as an aerosol), or is administered by a transdermal route.

Inhibitors of platelet activation include an isolated fragment of a nucleotide activated GPCR such as a $P2Y_{12}$ receptor linked to a cell penetrating moiety. For example, the GPCR polypeptide includes SEQ ID NO:33 or SEQ ID NO:34. In specific embodiments, the composition includes Y12Pal-18 or Y12Pal-24. Such compositions are useful in methods of inhibiting platelet aggregation.

In yet another aspect, the invention includes a method of inhibiting thrombus formation in a mammal by administering a composition including an isolated fragment of a nucleotide activated receptor linked to a cell penetrating moiety to the mammal. In some embodiments, the thrombin receptor is a $P2Y_{12}$ receptor. The method can be carried out by infusing into a vascular lumen, e.g., a jugular vein, peripheral vein the inhibitory compositions of the invention. The peripheral vein can be, e.g., a vein located in the extremities, such as the hand, wrist, or foot. In some embodiments, the composition is infused into the lungs of said mammal, e.g., as an aerosol. In other embodiments, the composition of the invention is administered by injection. In various embodiments, the injection can be into the peritoneal cavity of said mammal, subdermally, or subcutaneously. In other embodiments, the composition of the invention is administered transdermally. The composition can be administered by implanting wound packing material or a suppository which is coated or impregnated with the composition of the invention.

In another aspect, the invention includes a vascular endoprosthetic device, which includes an inhibitor of thrombus formation which is an isolated fragment of a nucleotide receptor linked to a cell penetrating moiety. In various embodiments, the device can be, e.g., a stent or a catheter. In some embodiments, the device is impregnated with or coated with the inhibitor.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification, including definitions, will control. In addition, the materials, methods, and examples are illustrative only and not intended to be limiting. All patents and publications cited in this specification are incorporated herein by reference.

BRIEF DESCRIPTION OF THE DRAWINGS

FIG. 6A is a table of an alignment of various GPCR fragments.

FIG. 6B discloses "SLIGKV" as SEQ ID NO: 17.

FIG. 10A depicts a schematic of a hypothetical mechanism of inhibition of PAR1 and PAR4 by their cognate pepducins at the intracellular surface of the plasma membrane. FIGS. 10B and 10C are graphs indicating the inhibition of aggregation of human platelets by pepducin P1pal12 and P4pal10. FIG. 10D shows fluorescence graphs demonstrating that preincubation of platelets with P4pal10 attenuates $Ca^{2+}$ signal induction. FIGS. 10B, 10D, and 10E disclose "SFLLRN" as SEQ ID NO: 23 and "AYPGKF" as SEQ ID NO: 26.

FIG. 11A shows a graph illustrating inhibition of aggregation of human platelets with P1pal12 and P4pal-10 at 3 nM Thrombin; FIG. 11B shows a graph illustrating inhibition of aggregation of human platelets with P1pal12 and P4pal-10 at 20 nM Thrombin; FIG. 11C shows a graph illustrating full platelet aggregation of murine platelets with P4pal-10 at 1 nM Thrombin; FIG. 11D shows a graph illustrating full platelet aggregation of murine platelets with P4pal-10 at 3 nM Thrombin; FIG. 11E shows a graph illustrating full platelet aggregation of murine platelets with P4pal-10 at 20 nM Thrombin. FIG. 11F shows an alignment of the third intracellular loops of human and murine PAR4.

FIG. 12A shows a fluorescence graph indicating accumulation of i3 loop peptides in circulating mouse platelets. FIG. 12B is a bar graph depicting unstable haemostasis as measured by % rebleeding from amputated tail tips in mice treated with pepducin or vehicle alone; FIG. 12C is a graph indicating total tail bleeding times for mice injected with vehicle, P1pal-12 or P4pal-10. FIG. 12D is a bar graph indicating the protective effect of P4pal10 on systemic platelet activation in mice. FIG. 12D discloses "AYPGKF" as SEQ ID NO: 26.

DETAILED DESCRIPTION OF THE INVENTION

The present invention is based on the creation of GPCR conjugates which include a GPCR moiety, derived from a GPCR or a fragment thereof, and a cell penetrating moiety which partitions the conjugate into and across the lipid bilayer of target cells. The cell penetrating moiety is, e.g., a hydrophobic region of the GPCR fragment itself. The cell penetrating (or cell surface-associating) moiety anchors the conjugate in the lipid bilayer (or to the cell surface), increasing the effective molarity of the conjugate in the vicinity of the intracellular receptor, e.g., at the receptor-G protein interface. An exogenous GPCR moiety disrupts receptor-G protein interactions and cause activation and/or inhibition of signaling. Thus, the methods and compositions, as well as the experiments detailed herein, demonstrate that selectively targeting the intracellular receptor-G-protein interface using cell-penetrating peptides results in agonists or antagonists of G-protein receptor signaling. Specifically, the conjugation of a hydrophobic moiety, such as a hydrophobic peptide or a moiety containing a long hydrocarbon chain such as a palmitoyl group, to peptides derived from a GPCR (e.g., an intracellular loop, such as the third intracellular loop, of PAR1, PAR2, or PAR4), yields full agonists and/or antagonists of G-protein receptor signaling.

The pepducins are designed to act as receptor-modulating agents by targeting the intracellular surface of the receptor. Additional pepducins include PAR1- and PAR4-based antagonists for anti-haemostatic and anti-thrombotic effects under in vivo conditions. Because thrombin is the most potent activator of platelets, PAR1 (Vu et al., Cell 64, 1057 (1991)) and PAR4 (Xu et al., Proc. Natl. Acad. Sci. (USA) 95, 6642 (1998); Covic et al., Biochemistry 39, 5458 (2000); and Covic et al., Thromb. Haemost. 87, 722 (2002)) were chosen as targets. Antagonists of these two receptors may be useful to prevent the thrombotic and proliferative complications of acute coronary syndromes. Andrade-Gordon et al., J. Pharm. Exp. Therap. 298, 34 (2001) and Ma et al., Br. J. Pharm. 134, 701 (2001).

Figure 4A:
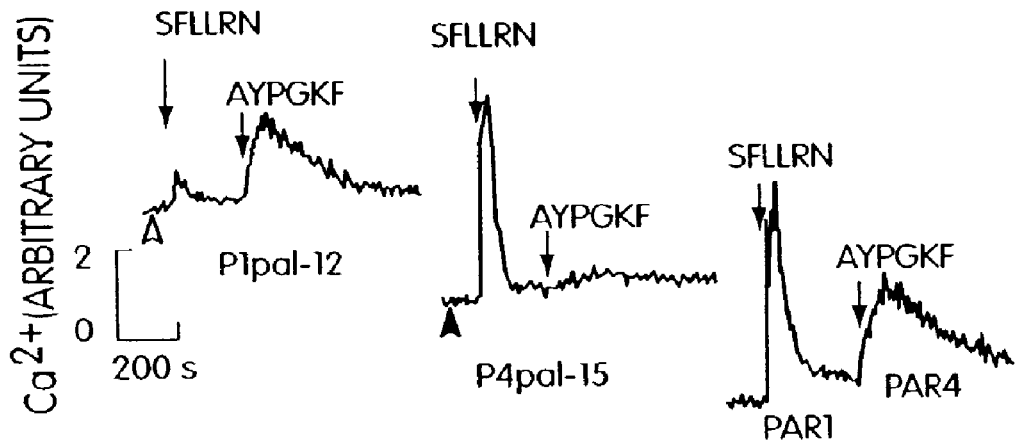
FIG. 4A is a line graph of the fluorescence excitation intensity indicating calcium levels at 340/380 nm. Figure discloses "SFLLRN" as SEQ ID NO: 23 and "AYPGKF" as SEQ ID NO: 26.
Figure 4B:
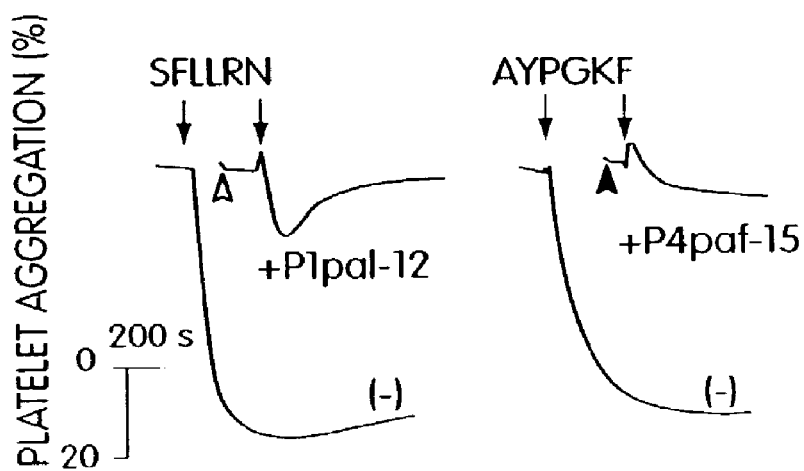
FIG. 4B is a line graph of inhibition of platelet aggregation by various peptides of the invention, as measured by light transmittance. Figure discloses "SFLLRN" as SEQ ID NO: 23 and "AYPGKF" as SEQ ID NO: 26.
Figure 4C:
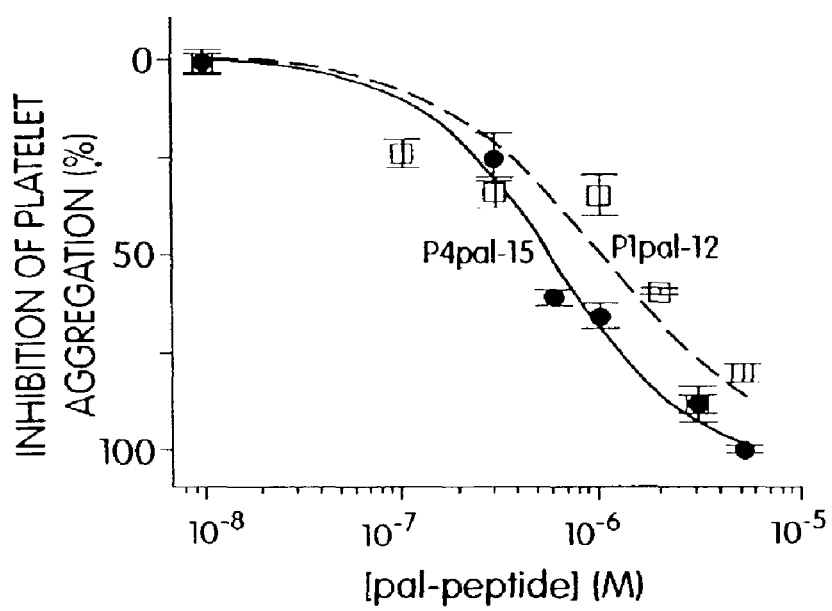
FIG. 4C is a line graph of inhibition of platelet aggregation by various peptides of the invention.
Figure 4D:
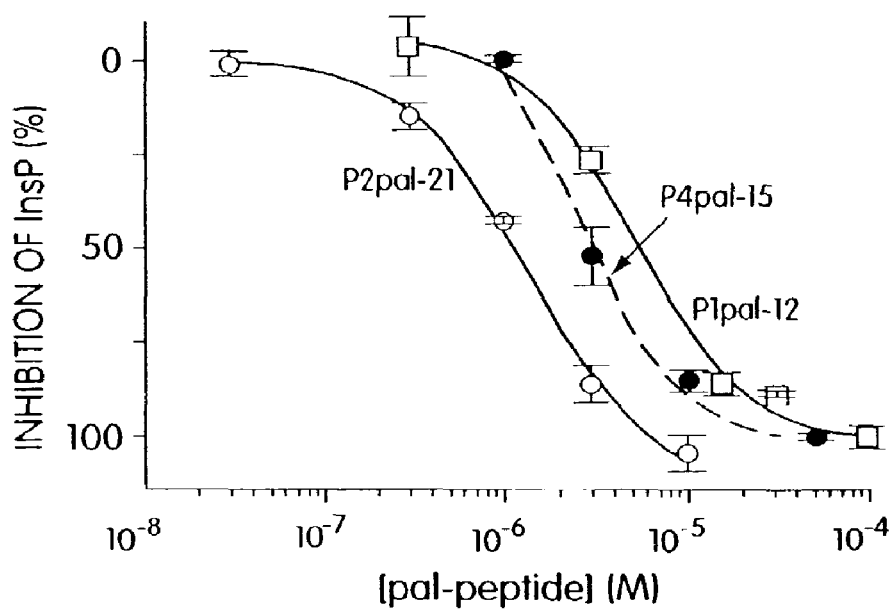
FIG. 4D is a line graph demonstrating the effect of various peptides on PLC-β activity as measured by inositol phosphate formation.
Figure 4E:
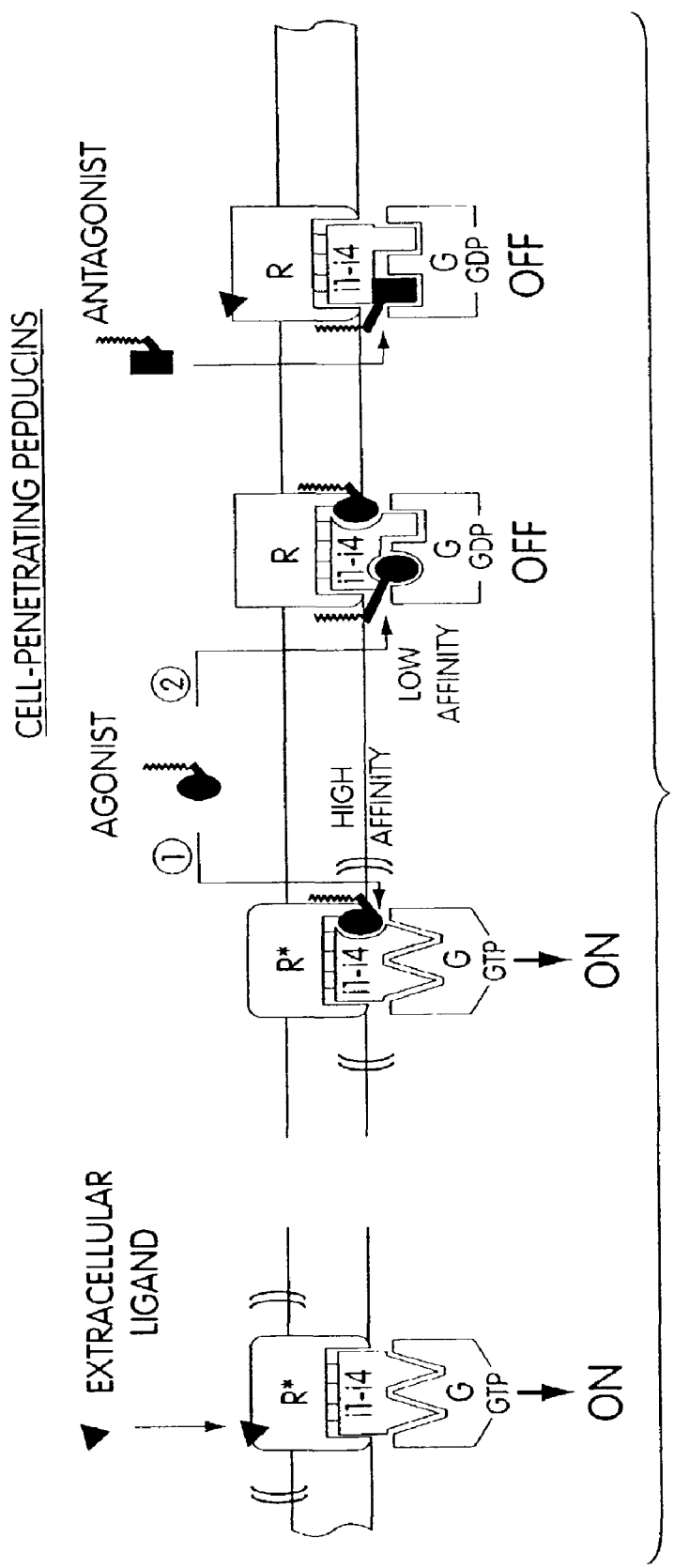
FIG. 4E is a schematic representation of activation of receptor-G-protein complexes by pepducins.

FIG. 4E shows a two-site mechanism by which pepducins both activate and inhibit receptor-G protein signaling, a two-site mechanism. The mechanism accommodates the biphasic activation and inhibition of the agonists and the inhibition of the antagonists. Pepducins, by virtue of their hydrophobic tether, rapidly transduce the plasma membrane and achieve high effective molarity at the perimembranous interface. The pepducin agonist first occupies a high-affinity site at the intracellular surface of the GPCR. The bound agonist either stabilizes or induces the activated state of the receptor to turn on the associated G protein(s). After this first site becomes saturated, higher concentrations of pepducin begin to occupy a second, lower-affinity, inhibitory site that blocks signal transference to G protein in a dominant manner, perhaps by mimicking the GPCR (e.g., the receptor i3-loop) ground-state interactions with the G protein. The inhibition by the pepducin antagonists is coincident with the inhibitory phase of the agonists, thus the antagonists may also bind at this lower affinity site. Exogenous activation or inhibition of receptors by pepducins could reflect a potential dimerization mode whereby one receptor donates its intracellular loops to an adjacent receptor. There are several examples of receptor dimers that give rise to distinct signaling properties (Milligan, Science 288, 65-67 (2000)), including the cytokine/GPCRs such as the EPO receptor (Guillard et al., J. Biol. Chem. (2001) 276, 2007-2013), however, the mechanism(s) of cross-receptor modulation is unknown.

G Protein Coupled Receptors

G protein coupled receptors are intrinsic membrane proteins which comprise a large superfamily of receptors. The family of G protein-coupled receptors (GPCRs) has at least 250 members (Strader et al. FASEB J., 9:745-754, 1995; Strader et al. Annu. Rev. Biochem., 63:101-32, 1994). It has been estimated that one percent of human genes may encode GPCRs. Many GPCRs share a common molecular architecture and common signaling mechanism. Historically, GPCRs have been classified into six families, originally thought to be unrelated, three of which are found in vertebrates. Recent work has identified several new GPCR families and suggested the possibility of a common evolutionary origin for all of them.

Many GPCRs share a common structural motif of seven transmembrane helical domains. Some GPCRs, however, do not have seven transmembrane helical domains and instead can be single-spanning transmembrane receptors.

Single spanning GPCRs include receptors for cytokines such as erythropoietin, EGF, insulin, insulin-like growth factors I and II, TGF.

GPCR families include Class A Rhodopsin like, Class B Secretin like, Class C Metabotropic glutamate/pheromone, Class D Fungal pheromone, Class E cAMP receptors (Dictyostelium), and Frizzled/Smoothened family. Putative families include Ocular albinism proteins, *Drosophila* odorant receptors, Plant Mlo receptors, Nematode chemoreceptors, and Vomeronasal receptors (V1R & V3R).

Class A Rhodopsin like receptors include: Amine receptors: Acetylcholine, Alpha Adrenoceptors, Beta Adrenoceptors, Dopamine, Histamine, Serotonin, Octopamine, and Trace amine; Peptide receptors: Angiotensin, Bombesin, Bradykinin, C5a anaphylatoxin, Fmet-leu-phe, APJ like, Interleukin-8, Chemokine receptors (C-C Chemokine, C-X-C Chemokine, BONZO receptors (CXC6R), C-X3-C Chemokine, and XC Chemokine), CCK receptors, Endothelin receptors, Melanocortin receptors, Neuropeptide Y receptors, Neurotensin receptors, Opioid receptors, Somatostatin receptors, Tachykinin receptors, (Substance P (NK1), Substance K (NK2), Neuromedin K (NK3), Tachykinin like 1, and Tachykinin like 2), Vasopressin-like receptors (Vasopressin, Oxytocin, and Conopressin), Galanin like receptors (Galanin, Allatostatin, and GPCR 54), Proteinase-activated like receptors (e.g., Thrombin), Orexin & neuropeptide FF, Urotensin II receptors, Adrenomedullin (G10D) receptors, GPR37/endothelin B-like receptors, Chemokine receptor-like receptors, and Neuromedin U receptors; Hormone protein receptors: Follicle stimulating hormone, Lutropin-choriogonadotropic hormone, Thyrotropin, and Gonadotropin; (Rhod)opsin receptors; Olfactory receptors; Prostanoid receptors: Prostaglandin, Prostacyclin, and Thromboxane; Nucleotide-like receptors: Adenosine and Purinoceptors; *Cannabis* receptors; Platelet activating factor receptors; Gonadotropin-releasing hormone receptors; Thyrotropin-releasing hormone & Secretagogue receptors: Thyrotropin-releasing hormone, Growth hormone secretagogue, and Growth hormone secretagogue like; Melatonin receptors; Viral receptors; Lysosphingolipid & LPA (EDG) receptors; Leukotriene B4 receptor: Leukotriene B4 receptor BLT1 and Leukotriene B4 receptor BLT2; and Class A Orphan/other receptors: Platelet ADP & KI01 receptors, SREB, Mas protooncogene, RDC1, ORPH, LGR like (hormone receptors), GPR, GPR45 like, Cysteinyl leukotriene, Mas-related receptors (MRGs), and GP40 like receptors.

Class B (the secretin-receptor family or 'family 2') of the GPCRs is a smaller but structurally and functionally diverse group of proteins that includes receptors for polypeptide hormones (Calcitonin, Corticotropin releasing factor, Gastric inhibitory peptide, Glucagon, Glucagon-like peptide-1, -2, Growth hormone-releasing hormone, Parathyroid hormone, PACAP, Secretin, Vasoactive intestinal polypeptide, Diuretic hormone, EMR1, Latrophilin), molecules thought to mediate intercellular interactions at the plasma membrane (Brain-specific angiogenesis inhibitor (BA1)) and a group of *Drosophila* proteins (Methuselah-like proteins) that regulate stress responses and longevity.

Class C Metabotropic glutamate/pheromone receptors include Metabotropic glutamate, Metabotropic glutamate group I, Metabotropic glutamate group II, Metabotropic glutamate group III, Metabotropic glutamate other, Extracellular calcium-sensing, Putative pheromone Receptors, GABA-B, GABA-B subtype 1, GABA-B subtype 2, and Orphan GPRC5 receptors.

GPCRs can potentially be multi-polypeptide receptors such as GPIb-V-IX, or the collagen receptor, that exhibit outside-in-signaling via G proteins.

Although hundreds of G protein coupled receptor genes or cDNAs have been cloned, it is believed that there are still many uncharacterized G protein coupled receptors which have not yet been recognized as GPCRs.

GPCRs play a vital role in the signaling processes that control cellular metabolism, cell growth and motility, adhesion, inflammation, neuronal signaling, and blood coagulation. G protein coupled receptor proteins also have a very important role as targets for a variety of signaling molecules which control, regulate, or adjust the functions of living bodies. The signaling species can be endogenous molecules (e.g., neurotransmitters or hormones), exogenous molecules (e.g., odorants), or, in the case of visual transduction, light.

For instance, GPCRs include receptors for biogenic amines, e.g., dopamine, epinephrine, histamine, glutamate (metabotropic effect), acetylcholine (muscarinic effect), and serotonin; receptors for lipid mediators of inflammation such as prostaglandins, platelet activating factor, and leukotrienes; receptors for peptide hormones such as calcitonin, C5a anaphylatoxin, follicle stimulating hormone, gonadotropin releasing hormone, neurokinin, oxytocin; receptors for proteases such as thrombin, trypsin, tryptase, activated protein C, and factor VIIa/Xa; and receptors for sensory signal mediators, e.g., retinal photopigments and olfactory stimulatory molecules. Each molecule is specific to a receptor protein, whereby the specificities of individual physiologically active substances (including specific target cells and organs), specific pharmacological actions, specific action strength, action time, etc., are decided. Thus, GPCRs are a major target for drug action and development.

Upon ligand binding, GPCRs regulate intracellular signaling pathways by activating guanine nucleotide-binding proteins (G proteins). The domain structure of GPCRs are conserved among members of the GPCR family. Domain boundaries of TM helix domains, intracellular loop domains, and extracellular domains of GPCRS are known in the art. The structure of unmapped GPCRs is determined by comparison to the prototype GPCR, rhodopsin, using known methods, e.g., as described in Palczewski et al., Science 289: 739 (2000), hereby incorporated by reference.

Figure 1A:
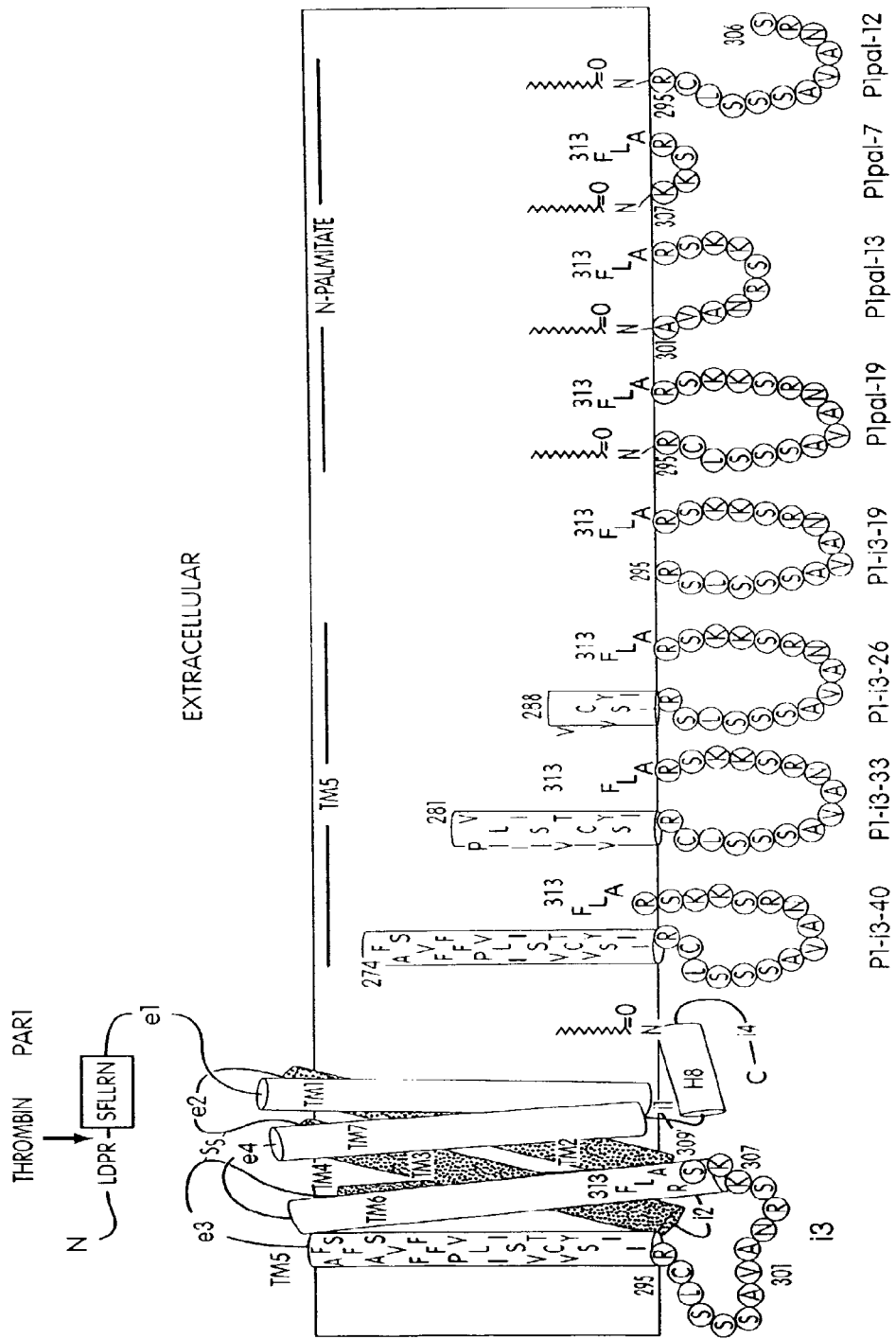
FIG. 1A is a schematic representation of PAR1. Thrombin cleaves the extracellular domain (e1) at the $R_{41}$-$S_{42}$ bond (LDPR↓SFLLRN, SEQ ID NO: 42), creating a new N terminus $_{42}$SFLLRN is an extracellular ligand of PAR1. The sequences of the peptides used in this study are shown at the bottom: TM5-i3-TM6 (SEQ ID NO: 46); P1-i3-40 (SEQ ID NO: 43); P1-i3-33 (SEQ ID NO: 44); P1-i3-26 (SEQ ID NO: 40); P1-i3-19 (SEQ ID NO: 45); P1pal-19 (SEQ ID NO: 47); P1pal-i3 (SEQ ID NO: 48); P1pal-7 (SEQ ID NO: 49); and P1pal12 (SEQ ID NO: 50).

One characteristic feature of most GPCRs is that seven clusters of hydrophobic amino acid residues, or transmembrane regions (TMs, the 7 transmembrane regions are designated as TM1, TM2, TM3, TM4, TMS, TM6, and TM7) are located in the primary structure and pass through (span) the cell membrane at each region thereof (FIG. 1A). The domains are believed to represent transmembrane alpha-helices connected by three intracellular loops and (i1, i2, and i3), three extracellular loops (e1, e2, and e3), and amino (N)- and carboxyl (C)-terminal domains (Palczewski et al., Science 289, 739-45 (2000)). Most GPCRs have single conserved cysteine residues in each of the first two extracellular loops which form disulfide bonds that are believed to stabilize functional protein structure. It is well known that these structures detailed above are common among G protein coupled receptor proteins and that the amino acid sequences corresponding to the area where the protein passes through the membrane (membrane-spanning region or transmembrane region) and the amino acid sequences near the membrane-spanning region are often highly conserved among the receptors. Thus, due to the high degree of homology in GPCRs, the identification of novel GPCRs, as well identification of both the intracellular and the extracellular portions of such novel members, is readily accomplished by those of skill in the art. FIG. 1A is a schematic representation of PAR1, indicating the topological arrangement of the membrane-spanning segments (TM1-7), extracellular loops (e1-e4), and intracellular loops (i1-i4). This structure is based on the X-ray structure of rhodopsin (Palczewski et al., Science 289, 739-45 (2000)). As shown in this figure, thrombin cleaves the extracellular domain (e1) at the R41-S42 bond creating a new N-terminus, $_{42}$SFLLRN (SEQ ID NO: 23), which functions as a tethered PAR1 agonist.

The binding sites for small ligands of G-protein coupled receptors are believed to comprise a hydrophilic socket located near the extracellular surface which is formed by several GPCR transmembrane domains. The hydrophilic socket is surrounded by hydrophobic residues of the G-protein coupled receptors. The hydrophilic side of each G-protein coupled receptor transmembrane helix is postulated to face inward and form the polar ligand binding site. TM3 has been implicated in several GPCRs as having a ligand binding site which includes the TM3 aspartate residue. TM5 serines, a TM6 asparagine and TM6 or TM7 phenylalanines or tyrosines are also implicated in ligand binding. The ligand binding site for peptide hormones receptors and receptors with other larger ligands such as glycoproteins (e.g., luteinizing hormone, follicle stimulating hormone, human chorionic gondaotropin, thyroid-stimulating hormone (Thyrotropin)), and the $Ca^{2+}$/glutamate/GABA (gamma-aminobutyric acid) classes of receptors likely reside in the extracellular domains and loops.

A key event for the switch from inactive to active receptor is ligand-induced conformational changes of transmembrane helices 3 (TM3) and 6 (TM6) of the GPCRs that have 7 transmembrane spanning helices (Gether and Kolbilka, J. Biol. Chem. 273, 17979-17982 (1998)). These helical movements in turn alter the conformation of the intracellular loops of the receptor to promote activation of associated heterotrimeric G proteins. Mutagenesis studies (Cotecchia et al., J. Biol. Chem. 267:1633-1639 (1992); Kostenis et al., Biochemistry 36:1487-1495 (1997); Kjelsberg et al., J. Biol. Chem. 267:1430-1433 (1992)) demonstrated that the third intracellular loop (i3) mediates a large part of the coupling between receptor and G protein. 13 loops expressed as minigenes have also been shown to directly compete with adrenergic receptors for Gq binding (Luttrel et al., Science 259: 1453-1457 (1993)), or can activate G proteins as soluble peptides in cell-free conditions (Okamoto et al., Cell 67, 723-730 (1991)).

One particular class of GPCR is the protease activated receptors (PARs). Protease-activated receptors (PARs) are members of the superfamily of G-protein-coupled receptors that initiate cell signaling by the proteolytic activity of extracellular serine proteases. PARs are activated after proteolytic cleavage of the amino terminus of the receptor by endogenous proteases, including thrombin (PAR-1, -3, and -4) and trypsin/tryptase (PAR-2 and -4). Of these, PAR2 (Nystedt et al., Proc. Natl. Acad. Sci. (USA) 91:9208-9212 (1994)) is a trypsin/tryptase-activated receptor that is important in inflammation and pain, and PAR4 (Xu et al., Proc. Natl. Acad. Sci. (USA) 95:6642-6646 (1998); Kahn et al., Nature (London) 394:690-694 (1998)) is a second thrombin receptor that plays a unique role in platelet aggregation (Covic et al., Biochemistry 39, 5458-5467 (2000)).

Because both thrombin, trypsin, and tryptase are present in inflamed airways, PARs are likely to play a major role in airway inflammation. Knight et al., J. Allergy Clin. Immunol. 108:797-803 (2001).

In addition to its pivotal role in hemostasis, thrombin activates various cell types such as platelets and vascular smooth muscle cells via proteolytic cleavage of specific cell-surface receptors (PARs), the prototype of which is PAR-1. Thrombin receptor activation is likely to play a key role in cardiovascular disorders such as arterial thrombosis, atherosclerosis and restenosis, and as such a thrombin receptor antagonist should have potential utility in the treatment of these disorders. Chackalamannil, Curr. Opin. Drug Discov. Devel. 4:417-27 (2001).

Thrombin is thought to be involved in functional loss after injury to the mammalian central nervous system (CNS). Down-regulation of PAR-1 has been shown to increase post-traumatic survival of CNS neurons and post-traumatic toxicity of thrombin may be down-regulated by appropriate modulation of PAR-1 receptors. Friedmann et al., Neuroimmunol., 121:12-21 (2001).

PARS are also involved in a variety of other diseases or indications, including various cancers, cellular proliferation, and pain.

GPCR Domains

Most GPCRs are characterized by seven clusters of hydrophobic amino acid residues, or transmembrane regions (TMs, the 7 transmembrane regions are designated as TM1, TM2, TM3, TM4, TMS, TM6, and TM7), that are located in the primary structure and pass through (span) the cell membrane (FIG. 1A). The TM regions are believed to represent transmembrane alpha-helices connected by three intracellular loops (i1, i2, and i3), three extracellular loops (e1, e2, and e3). GPCRs also contain amino (N)- and carboxyl (C)-terminal domains (Palczewski et al., Science 289, 739-45 (2000)). The sequences between the transmembrane regions correspond to GPCR loops, and the location of a loop within a cell determines whether it is an intracellular or an extracellular loop. Most GPCRs have single conserved cysteine residues in each of the first two extracellular loops which form disulfide bonds that are believed to stabilize functional protein structure. A schematic representation of transmembrane and loop regions of the PAR1 GPCR is presented in FIG. 1A.

One example of a GPCR is the CXCR4 receptor, shown in Table 1 as SEQ ID NO:38. The seven underlined sequences correspond to the seven transmembrane regions of the GPCR. Thus, the sequence IFLPTIYSIIFLTGIVGNGLVILV (SEQ ID NO:39) corresponds to the first transmembrane region (TM1).

TABLE 1

CXCR4

(SEQ ID NO: 38)
MEGISIYTSD NYTEEMGSGD YDSMKEPCFR EENANFNK<u>IF</u>

<u>LPTIYSIIFL TGIVGNGLVI LVMGYQKKLR</u> SMTDKYRLHL

<u>SVADLLFVIT LPFWAVDAVA</u> NWYFGNFLCK <u>AVHVIYTVNL</u>

<u>YSSVLILAFI SLDRYLAIVH</u> ATNSQRPRKL LAEKVVYVGV

WIPALLLTIP DFIFANVSEA DDRYICDRFY PNDLWVVVFQ

FQHIMVGLIL PGIVILSCYC IIISKLSHSK GHQKRKALKT

<u>TVILILAFFA CWLPYYIGIS</u> IDSFILLEII KQGCEFENTV

HKW<u>IS<u>I</u>TEAL AFFHCCLNPI LYAFLGAKFK</u> TSAQHALTSV

SRGSSLKILS KGKRGGHSSV STESESSFH SS

An isolated fragment of a GPCR is any portion of the GPCR which is less than the full length protein. A peptide containing an isolated fragment of a GPCR may contain an amino acid sequence N-terminal and/or C-terminal to the GPCR sequence other than the naturally occurring amino acid sequence. A peptide containing an isolated transmembrane sequence of a GPCR may contain only the sequence corresponding to that transmembrane region of the GPCR, or it may also contain amino acid sequences N-terminal and/or C-terminal to the transmembrane sequence, that are not the naturally occurring flanking sequences (i.e., not the loop sequences which are adjacent to that region in the naturally occurring GPCR sequence).

Thus, a peptide containing an isolated transmembrane region of the CXCR4 receptor is any peptide that contains any or all of the contiguous amino acids of an underlined region of sequence shown in Table 1. Such a peptide does not contain any of the naturally occurring (non-underlined) flanking sequence which corresponds to loop sequences which are adjacent to that TM region in the naturally occurring GPCR sequence.

Likewise, a peptide containing an isolated (intracellular or extracellular) loop region of the CXCR4 receptor is any peptide that contains any or all contiguous amino acids of a non-underlined region of sequence shown in Table 1. Such a peptide does not contain any of the naturally occurring transmembrane sequences, shown as underlined flanking sequence in Table 1, which are adjacent to that loop region in the naturally occurring GPCR sequence.

A peptide containing an isolated extracellular domain or an isolated intracellular domain can include amino acid sequences from any (extracellular or intracellular) loop and/or the N- or C-terminal domain. Such a peptide does not include any sequence from a transmembrane region which is adjacent to that extracellular domain or intracellular domain in the naturally occurring GPCR sequence.

Pharmaceutical Compositions

The pepducins (also referred to herein as "active compounds") of the invention, and derivatives, fragments, analogs and homologs thereof, can be incorporated into pharmaceutical compositions suitable for administration. Such compositions typically comprise the pepducin and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference.

A pharmaceutical composition of the invention is formulated to be compatible with its intended route of administration. Examples of routes of administration include parenteral, e.g., intravenous (e.g., a peripheral vein, such as found in the extremities), intraperitoneal, intradermal, subcutaneous, subdermal, oral, intranasal, aerosol (e.g., inhalation), transdermal (i.e., topical), transmucosal, vaginal, intrauterine, and rectal (e.g., suppositories) administration. Injectable solutions containing active compounds of the present invention may be administered to the vascular lumen of vessels (e.g., aorta or jugular vein). Alternatively, active compounds of the present invention may be administered via a device, e.g., stent or catheter, impregnated or coated with the active compounds.

Solutions or suspensions used for administration (e.g., parenteral) may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. A preparation of a pharmaceutical composition of the present invention can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation or intranasal administration, the compounds are delivered in the form of an aerosol spray from pressured container or dispenser which contains a suitable propellant, e.g., a gas such as carbon dioxide, or a nebulizer (e.g., delivery to the lung).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can also be prepared in the form of suppositories (e.g., with conventional suppository bases such as cocoa butter and other glycerides), a suppository coating, or retention enemas for rectal delivery. The active compounds can be similarly prepared for intravaginal or intrauterine administration. The active compounds may also be administered as impregnated in or as a coating on wound packing (e.g., to reduce bleeding).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pepducins and GPCR peptides can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid glycolic acid enable release of molecules for over 100 days, certain hydrogels release proteins for shorter time periods.

Controlled release of active compounds can utilize various technologies. Devices, e.g., stents or catheters, are known having a monolithic layer or a coating incorporating a heterogeneous solution and/or dispersion of an active agent in a polymeric substance, where the diffusion of a therapeutic agent is rate limiting, as the agent diffuses through the polymer to the polymer-fluid interface and is released into the surrounding fluid. Active compound may be dissolved or dispersed in a suitable polymeric material, such that additional pores or channels are left after the material dissolves. A matrix device is generally diffusion limited as well, but with the channels or other internal geometry of the device also playing a role in releasing the agent to the fluid. The channels can be pre-existing channels or channels left behind by released agent or other soluble substances.

Erodible or degradable devices typically may have the active compounds physically immobilized in the polymer. The active compounds can be dissolved and/or dispersed throughout the polymeric material. The polymeric material may be hydrolytically degraded over time through hydrolysis of labile bonds, allowing the polymer to erode into the fluid, releasing the active agent into the fluid. Hydrophilic polymers have a generally faster rate of erosion relative to hydrophobic polymers. Hydrophobic polymers are believed to have almost purely surface diffusion of active agent, having erosion from the surface inwards. Hydrophilic polymers are believed to allow water to penetrate the surface of the polymer, allowing hydrolysis of labile bonds beneath the surface, which can lead to homogeneous or bulk erosion of polymer.

The pharmaceutical compositions can be included in a container, pack, or dispenser together with instructions for administration.

The pepducin approach according to the present invention allows the rich diversity of intracellular receptor structures to be exploited both for generation of new therapeutic agents and for delineation of the mechanisms of receptor-G protein coupling under in vivo conditions. The pepducins discovered by this strategy may also prove to be more selective to the extent that the pepducins primarily target the receptor rather than the G protein. In addition, many receptors have been identified by genomic and genetic approaches as being important in various diseases processes but have no known ligands—so-called orphan receptors. Pepducin agonists and antagonists can be generated which are tailored to these receptors, and may be useful in determining which signaling pathways are activated by the orphan receptor in the context of its native environment. Thus, in the post-genomic era, the pepducin approach may be widely applicable to the targeting of membrane proteins and may open up new experimental avenues in systems previously not amenable to traditional molecular techniques.

Example 1

Manufacture and Characterization of Pepducin Compositions

Synthesis by standard Fmoc solid phase synthetic methods and preparation of palmitoylated peptides was performed as previously described. Covic et al., PNAS 99:643-648 (2002). Palmitoylated peptides were purified to >95% purity by $C_{18}$ or $C_4$ reverse phase chromatography and dissolved in DMSO.

For human studies, whole blood was drawn from healthy volunteer donors with an 18 gauge needle into a 30 mL syringe containing 3 mL of 4% sodium citrate (0.4% v/v final). Gel-filtered human platelets were prepared as previously described. Hsu-Lin, et al., J. Biol. Chem. 259, 9121 (1984). Platelet counts were adjusted to $1.5 \times 10^5/\mu L$ in modified PIPES buffer and platelet aggregation was carried out in the presence of 2.5 mM $CaCl_2$ in final volumes of 250 µL. Platelet aggregation was measured by light scattering using a Chronolog 560VS/490-2D aggregometer. Cytosolic calcium measurements were performed on gel-filtered human platelets as previously described. Covic et al., Biochemistry 39, 5458 (2000). For mouse platelet studies, whole blood (0.5-1 mL/mouse) was collected from the inferior vena cava into heparinized syringes and pooled from 5 mice. Washed platelets were prepared by centrifugation of platelet-rich plasma containing 0.1 U/ml of apyrase/1 mM EDTA and aggregation studies conducted as previously described. Azam et al., Mol. Cell. Biol. 21, 2213 (2001).

Bleeding times were performed with 6-8 week-old adult male CF-1 mice anaesthetized with an intraperitoneal injection of xylazine (10 mg/kg) plus ketamine (50 mg/kg). The internal jugular vein was cannulated with a 0.28×1.52 mm gauge catheter and P1pal-12 (3 µmoles/L), P4pal-10 (3 µmoles/L) or vehicle alone (DMSO), was infused over 1 min in a total volume of 100 µL. Experiments were performed blind to injected substance. After 5 min, tails were amputated 2 mm from the tail tip. Tails were immersed in a beaker of phosphate-buffered saline maintained at 37° C. and bleeding was visually followed and timed. If bleeding restarted within 5 min, it was recorded as a re-bleed and taken to mark an unstable homeostasis event as previously described. Law et al., Nature 401, 808 (1999). Maximum bleeding time allowed was 10 min after which the tail was cauterized.

Mice were anaesthetized and then catheterized via jugular vein and injected with either vehicle alone (DMSO), or 0.3, 1 or 3 µmoles/L of P4pal-10 in 100 µL volumes over 1 min. After 5 min, systemic platelet activation was induced with a cocktail of 200 µM AYPGKF (SEQ ID NO:26) plus 5 µM epinephrine. After an additional 5 min following the AYPGKF (SEQ ID NO:26)/epinephrine infusion, blood was collected from the inferior vena cava into heparinized syringes. Blood was diluted two-fold into Tyrode's buffer containing 0.1 U apyrase/1 mM EDTA. Platelet count in whole blood was determined using a Coulter Counter.

Platelet aggregation is measured spectometrically, using an aggregometer such as an optical aggregometer, a whole blood aggregometer or an intracellular ionized calcium aggregometer. Platelet activation by degranulation is measured as an increase of cytoplasmic $Ca^{2+}$, or the appearance of cell surface markers such PAC-1 and CD62P.

$Ca^{2+}$ measurements were performed as described (Kuliopulos et al., Biochemistry 38, 4572-4585 (1999)). Intracellular $Ca^{2+}$ concentration was monitored as the ratio of fluorescence excitation intensity at 340/380 nm.

An i3 peptide, designated P1-i3-40, was constructed containing the adjacent transmembrane alpha-helical amino acids from the TM5 of PAR1. As a primary screen for biological activity, the ability of P1-i3-40 was tested for it's ability to stimulate platelet activation by monitoring intracellular $Ca^{2+}$. The composition of the P1 peptides are shown in FIG. 1.

Figure 1B:
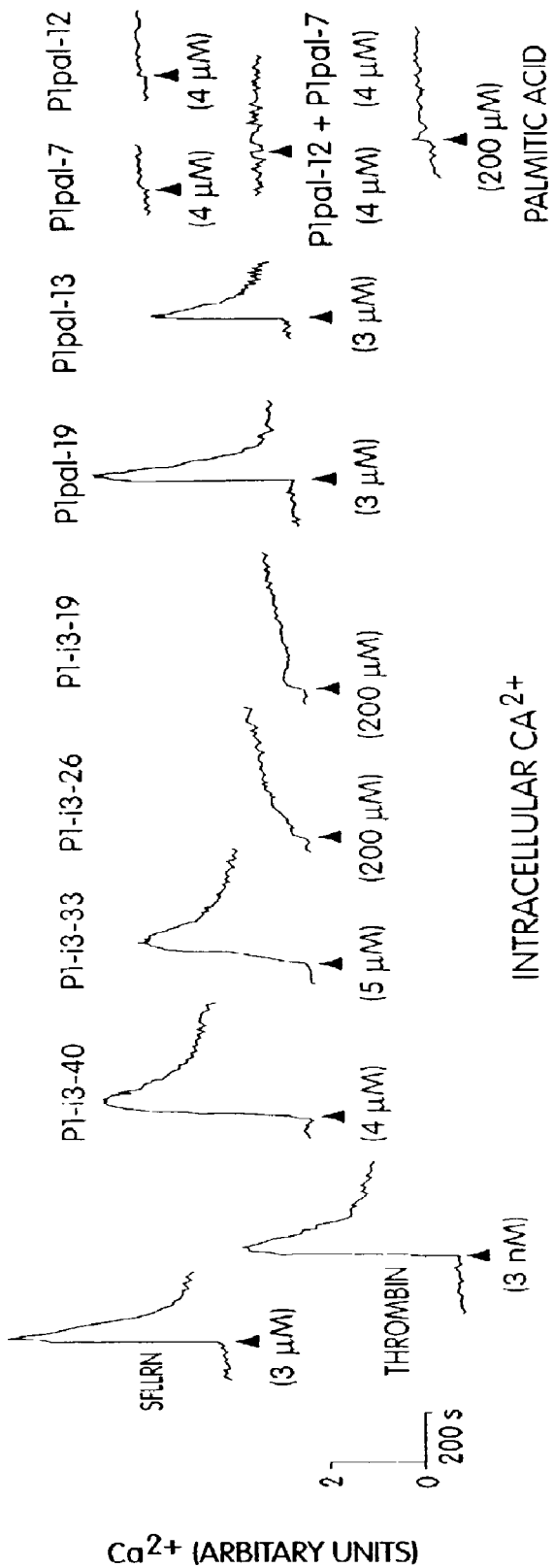
FIGS. 1B and 1C are line graphs of the fluorescence excitation intensity indicating calcium levels at 340/380 nm. Figures disclose "SFLLRN" as SEQ ID NO: 23.
Figure 1C:
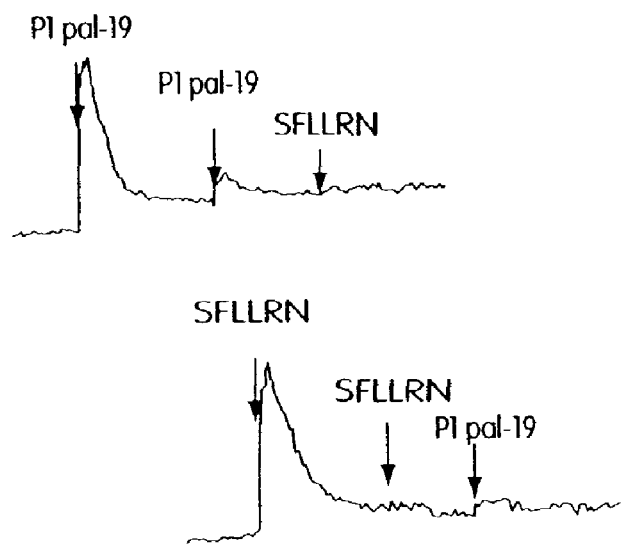

When added to platelets, the P1-i3-40 peptide causes a rapid intracellular $Ca^{2+}$ transient ($Ca^{2+i}$) that mimics the $Ca^{2+i}$ response generated by thrombin (FIG. 1B). The $Ca^{2+i}$ transient has no measurable lag phase (<5 s) and the maximum $Ca^{2+i}$ is saturable. A series of progressively truncated versions of P1-i3-40 were then made in order to determine whether the N-terminal hydrophobic region was required for activity. The P1-i3-19 peptide, which completely lacks hydrophobic N-terminal residues, causes little stimulation of $Ca^{2+}$ fluxes (FIG. 1B). The P1-i3-26 peptide with seven N-terminal hydrophobic residues, which would be expected to partition to only the outside leaflet of the lipid bilayer, gives a minor, unregulated $Ca^{2+i}$ response. In contrast, the P1-i3-33 peptide has similar potency to the P1-i3-40 peptide demonstrating that 14 hydrophobic amino acid residues confer full in vivo activity to the i3 intracellular loop. Studies with short membrane-translocating sequences have shown that 11-12 hydrophobic amino acid residues are sufficient to transfer proteins (15-120 kDa) into intact cells (Rojas et al., Nat. Biotech. 16, 370-375 (1998)) and tissues of mice (Schwarze et al., Science 285, 156-159 (1999)).

A palmitate lipid ($C_{16}H_{31}O$) was added to the GPCR moiety, and TM residues were removed in order to drastically reduce the size of the i3 peptides. Palmitoylated peptides were synthesized by standard Fmoc solid phase synthetic methods with C-terminal amides. Palmitic acid was dissolved in 50% N-methylpyrolidone/50% methylene chloride and coupled overnight to the deprotected N-terminal amine of the peptide. After cleavage from the resin, palmitoylated peptides were purified to >95% purity by C18 or C4 reverse phase chromatography in DMSO. The palmitoyl functionality is represented as Pal, and the construct $C_{15}H_{31}CONH$-Peptide-$NH_2$ is represented herein as Pal-Peptide.

As shown in FIG. 1B, the palmitoylated i3 loop peptide, P1pal-19 causes a rapid $Ca^{2+i}$ transient that is identical in profile to that caused by the extracellular PAR1 ligand, SFLLRN (SEQ ID NO:23). In addition, P1pal-19 fully activates platelet aggregation (FIG. 1D) with an EC50 of 8±3 micromolar. Individual aggregation traces of platelets stimulated with 10 Micromolar of indicated peptides or palmitic acid and platelet aggregation was monitored as % light transmittance of stirred platelets at 37° C. as described. Covic et al., Biochemistry 39, 5458-5467 (2000). P1pal-19 completely inhibits the subsequent $Ca^{2+i}$ response to 30 micromolar SFLLRN (SEQ ID NO:23) (FIG. 1C) due to desensitization of PAR1. Similarly, prestimulation with SFLLRN (SEQ ID NO:23) completely desensitizes the platelets to P1pal-19. Palmitic acid by itself has no effect on $Ca^{2+i}$ and platelet aggregation (FIG. 1B, D).

Figure 1D:
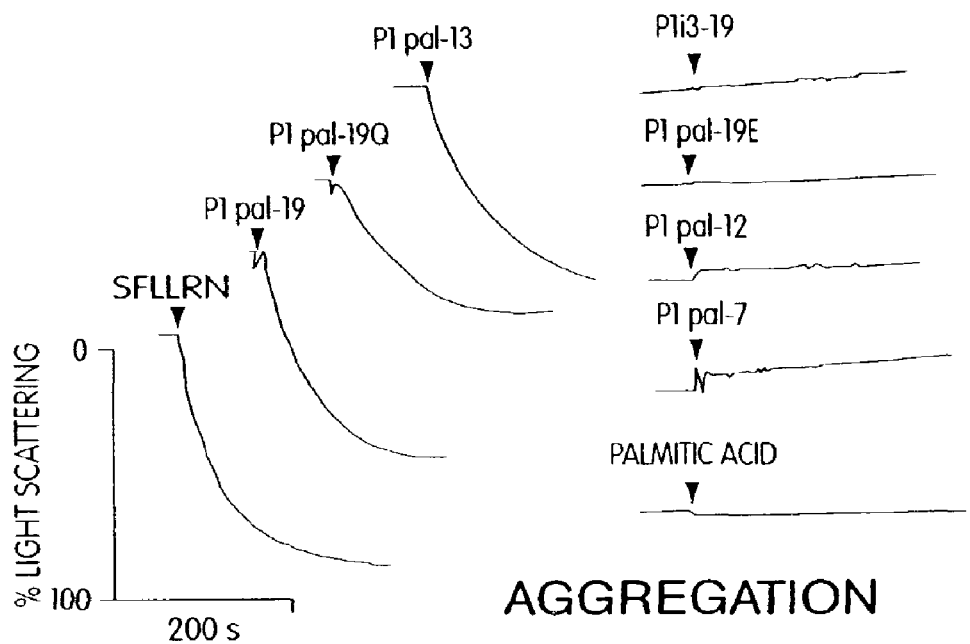
FIG. 1D is a line graph of light transmittance by platelets. Figure discloses "SFLLRN" as SEQ ID NO: 23.
Figure 1E:
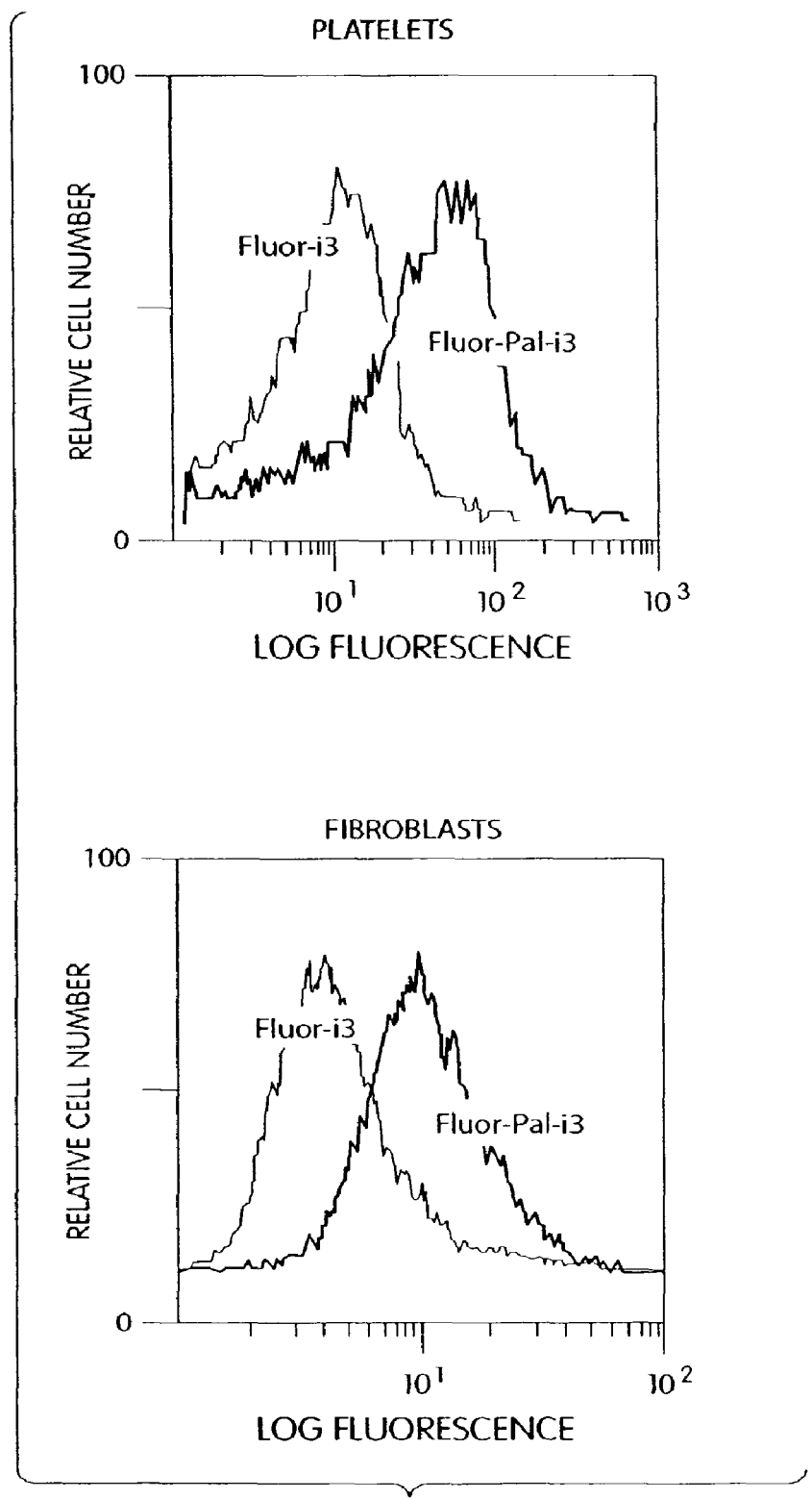
FIG. 1E are line graphs indicating flow cytometry of Rat1 fibroblasts.

To directly determine whether palmitoylation conferred cell-penetrating abilities, P1-i3-19 and P1pal-19 were labeled with fluorescein (Fluor) and incubated with platelets and PAR1-Rat1 fibroblasts. The cells were then treated with pronase to digest extracellularly bound peptides and analyzed by flow cytometry. Flow cytometry was conducted on platelets or Rat1 fibroblasts stably transfected with PAR1 (Ishii et al., J. Biol. Chem. 269, 1125-1130 (1994)) that were treated with fluorescein-labeled peptides, Fluor-Pal-i3 (Fluor-P1pal-19) or Fluor-i3 (Fluor-P1-i3-19) as indicated. Fluorescein was conjugated to the i3 peptides by incubating equimolar concentrations of peptide and fluorescein-5-EX-succinimidyl ester (Molecular Probes) for 2 h at 25° C. in DMF/5% triethylamine. The conjugated peptide products were purified from reactants using reverse-phase chromatography. The composition of the conjugated peptides was confirmed by mass spectrometry. Cells were incubated with 10 micromolar Fluor-Pal-i3 or Fluor-i3 for 2 min in PBS/0.1% fetal calf serum and then treated with 2 U pronase for 15 min at 37° C. and washed prior to flow cytometry. As shown in FIG. 1E, both platelets and fibroblasts remained strongly fluorescent when treated with Fluor-Pal-i3, as compared to the non-palmitoylated Fluor-i3. Other studies have shown that disruption of the cell membrane abrogates protection against pronase digestion only with Fluor-Pal-i3 and not Fluor-i3, thus confirming that the palmitoylated i3 peptide is membrane permeable.

Some pepducins remain attached to the cell membrane after penetration. A first step to understanding the intracellular liganding of these pepducins is to define the minimal molecular determinants of activation and the optimal position of the cell-penetrating anchor. This is accomplished by generating compositions according to Formula I:

$$A\text{-}X\text{-}B\text{-}Y_n \quad (1),$$

wherein A is a cell-penetrating (anchor) moiety, X is a linking moiety, B is an isolated fragment of a G-protein coupled receptor (GPCR), Y is a hydrophobic moiety, such as an aromatic compound (e.g., halogen-substituted biphenyl), a peptide or a lipid, and n is zero or one. For example, X can be a covalent bond, polyglycine, polyarginine, and a mixed sequence hydrophobic peptide. Varying the length of the linker allows one to keep the location of the cell-penetrating (A) attachment fixed relative to activating and binding determinants in the GPCR fragment (B). In some compositions, a cell-penetrating moiety is linked to an amino acid in the GPCR fragment (B). For example, the cell-penetrating moiety can be a lipidated Cysteine.

The location of a Cys-lipid moiety (within B) is moved (by varying the length of the linker) in the context of Pal13, with or without a N-terminal (Y) group. Dual lipidation (A and Y are both lipids) or movement of the site of lipid attachment within B may enhance, block, or not effect pepducin activity. Lipidation of cysteine thiols is done with N-MPB-PE (1,2-dipalmitoyl-sn-glycero-3-phosphoethanolamine-N-[4-(p-maleimidophenyl)-butyramide) by mixing 2.5 mM peptide and 5 mM N-MPB-PE (Avanti Polar Lipids) in 6% triethylamine/94% dimethylformamide and incubating at ambient temperature for 2 h.

Example 2

Assessment of the Ability of Pepducins to Activate PAR1 in a Recombinant System

Seven GPCRs were tested (PAR1, PAR2, PAR4, CCKA, CCKB, SSTR2, and MC4) for their ability to be activated or inhibited by their cognate pepducin. Full antagonist activity was demonstrated for PAR1, PAR2 (FIG. 4D), PAR4 (FIGS. 4C-D), and SSTR2 'wild-type' pepducins with their cognate receptors with IC50 values of 1 to 3 micromolar, as summarized in Table 2. Of these GPCRs, PAR4 is newly-discovered (Kahn et. al., Nature (London) 394:690-694 (1998); Xu et al., Proc. Natl. Acad. Sci. (USA) 95, 6642 (1998)). PAR4 was selected due to an interest in developing reagents suitable for exploring the unique ability of PAR4 to cause prolonged $Ca^{2+}$ transients and irreversible platelet aggregation (Covic et al., (2000) Biochemistry 39, 5458). To date, the best extracellular ligands to PAR4 bind with millimolar or high-micromolar affinity and PAR4 inhibitors have not been reported. In FIG. 4, the anti-PAR4 pepducin, P4pal-15, inhibits PAR4 and not PAR1, whereas the converse is true for the anti-PAR1 pepducin, P1pal-12. Thus, P4pal-15 is the first described high-potency anti-PAR4 compound ($IC_{50}$=0.6 micromolar in platelets) and is currently being used to help delineate the role of PAR4 in the vascular biology of mice. Covic et al., Nature Medicine in press (2002).

Figure 2A:
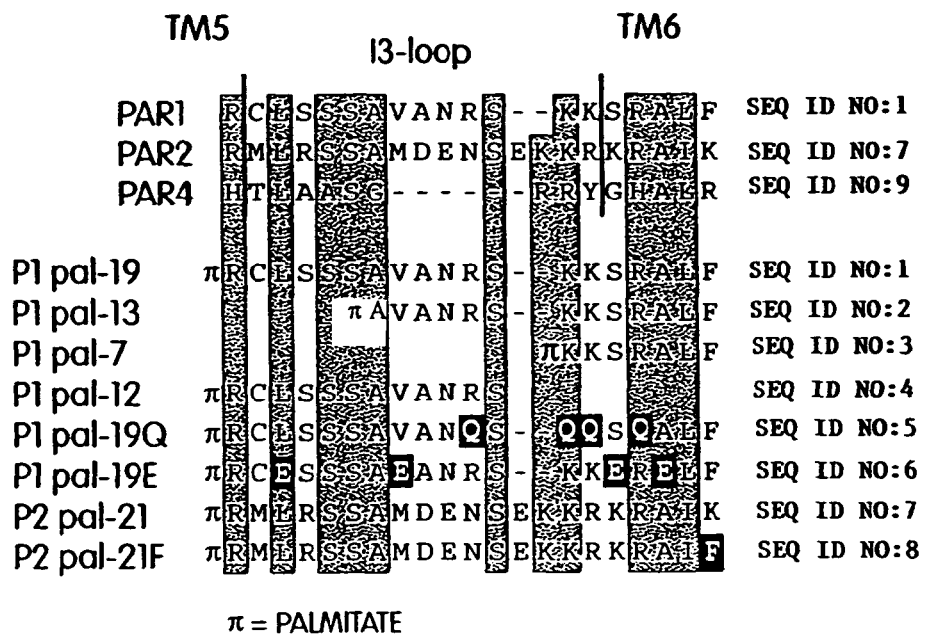
FIG. 2A is a table illustrating an alignment of amino acid sequences.
Figure 2B:
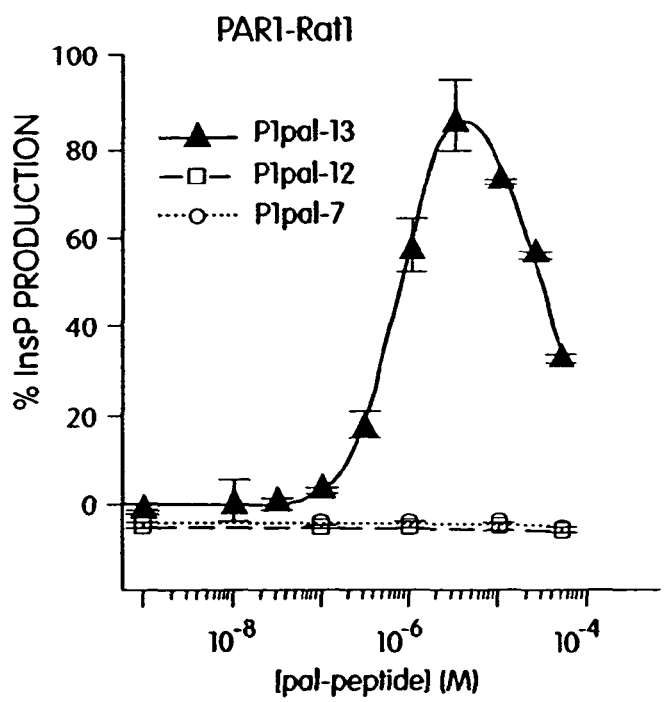
FIGS. 2B-D are line graphs demonstrating the effect of various peptides on PLC-β activity as measured by inositol phosphate formation.
Figure 2C:
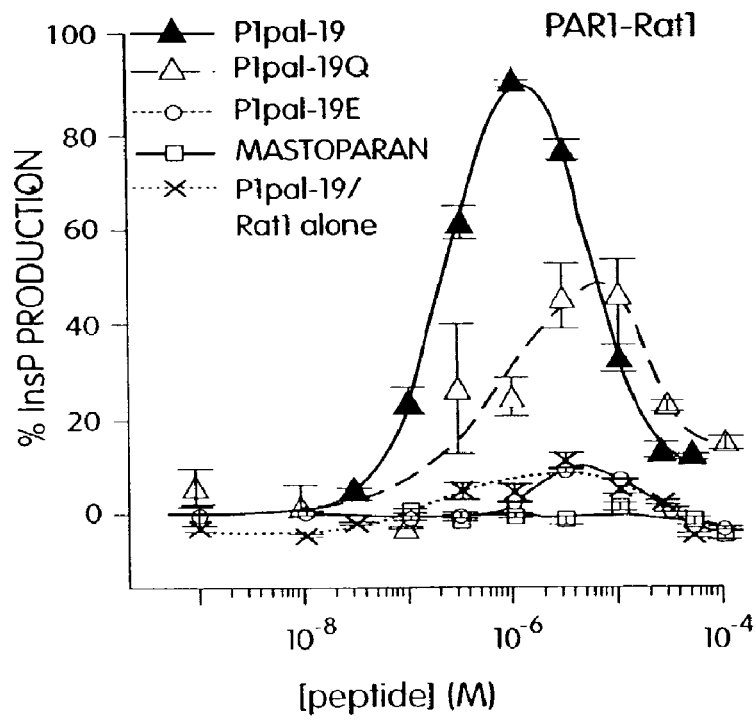
Figure 2D:
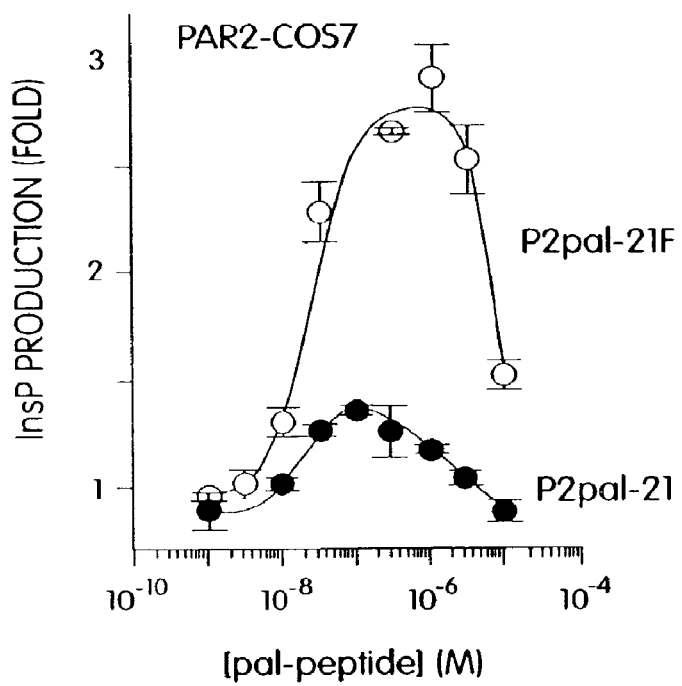

Six of the newly tested wild-type pepducins were partial agonists for their own GPCR with maximal efficacies of ~12-35% (Table 2, FIG. 7) including the P2pal-21 pepducin (FIG. 2D).

Figure 2E:
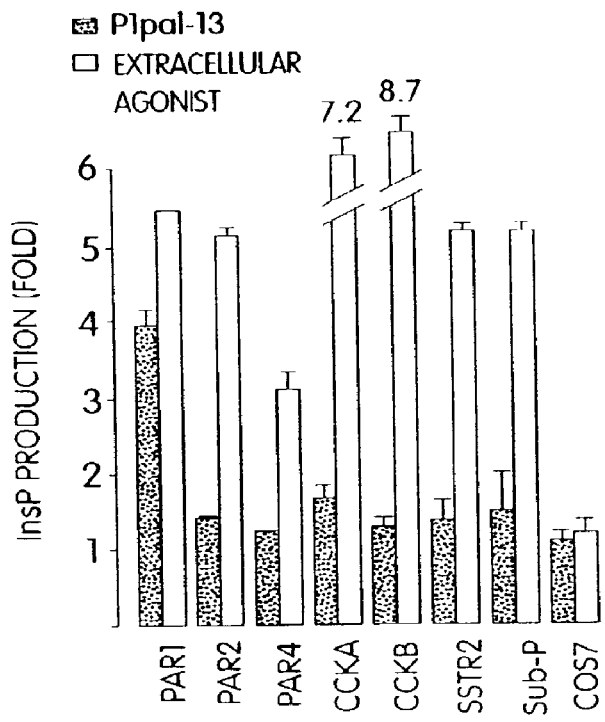
FIGS. 2E-G are bar graphs demonstrating the penetrating ability of P1pal-19, P1pal-i3, P2pal-21, and P2pal21F peptides on COS7 cells transfected with various receptors, as measured by on PLC-β activity (measured by inositol phosphate formation).
Figure 2F:
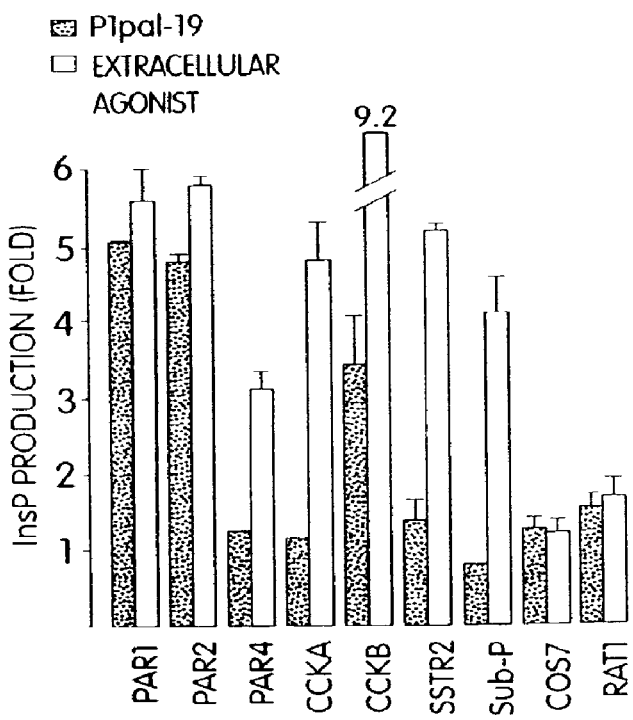
Figure 2G:
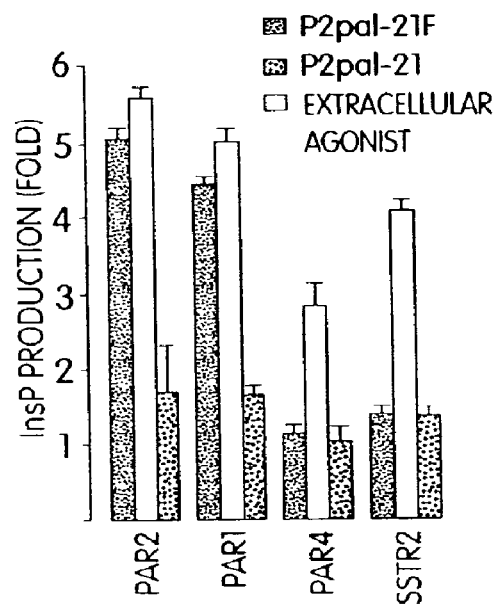

However, the PAR1 pepducin, P1pal-19, robustly activates PAR2 (FIG. 2F), indicating that selective introduction of mutations into P2pal-21 might create a full agonist for PAR2. An alignment of the i3 loops of PAR1 and PAR2 (FIG. 2A) revealed several sequence differences. A point mutation of the C-terminal lysine to phenylalanine imparted full agonist activity to the PAR2 pepducin P2pal-21F (FIG. 2D). This pepducin also activated PAR1 but not PAR4 nor SSTR2 (FIG. 2G). Similar C-terminal point mutations of Lys/Arg to Phe conferred partial agonist activity to the pepducins of SSTR2, and CCKA and improved the potency of the CCKB pepducin by 15-fold (Table 2). To summarize, from a screen of seven diverse GPCRs, full agonists for PAR1 and PAR2, partial agonists for MC4, SSTR2, CCKA, and CCKB, and full antagonists for PAR1, PAR2, PAR4 and SSTR2 (Table 2, FIG. 7) have been demonstrated. Thus, the pepducin inhibitors and agonists of the invention are applicable to a broad range of GPCRs which can couple to Gq, Gi, Gs, and G12/13.

The GPCR moiety of the pepducins of the present invention are derived from any cells of a human being or other organism (e.g., guinea pig, rat, mouse, chicken, rabbit, pig, sheep, cattle, monkey, virus, fungi, insects, plants, bacteria, etc.), for example, splenic cell, nerve cell, glia cell, beta cell of pancreas, marrow cell, mesangial cell, Langerhans' cell, epidermic cell, epithelial cell, endothelial cell, fibroblast, fibrocyte, muscular cell, fat cell, immunocyte (e.g., macrophage, T cell, B cell, natural killer cell, mast cell, neutrophil, basophil, eosinophilic leukocyte, monocyte, etc.), megakaryocyte, synovial cell, chondrocyte, osteocyte, osteoblast, osteoclast, mammary gland cell, hepatocyte, or interstitial cells or precursor cells, stem cells or cancer cells thereof and the like; and any tissues containing such cells, for example, brain, various parts of the brain (e.g., olfactory bulb, amygdala, cerebral basal ganglia, hippocampus, thalamus, hypothalamus, substhanlamic nucleus, cerebral cortex, medulla, cerebellum, occipital pole, frontal lobe, putamen, caudate nucleus, corpus callosum, substantia nigra), spinal cord, pituitary, stomach, pancreas, kidney, liver, genital organs, thyroid gland, gallbladder, bone marrow, adrenal gland, skin, muscle, lung, digestive tract, blood vessel, heart, thymus, spleen, submandibular gland, peripheral blood, peripheral blood leukocyte, intestinal tract, prostate, testicle, testis, ovarium, placenta, uterus, bone, joint, small intestine, large intestine, skeletal muscle and the like, in particular, brain and various parts of the brain.

Cell-penetrating ability of the pepducins was evaluated as follows. Since PAR1 couples to both Gq and Gi(beta/gamma) to stimulate phospholipase C-beta (PLC-beta) (Hung et al., J. Clin. Invest. 89, 1350-1353 (1992)) inositol phosphate (InsP) production in Rat1 fibroblasts expressing human PAR1. Accumulation of [3H]-inositol phosphates was measured in the presence of 20 mM LiCl. Cells were split into 12 well plates at 200,000 cells/well. [3H]-labeled myoinositol (2 μCi/mL) was added to cells 24 h prior to the experiment. Wells were rinsed twice with 2 mL DME containing 10 mM HEPES buffer, pH 7.3, then twice with 2 mL PBS containing 20 mM LiCl. Cells were stimulated with agonist or the specified concentrations of i3-loop pepducin for 30 min and then extracted with cold methanol and chloroform. Extracts were loaded onto columns containing 1 mL anion-exchange resin AGI X8, formate form, 100-200 mesh size (Bio-Rad Laboratories, Cambridge, Mass.). After loading, columns were washed twice with 10 mL $H_2O$ and twice with 10 mL 60 mM ammonium formate/5 mM Borax. Column fractions were eluted with 4 mL 2 M ammonium formate/0.1 M formic acid into vials containing 7.5 mL scintillation cocktail and counted. The mean of duplicate or triplicate determinations was expressed as fold-stimulation above non-stimulated cells. The biphasic pepducin data was fit to a two-site equation with one activating site (EC50) and one inhibitory site (IC50) $y=(100/(1+(([peptide]/EC50)-n1)))+(100/(1+(([peptide]/IC50)-n2)))-n3$ by non-linear regression analysis using Kaleidagraph 3.05, where n1 and n2 are hill coefficients for the activating and inhibitory phases, respectively, and n3 is the delta maximum amplitude.

PAR1-Rat1 cells or PAR2-COS7 cells were challenged with 1 nM to 10-100 μM i3 peptide or mastoparan (INLKA-LAALAKKIL) (SEQ ID NO:24). PLC-beta activity was determined by measuring total [3H]-inositol phosphate (InsP) formation. As shown in FIGS. 2B and C, P1pal-19, and P1pal-i3 which lacks the N-terminal six residues of P1pal-19, stimulate InsP production with EC50 values of 180±20 nM and 700±50 nM, respectively, and with similar efficacies as the natural agonist thrombin. In FIGS. 2B and 2C, PLC-β activity was converted to percent of the full response relative to 0.1 nM thrombin (100%) and plotted as a function of peptide concentration using a two-site equation that fit the biphasic activation and inhibition profiles. The full PAR1 thrombin responses for individual experiments were 7.6-fold for P1pal-i3, 9.4-fold for P1pal-12 and P1pal-7, 12.4-fold for P1pal-19 and P1pal-19/Rat1 alone, 18-fold for P1pal-19Q, 12.4-fold for P1pal-19E and 9.5-fold for the mastoparan experiment. The minor stimulation of untransfected Rat1 cells (Rat1 alone) by P1pal-19 in C can be attributed to the endogenous rat PAR1 present in these fibroblasts since addition of SFLLRN (SEQ ID NO:23) causes similar stimulation in these untransfected cells (FIG. 2F, 'RAT1').

Receptor stimulation of PLC-β was determined by measuring total [3H]-inositol phosphate (InsP) formation in Rat1 cells stably expressing PAR1 or in COS7 cells transiently expressing PAR2, PAR4, SSTR2, CCKA, or CCKB. Antagonist assays were conducted as in FIG. 4D: PAR1, PAR2, PAR4, or SSTR2-expressing cells were pre-treated with their cognate pepducins (10 nM-50 μM) for 5 min, and then stimulated with extracellular agonists 0.1 nM thrombin, 100 μM SLIGKV (SEQ ID NO:17), 10 nM thrombin, or 1 μM AGCK-NFFWKTFTSC (SEQ ID NO:18), respectively. In agonist assays, PAR1, PAR2, PAR4, SSTR2, CCKA or CCKB-expressing fibroblasts were stimulated with their cognate pepducins (1 nM-50 μM) for 30 min and InsP production measured. The biphasic pepducin data (see FIGS. 2B-D) was fit to a two-site equation, with an $EC_{50}$ for the activating phase and $IC_{50}$ for the inhibitory phase. Percent efficacy was calculated relative to the full (100%) response to extracellular agonist as above (300 nM CCK-8 for CCKA and CCKB).

ing by the cell-penetrating peptides requires the presence of receptor. In addition, positively charged residues in the C-terminal region of the i3 loop peptides previously shown to be essential for activation of G proteins (Okamoto et al., Cell 67, 723-730 (1991)) are not necessary for activity of these mem-

TABLE 2

Agonist and Antagonist Activity of Pepducins for their Cognate Receptors Expressed in Fibroblasts.

| Receptor | Pepducin | Sequence | SEQ ID NO | Antagonist $IC_{50}$ (μM) | $EC_{50}$ (μM) | Agonist $IC_{50}$ (μM) | Efficacy (%) |
|---|---|---|---|---|---|---|---|
| PAR 1 | P1pal-19 | Pal-RCLSSSAVANRSKKSRALF | 1 | — | 0.18 ± 0.02 | 6.5 ± 1.0 | 90 ± 2 |
|  | P1pal-13 | Pal-AVANRSKKSRALF | 2 | — | 0.70 ± 0.05 | 32 ± 5 | 60-88 |
|  | P1pal-7 | Pal-KKSRALF | 3 | 1.2 ± 0.1 | — | — | — |
|  | P1pal-12 | Pal-RCLSSSAVANRS | 4 | 5.0 ± 0.1 | — | — | — |
|  | P1pal-19Q | Pal-RCLSSSAVANQSQQSQALF | 5 | — | 0.65 ± 0.1 | 30 ± 2 | 46 ± 8 |
|  | P1pal-19E | Pal-RCESSSAEANRSKKERELF | 6 | >50 | 2.5 ± 0.5 | 80 ± 5 | 11 ± 1 |
| PAR2 | P2pal-21 | Pal-RMLRSSAMDENSEKKRKRAIK | 7 | 1.0 ± 0.5 | 0.018 ± 0.002 | 1.0 ± 0.2 | 18 ± 2 |
|  | P2pal-21F | Pal-RMLRSSAMDENSEKKRKRAIF | 8 | — | 0.025 ± 0.003 | 7 ± 1 | 95 ± 6 |
| PAR4 | P4pal10 | Pal-SGRRYGHALR | 29 |  |  |  |  |
|  | P4pal15 | Pal-HTLAASGRRYGHALR | 9 | 3.0 ± 1.0 | — | — | — |
|  | P4pal15F | Pal-HTLAASGRRYGHALF | 10 | >2 | - | - | - |
| SSTR2 | S2pal-23 | Pal-KVRSSGIRVGSSKRKKKSEKKVTK | 11 | 2.0 ± 1.0 | — | — | — |
|  | S2pal-23F | Pal-KVRSSGIRVGSSKRKKKSEKKVTF | 12 | 3.0 ± 1.0 | 0.1 ± 0.05 | 0.5 ± 0.3 | 15 ± 4 |
| CCKA | Apal-19 | Pal-RIRSNSSAANLMAKKRVIR | 13 | NT | — | — | — |
|  | Apal-19F | Pal-RIRSNSSAANLMAKKRVIEF | 14 | NT | 0.2 ± 0.1 | 2 ± 1 | <10 |
| CCKB | Bpal-18 | Pal-SGSRPTQAKLLAKKRVVR | 15 | NT | 1.5 ± 0.5 | 10 ± 2 | 12 ± 3 |
|  | Bpal-18F | Pal-SGSRPTQAKLLAKKRVVF | 16 | NT | 0.10 ± 0.05 | 1.0 ± 0.5 | 13 ± 2 |

NT = not tested.

The activation curves of PAR1 are biphasic with a steep activating phase followed by a steep inhibitory phase. Splitting the P1pal-19 agonist into C-terminal P1pal-7 and corresponding N-terminal P1pal-12 peptides results in loss of stimulatory activity in platelets or PAR1-Rat1 cells when added separately (FIGS. 1B, 1D, 2B) or together (FIG. 1B). Therefore, in order to have agonist activity, C-terminal PAR1 pepducin residues 301-313 must be contiguous. COS7 cells were transiently transfected with the human receptors PAR 1, PAR2, PAR4, cholecystokinin A (CCKA), cholecystokinin B (CCKB), substance P (Sub-P), or rat somatostatin receptor (SSTR2). Transfected cells were challenged with a range of concentrations (0.1-10 micromolar) of P1pal-19, P1pal-i3, or P2pal-21 and the highest stimulation of the individual receptors is reported as a black column. The extracellular agonists used to define maximum stimulation for each receptor (open column) were 10 nM thrombin for PAR1, 100 micromolar SLIGKV (SEQ ID NO: 17) for PAR2, 100 nM thrombin for PAR4, 300 nM CCK-8 for CCKA and CCKB, 1 micromolar AGCKNFFWKTFTSC (SEQ ID NO:18) for SSTR2, and 1.5 micromolar RPKPQQFFGLM (SEQ ID NO:25) for Sub-P. Covic et al., PNAS 99, 643 (2002).

Significantly, neither P1pal-i3 nor P1pal-19 stimulate InsP (approximately 11%) in the absence of the PAR1 receptor in COS7 cells (FIG. 2E, F) or in Rat1 fibroblasts (FIG. 2C, F). These results demonstrate that activation of G protein signalbrane-tethered agonists. Substitution of the positive charges results in only a 2-fold loss in efficacy of the P1pal-19Q peptide (FIG. 2A) in platelet aggregation (FIG. 1D) or stimulation of InsP in PAR1-Rat1 cells (FIG. 2C). Moreover, the amphipathic wasp venom peptide mastoparan, which is a receptor-independent activator of Gi/o (Higashjima et al., J. Biol. Chem. 265, 14176-14186 (1990)), did not stimulate InsP production in the PAR1-Rat1 cells (FIG. 2C). Thus, the peptides are not simply acting as positively charged amphipathic helixes to activate G protein signaling in an uncontrolled manner. In contrast, mutation of the conserved, more hydrophobic residues in the P1pal-19E peptide (FIG. 2A) results in ~90% loss of agonist activity (FIG. 1D, 2C).

Example 3

Specificity of Pepducins for Other GPCRs

For these PAR1-derived i3 peptides to be useful as in vivo reagents, it was important to determine the specificity of the peptides for other GPCRs. P1pal-19 and P1pal-i3 were tested for agonist activity against an array of six other GPCRs: PAR2, PAR4, cholecystokinin A and B (CCKA and CCKB), somatostatin (SSTR2), and substance P (Sub-P). COST cells were transiently transfected with each receptor and InsP production measured. P1pal-i3 is selective for PAR1 and did not activate the other six GPCRs including PAR2 (FIG. 2E).

P1pal-19 can fully activate the highly homologous PAR2 receptor and stimulates CCKB to about 30% of its maximal activity, but does not activate PAR4, CCKA, SSTR2, nor Sub-P (FIG. 2F). These data indicate that the P1pal-13 exhibits complementarity of binding to PAR1 and is highly selective. Inclusion of the six N-terminal amino acids of the i3 loop in P1pal-19 results in less selectivity.

Example 4

Construction of Agonists for GPCRs Other than PAR1

It was found in some cases that lipidated peptides, based on their corresponding wild-type i3 sequences, were partial agonists with efficacies of 40% for MC4 (FIG. 7), 18% for PAR2 (P2pal-21, FIG. 2D) and 12% for CCKB, and no agonist activity was observed for the i3 peptides of PAR4, SSTR2 and CCKA (Table 2). However, as previously demonstrated, the P1pal-19 PAR1 peptide was able to robustly activate PAR2 (FIG. 2F) indicating that selective mutation of P2pal-21 might create a full agonist for PAR2. An alignment of the i3 loops of PAR1 and PAR2 (FIG. 2A: which shows the alignment of the third intracellular (i3) loops and adjacent transmembrane regions (TM5 and TM6) for PAR1, PAR2 and PAR4 receptors with palmitoylated peptides for PAR1 and PAR2) revealed several sequence differences. Quite strikingly, mutation of the C-terminal Lys to Phe converts the PAR2 peptide, P2pal-21F, into a potent (EC50=25 nM), full agonist of PAR2 with biphasic properties (FIG. 2D). P2pal-21F also activated PAR1 but not PAR4 nor SSTR2 (FIG. 2G). Similar C-terminal Lys/Arg to Phe point mutations of the SSTR2 and CCKA peptides conferred partial agonist activity with their cognate receptors and improved the potency of the CCKB peptide by 15-fold.

These data suggest that the peptide must be tethered or embedded in a lipophilic environment at both termini to exhibit high agonist activity.

To distinguish between indirect versus direct activation of the G protein by the pepducins, a point mutation was introduced at position S309 located in the C-terminus of the i3 loop/N-terminus of TM6 of PAR1. This perimembranous region has been shown to be important for the fidelity of G protein coupling for many receptors. Cotecchia et al., J. Biol. Chem. 267, 1633-1639 (1992); Kostenis et al., Biochemistry 36, 1487-1495 (1997); Kjelsberg, et al., J. Biol. Chem. 267, 1430-1433 (1992), and comes into direct contact with the critical DRY residues of TM3. Palczewski et al., Science 289, 739-45 (2000). A S309P mutant was constructed and transiently expressed in COS7 cells to the same level as wild type PAR1. COS7 cells were transiently transfected with wild-type (WT), S309P or delta377 PAR1 (Kuliopulos et al., Biochemistry 38, 4572-4585 (1999)) receptors. Cells were challenged with P1pal-19, SFLLRN (SEQ ID NO:23), or thrombin and PLC-beta activity determined by measuring total [3H]-inositol phosphate formation relative to 100% stimulation (9.6-fold) of WT PAR1 with 0.1 nM thrombin. The apparent inhibition of PAR1 by very high concentrations of thrombin in B is caused by persistent interactions of thrombin to a hirudin-like sequence (K51YEPF55) located in the e1 exodomain of PAR1 (Hung et al., J. Clin. Invest. 89:1350-1353 (1992)). High amounts of thrombin can remain bound to the thrombin-cleaved PAR1 exodomain (Jacques, et al., J. Biol. Chem. 275, 40671-40678 (2000)) and inhibit intramolecular ligandiing by the tethered SFLLRN (SEQ ID NO:23).

Figure 3A:
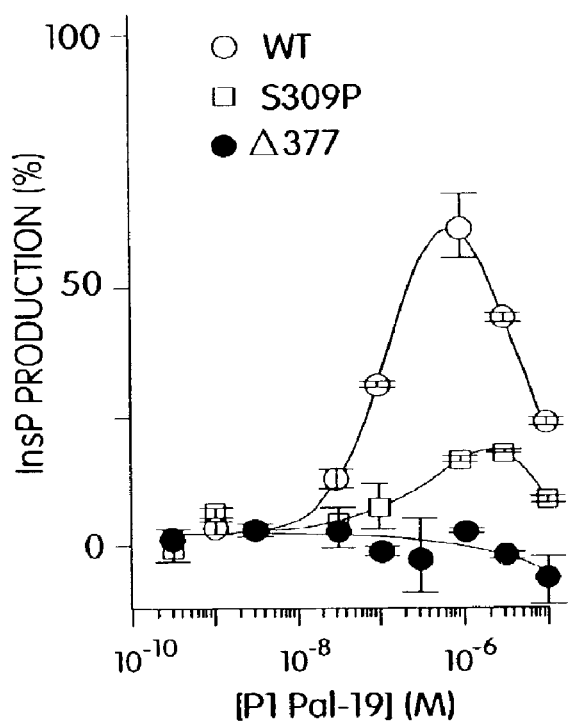
FIGS. 3A-3C are line graphs demonstrating the penetration of pepducin P1pal-19, thrombin, and SFLLRN (SEQ ID NO:23) to activate wild-type (WT) and mutant (C— tail deleted delta377, and S309P) PAR1s, as monitored by PLC-beta-dependent inositol phosphate formation.
Figure 3B:
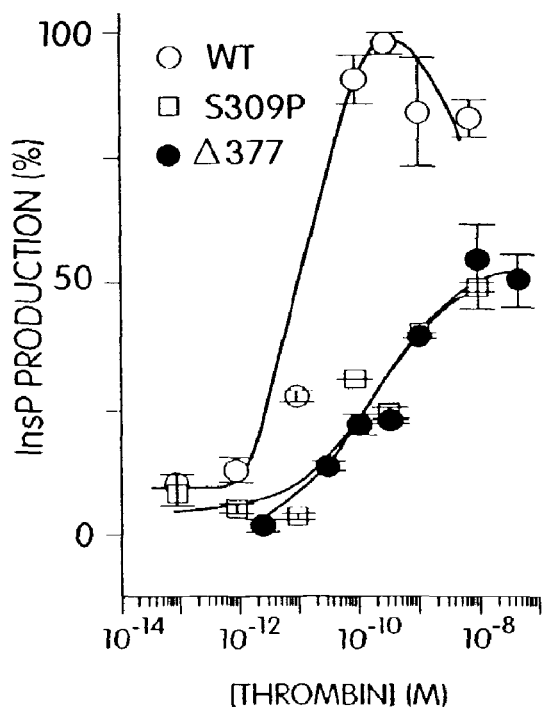

The S309P mutant is deficient in thrombin- and SFLLRN-dependent (SEQ ID NO:23) stimulation of InsP with 17- and 28-fold loss of potency, and 1.6- and 3.3-fold loss of efficacy, respectively (FIG. 3B, C). P1pal-19 also stimulates the S309P mutant with parallel losses in potency (13-fold) and efficacy (4.3-fold) relative to its effects on wild type PAR1 (FIG. 3A). Since P1pal-19 did not correct the signaling defect of the S309P mutation, this indicates that the crucial C-terminal portion of the i3 region in the intact receptor exerts dominant effects in coupling to G protein over that of the exogenous pepducin.

Example 5

Determination of GPCR Regions that Interact with the Pepducins

To define the region(s) of the receptor that might directly contact the i3-pepducin, the entire C-terminal i4 domain of PAR1 was deleted (delta377). The X-ray structure of rhodopsin (Palczewski et al., Science 289, 739-45 (2000)) indicates that the i3 loop may contact the N-terminal region of alpha-helix 8 and residues to the C-terminal side of the Cys-palmitoyl moieties within the i4 C-tail. As shown in FIGS. 3B and C, the delta377 mutant is defective in stimulating PLC-beta in response to thrombin and SFLLRN (SEQ ID NO:23). Efficacy is reduced by 2-3 fold for the two PAR1 agonists and potency is shifted 22-fold for thrombin and ~30-fold for SFLLRN (SEQ ID NO:23). In contrast, the P1pal-19 pepducin gives effectively no stimulation of PLC-beta in the presence of the delta377 PAR1 mutant (FIG. 3A). These data demonstrate that the C-tail of PAR1 is required for P1pal-19 to activate G-protein and that the C-tail may provide a binding surface for the pepducin agonists.

Example 6

Pepducins that Lack Agonist Activity Still Block GPCR Protein Signaling

Figure 3C:
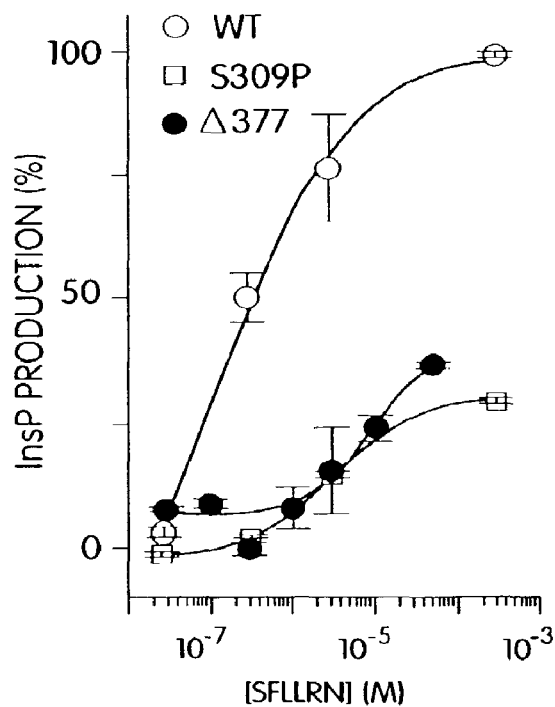

Human platelets were a convenient, biologically-relevant, system to test the potency and selectivity of anti-PAR1 and anti-PAR4 pepducins since platelets possess both PAR1 and PAR4 thrombin receptors with unique Ca2+ signaling profiles. The PAR1 peptide, P1pal12, was found to completely block PAR1 signaling. Platelet Ca2+ measurements were performed as in Example 1. Platelets were pre-treated with 3 µM P1pal-12 (open arrow-head) or P4pal-15 (Pal-HTLAAS-GRRYGHALR (SEQ ID NO:9); closed arrow-head), and then stimulated with 3 Micromolar SFLLRN (SEQ ID NO:23) or 200 Micromolar AYPGKF (SEQ ID NO:26) as indicated. As shown in FIGS. 4A-C, 3 micromolar P1pal-12 effectively inhibits PAR1 activation of human platelets by SFLLRN (SEQ ID NO:23), but does not block PAR4 activation by AYPGKF (SEQ ID NO:26) (FIG. 4A). Moreover, a pepducin corresponding to the full-length i3 loop of PAR4, P4pal-15, had no agonist activity but was able to fully antagonize PAR4 signaling.

Platelets were then preincubated with either 3 Micromolar P1pal-12 or 3 Micromolar P4pal-15 for 1 min and then challenged with 3 Micromolar SFLLRN (SEQ ID NO:23) or 200 Micromolar AYPGKF (SEQ ID NO:26) and platelet aggregation monitored as in FIG. 1D. Full platelet aggregation traces are also shown for the same amounts of SFLLRN (SEQ ID NO:23) or AYPGKF (SEQ ID NO:26) in the absence (−) of inhibitors. Platelets were pre-treated for 1 min with 0.01-5 Micromolar P1pal-12 or P4pal-15 and challenged with 3 Micromolar SFLLRN (SEQ ID NO:23) or 200 Micromolar AYPGKF (SEQ ID NO:26), respectively. As shown in FIG.

4A, 3 micromolar P4pal-15 blocked AYPGKF (SEQ ID NO:26) activation of PAR4 without affecting SFLLRN (SEQ ID NO:23) activation of PAR1 and is an effective inhibitor of platelet aggregation (FIG. 4B, C). Thus, P4pal-15 is the first described high-potency anti-PAR4 compound (IC50=0.6 micromolar in platelets) and is currently being used to help delineate the role of PAR4 in the vascular biology of mice.

PAR1, PAR4, and PAR2-expressing fibroblasts were pretreated with 0.03-100 micromolar P1pal-12, P4pal-15, or P2pal-21 for 5 min, and then challenged with extracellular agonists 0.1 nM thrombin, 10 nM thrombin, or 100 micromolar SLIGKV (SEQ ID NO:17), respectively. Percent InsP inhibition is calculated relative to the full extracellular agonist-stimulated response: 5.2-fold for P1pal-12, 3.1-fold for P4pal-15 and 3.1-fold for P2pal-21. Both anti-PAR1 and anti-PAR4 pepducins are also able to block signaling to PLC-beta in fibroblasts expressing PAR1 or PAR4, respectively (FIG. 4D). Lastly, the PAR2 pepducin, P2pal-21, which is a partial agonist for PAR2 (FIG. 2D), is also able to completely block PAR2 signaling in fibroblasts (FIG. 4D).

Example 7

Ligand Binding Site Peptides with C-Terminal Lipid Tethers Interfere with Receptor Liganding Peptides from the first extracellular domain (e1) PAR1 which have a C-terminal cysteine-lipid for generation of extracellular, membrane-tethered, antagonists of ligand binding to PAR1 are described. In some cases, N-terminal attachment of lipid or hydrophobic tethers to the receptor peptide fragments may lead to loss of activity or may not be optimally placed for targeting the receptor, G protein, or for blocking extracellular liganding. Thus, another embodiment of this technology is attaching lipid tethers to cysteine residues or other derivatizable groups (i.e., —SH, —NH2, —OH) in the receptor fragment that are strategically located at points likely to come into membrane contact. Internal cysteines will be mutated to serine as necessary to avoid spurious derivatization. Based on molecular modeling, some of the peptides will be lipidated at internal, N- and/or C-terminal positions. Glycine (n=1-5) or similar molecular spacers could be placed between sites of lipidation and peptide if necessary for more efficient membrane anchoring or targeting. Dual lipidation may increase effective molarity and reduce entropic contributions at the receptor-effector or receptor-ligand interface.

Figure 8A:
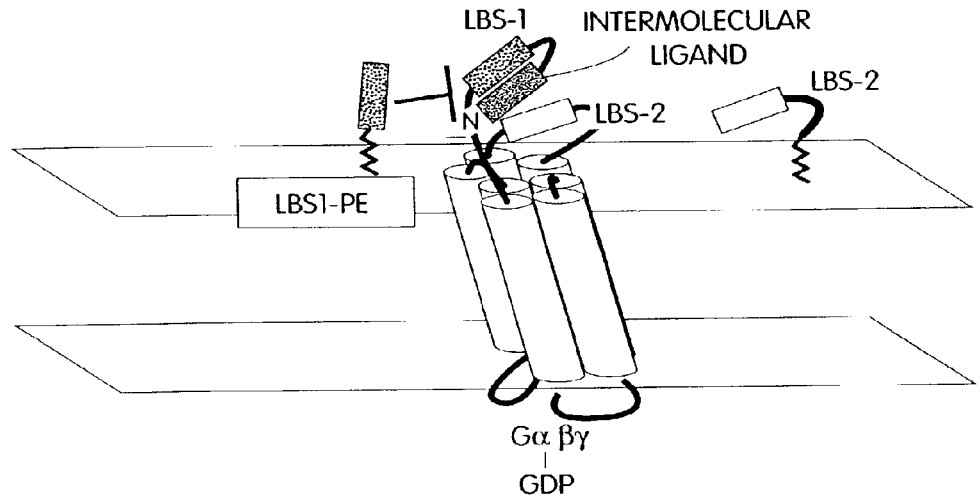
FIGS. 8A and B are schematic representations of LBS-1 interference of PAR-1 activation and molecular liganding.
Figure 8B:
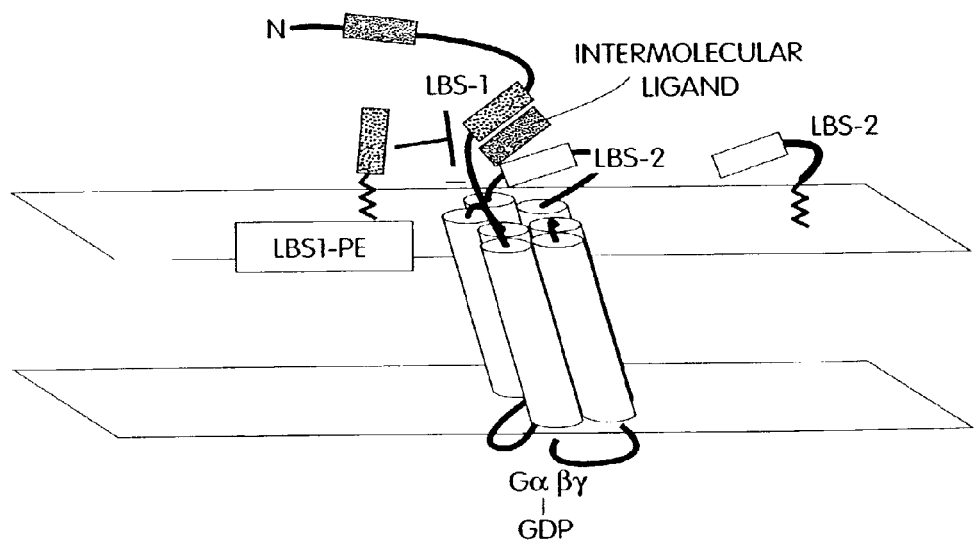

As an example, using NMR structural analysis, a region on the extracellular surface of PAR1 which forms part of the ligand binding site for PAR1 was identified. This region is comprised of receptor residues P85AFIS89 and is termed ligand binding site-1 (LBS-1). Mutation of this region on PAR1 results in severe defects in receptor activation by intermolecular ligand (i.e., SFLLRN (SEQ ID NO:23)) or thrombin. Addition of lipid-tethered peptides that mimic the receptor ligand binding site(s) might be expected to interfere with thrombin-activated receptor (intramolecular ligand) or exogenously added intermolecular ligand (FIG. 8). Other extracellular loops of the receptor also likely make contact with the ligand and contribute regions termed ligand binding site-2 (LBS-2), LBS-3, etc.

Figure 9C:
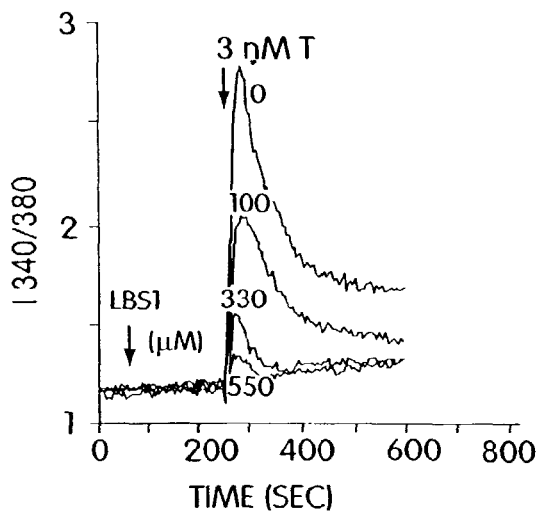
FIGS. 9A and B are schematic representation of LBS-1 pepducins.
FIG. 9 C is a line graph indicating the fluorescence excitation intensity at 340/380 nm showing that the non-lipidated LBS-1 peptide is a poor antagonist against thrombin and SFLLRN (SEQ ID NO:23) activation of PAR-1-dependent platelet $Ca^{2+}$ fluxes (FIGS. 9C, and 9D, respectively).
FIG. 9E is a line graph showing LBS-1 inhibition of thrombin aggregation of platelets.
Figure 9D:
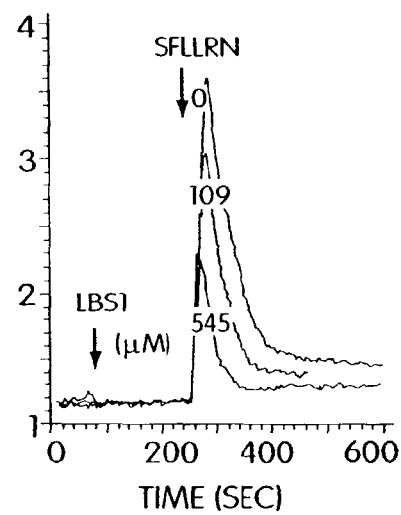
Figure 9E:
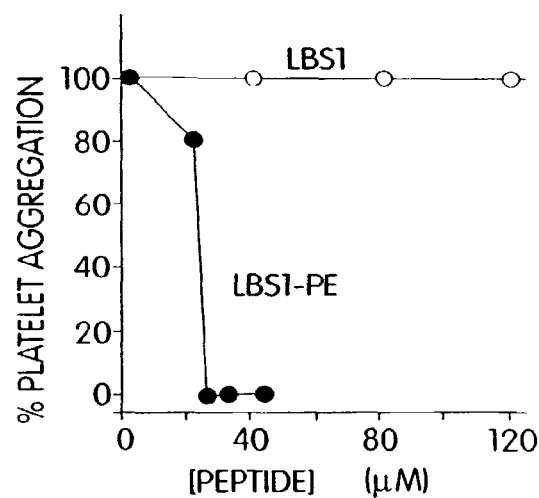

A peptide based on the extracellular loop of the PAR1 receptor (LBS1: PAFISEDASGYL-C) (SEQ ID NO:27) was synthesized. This peptide contains the $P_{85}AFIS_{89}$ (SEQ ID NO:31) sequence of PAR1 and adjacent C-terminal residues $E_{90}DASGYL_{96}$-C (SEQ ID NO:32) that are expected to come into close proximity with the lipid bilayer in the intact receptor (FIG. 9B). The non-lipidated LBS1 peptide was a relatively poor antagonist against thrombin and SFLLRN (SEQ ID NO:23) activation of PAR1-dependent platelet Ca$^{2+}$ fluxes (FIGS. 9C, and 9D, respectively). Likewise, the non-lipidated LBS1 peptide did not inhibit 3 nM thrombin aggregation of the platelets (FIG. 9E). In marked contrast, the C-terminally lipidated peptide, LBS1-PE (FIG. 9A) was an effective inhibitor of platelet aggregation. As shown in FIG. 9E, 25 micromolar LBS1-PE completely inhibited 3 nM thrombin-induced platelet aggregation.

The LBS1 peptide included a C-terminal cysteine residue and was synthesized by solid-phase fmoc chemistry. The wild-type peptide $E_{90}DASGYLT_{97}$ (SEQ ID NO:37) was modified so that amino acid 97 (T) was removed and replaced with a lipidated cysteine. Lipidation of the C-terminal cysteine thiol of LBS1 was done with N-MPB-PE (1,2-dipalmitoyl-sn-glycero-3-phosphoethanolamine-N-[4-(p-maleimidophenyl)-butyramide]) by mixing 2.5 mM peptide and 5 mM N-MPB-PE (Avanti Polar Lipids) in 6% triethylamine/94% dimethylformamide and incubating at ambient temperature (23 C) for 2 h. The LBS1 peptide-Cys-PE conjugate was purified by Sep-Pak (Waters) C18 reverse-phase chromatography, and identity confirmed by mass spectrometry.

Example 8

Pepducin Activation of the $G_S$-Coupled MC4 Obesity Receptor

Figure 7:
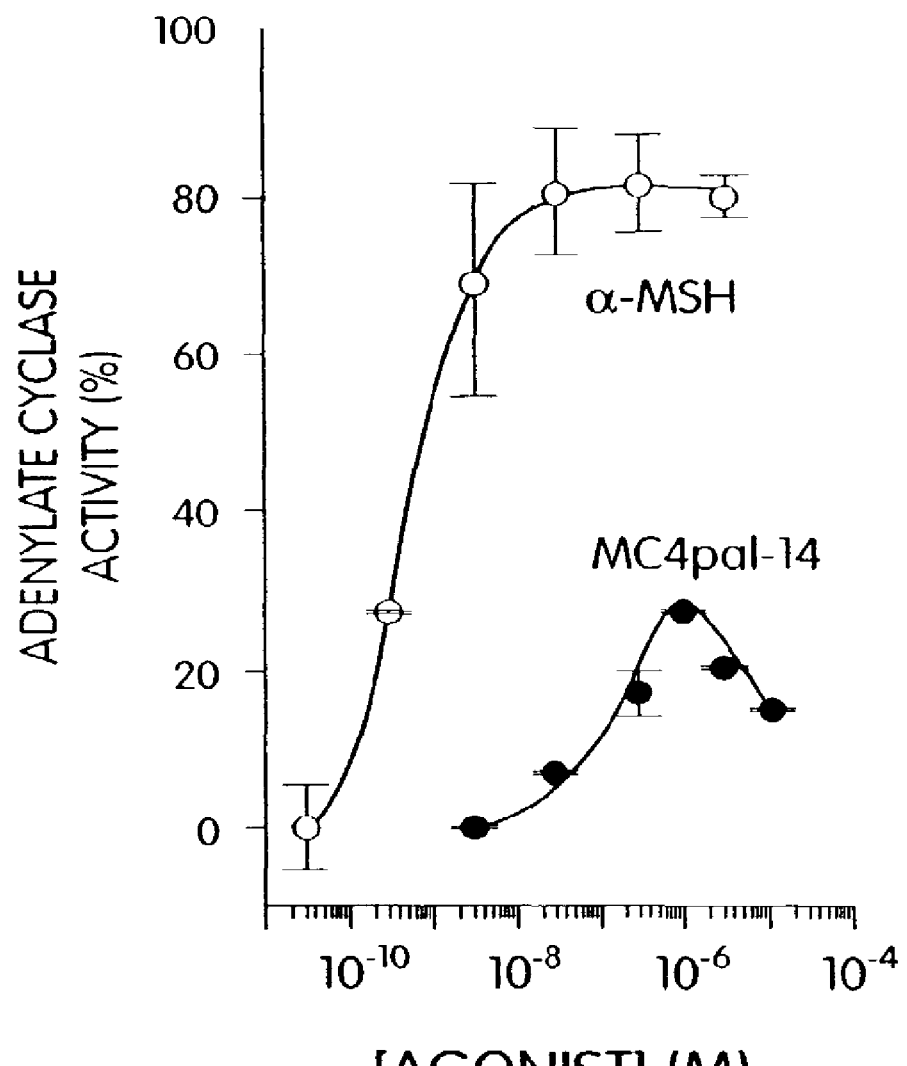
FIG. 7 is a line graph depicting pepducin activation of the $G_S$-coupled MC4 obesity receptor.

Activation of the MC4 receptor (MC4R) by melanocortin agonists, such as melanocyte stimulating hormone (alpha-MSH) causes anorexia (loss of appetite) and weight loss in mice. Mutations of the MC4R have been found in extremely obese humans. A pepducin, MC4pal-14 (Pal-TGAIRQGAN-MKGAI) (SEQ ID NO:28) that corresponds to the third intracellular loop of the human MC4R was synthesized and tested the pepducin for agonist activity with its cognate receptor. Addition of MC4pal-14 to COST fibroblasts transiently transfected with MC4R stimulated adenylate cyclase activity by 40% relative to authentic agonist, alpha-MSH. The activity profile of MC4pal-14 is biphasic with an activating phase (EC$_{50}$~150 nM) and inhibitory phase (IC$_{50}$~10 micromolar). These data demonstrate that the pepducins can activate $G_S$-coupled receptor pathways and that MC4pal-14 and its derivatives may have utility as anti-obesity agents in humans. Further, it is noteworthy that unlike systemically injected peptide agonists like alpha-MSH, these cell penetrating pepducins would be expected to cross the blood-brain barrier to activate receptors such as MC4R located in the central nervous system. (FIG. 7)

Example 9

Selectivity of P1pal-12 Pepducin

Figure 10A:
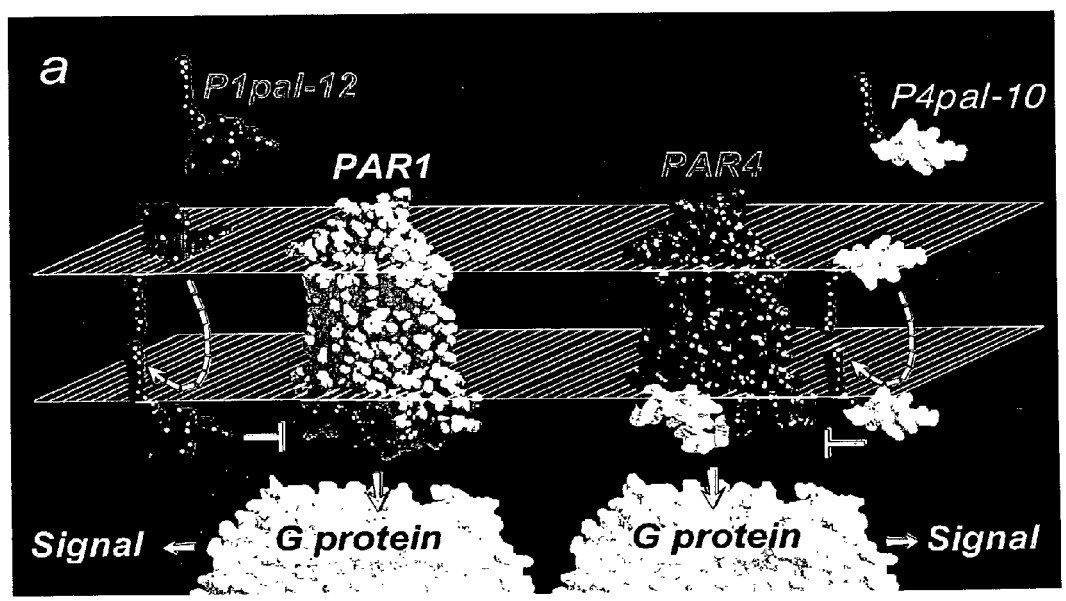
FIGS. 10A through 10E depict a schematic of the PAR1 and PAR4 receptors, pepducins of the present invention and their effect on the activation and/or regulation of $Ca^{2+}$ signaling and aggregation in platelets.

P1pal-pepducin (SEQ ID NO:4) (FIG. 10A, FIG. 11F) lacked agonist activity yet was a full antagonist of PAR1-dependent inositol phosphate (InsP) production and Ca$^{2+}$ signaling in platelets and recombinant systems. Covic et al., PNAS 99, 643 (2002). Preincubation of human platelets with 3 μM P1pal-12 for 1 min blocked 75-95% of aggregation in response to the PAR1 extracellular ligand SFLLRN (SEQ ID NO:23) (FIG. 11b).

The selectivity of the P1pal-12 pepducin for PAR1 versus other human GPCRs was examined, including PAR4, thromboxane A2 (TXA$_2$) (Murray and FitzGerald, Proc. Natl. Acad. Sci. (USA) 86, 124 (1989)), P2Y$_1$ and P2Y$_{12}$ ADP receptors (Woulfe et al., J. Clin. Invest. 107, 1503 (2001)) and non-G-protein coupled receptors for collagen ($a_2\beta_1$, GPVI/ FcγII) Moroi et al., J. Clin. Invest. 84, 1440 (1989)) and von Willebrand factor (GPIb/IX/V) (Savage et al., Cell 94, 657 (1998)) using platelets as the biologically-relevant system. P1pal-12 was selective for PAR1 and did not block aggregation induced by the extracellular ligands of the other platelet receptors. The anti-PAR1 pepducin, P1pal-12, does not inhibit PAR4-dependent platelet aggregation.

Example 10

Selectivity of P4pal-10 Pepducin

In addition to PAR1, the PAR4 receptor plays a major role in thrombin signaling in human platelets and is responsible for formation of stable platelet-platelet aggregates during the propagation phase of haemostasis. Covic et al., Biochemistry 39, 5458 (2000); and Covic et al., Thromb. Haemost. 87, 722 (2002). The palmitoylated peptide based on the human PAR4 i3 loop, P4pal-10, Pal-SGRRYGHALR (SEQ ID NO:29) (FIG. 10a, FIG. 11f), was synthesized. P4pal-10 had no agonist activity as measured by platelet aggregation, intracellular $Ca^{2+}$ release in human platelets, or InsP production in COS7 cells transfected with hPAR4.

Figure 10:
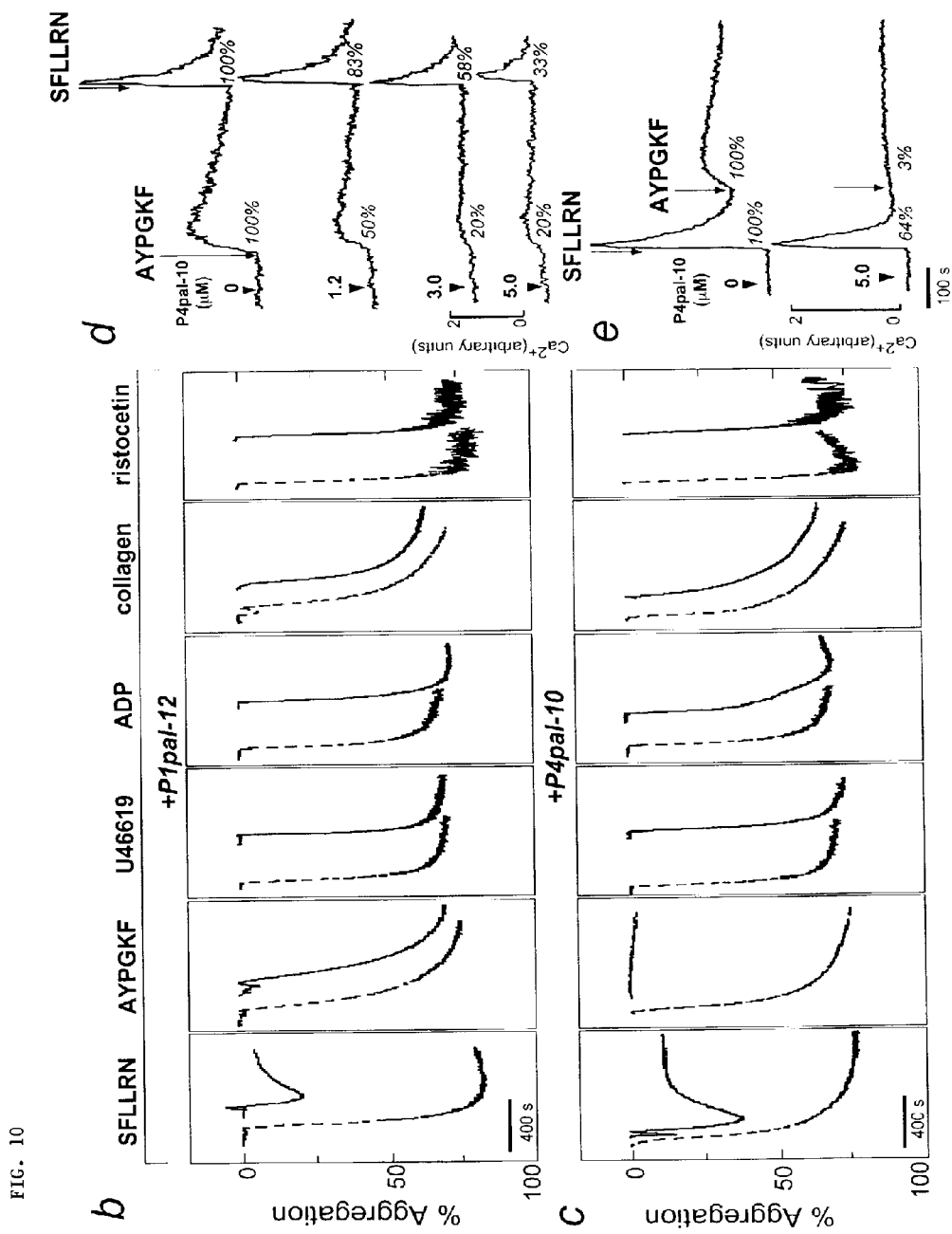

As shown in FIGS. 10 b-c, P1pal-12 and P4pal-10 selectively inhibit thrombin receptors on human platelets. Platelets were preincubated with either 5 µM P1pal-12 or 5 µM P4pal-10 for 1 min and then challenged with 3 µM SFLLRN (SEQ ID NO:23), 200 µM AYPGKF (SEQ ID NO:26), 20 µM U46619, 5 µM ADP, 20 mg/mL collagen or 1 mg/mL ristocetin, and platelet aggregation monitored. Full platelet aggregation traces (dashed lines) are also shown for each agonist in the absence of inhibitors.

As shown in FIGS. 10D-E, human platelets were pretreated for 1 min with the indicated concentrations of P4pal-10 and challenged with 200 µM AYPGKF (SEQ ID NO:26) and 30 µM SFLLRN (SEQ ID NO:23) as indicated. Intracellular $Ca^{2+}$ concentration was monitored as the ratio of fluorescence excitation intensity at 340/380 nm of platelets labeled with fura-2AM. The integrated $Ca^{2+}$ response for the individual treatments are relative to the full $Ca^{2+}$ responses for each agonist (100%) recorded in the absence of P4pal-10 (top trace).

P4pal-10 was tested extensively for the ability to act as an antagonist of platelet PAR4. Preincubation of human platelets with P4pal-10 completely blocked aggregation ($IC_{50}$=0.5-1 µM) in response to the PAR4 peptide ligand, AYPGKF (SEQ ID NO:26) (FIG. 10c). The P4pal-10 PAR4 antagonist could also partially inhibit activation of PAR1 by SFLLRN (SEQ ID NO:23), but did not appreciably block aggregation in response to agonists for the $TXA_2$, ADP, collagen, or GPIb/ IX/V receptors (FIG. 10c).

Figure 5:
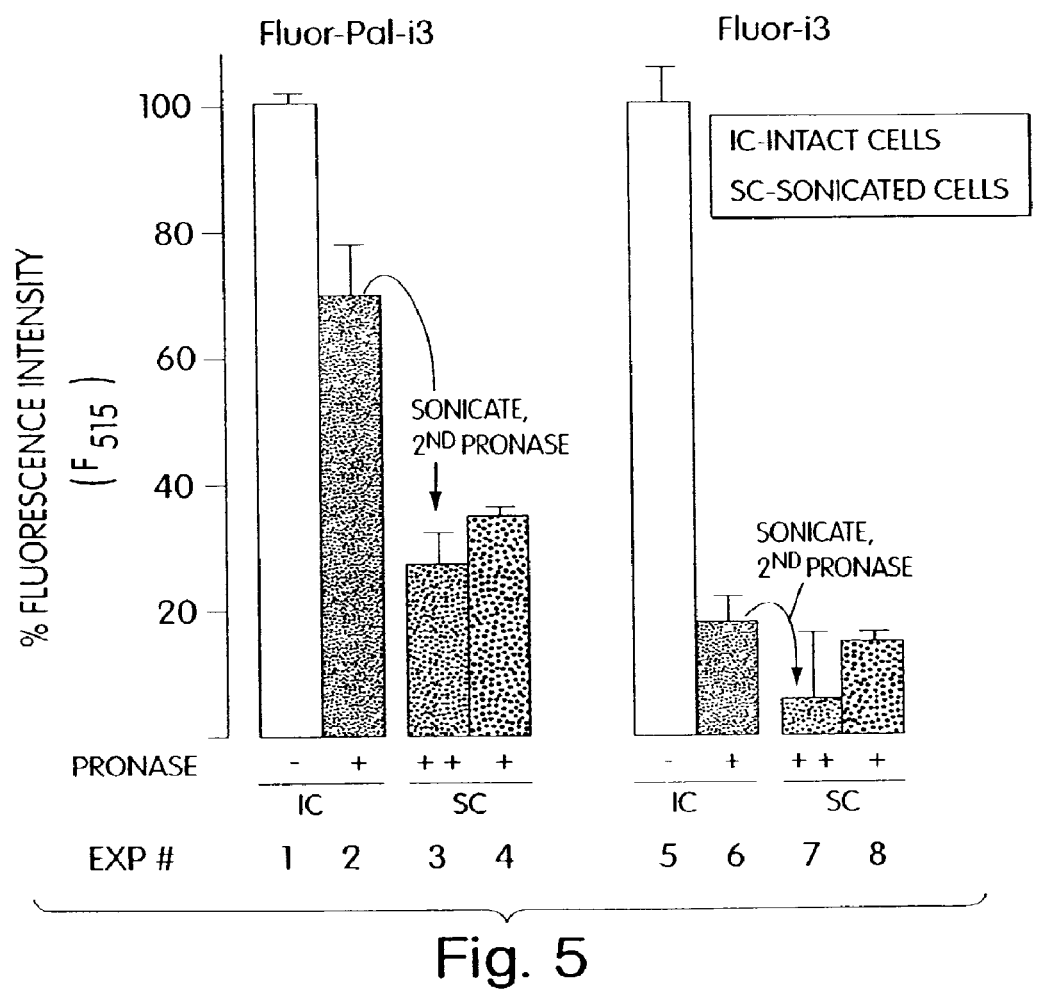
FIG. 5 is a bar graph of showing that the peptides of the present invention penetrate intact cells.
Figure 6B:
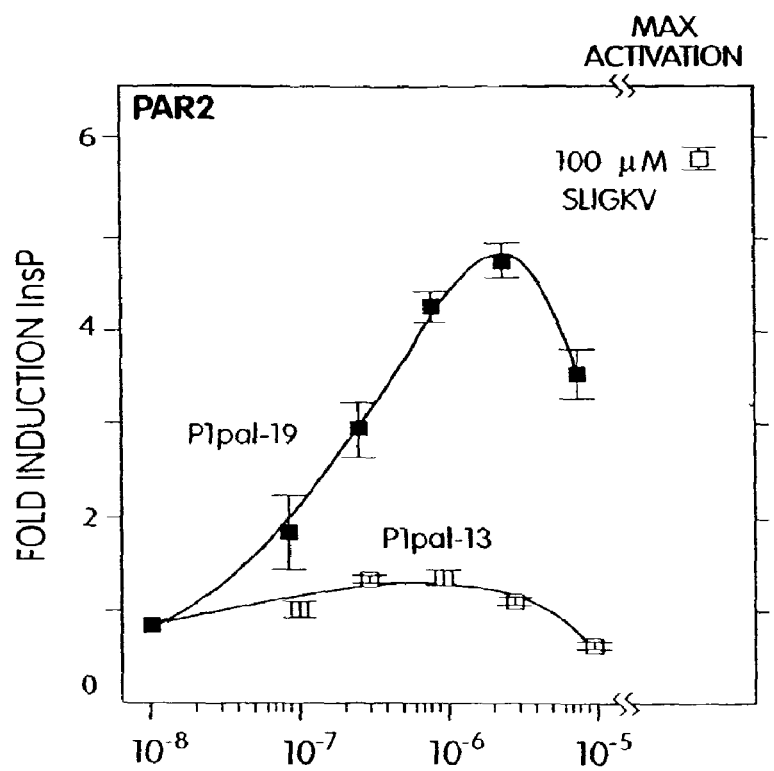
FIGS. 6B-D are line graphs of the activation various receptors by pepducins, as measured by PLC-β activity (measured by inositol phosphate formation).
Figure 6C:
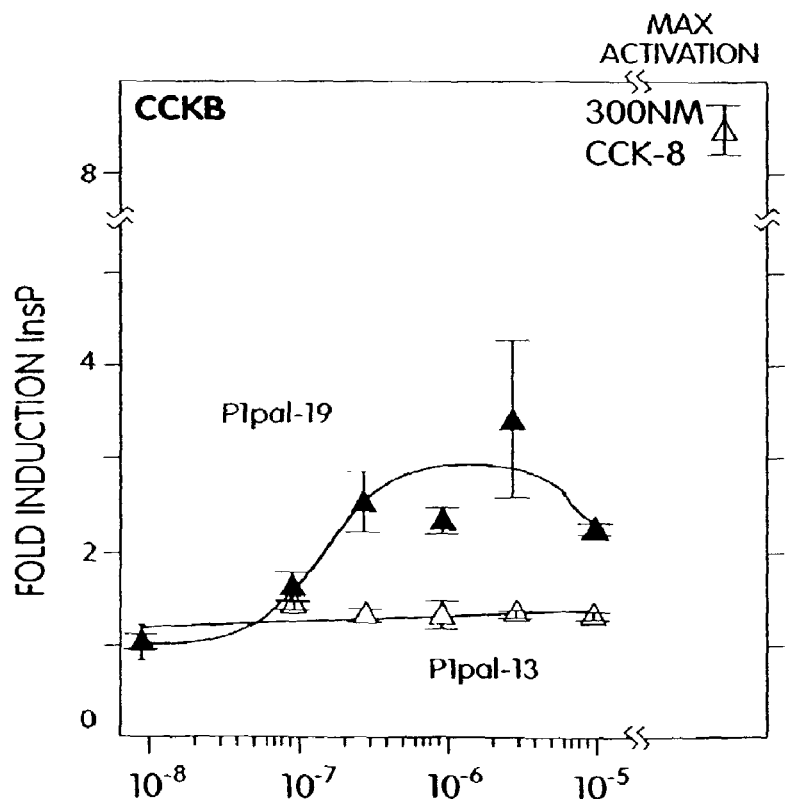
Figure 6D:
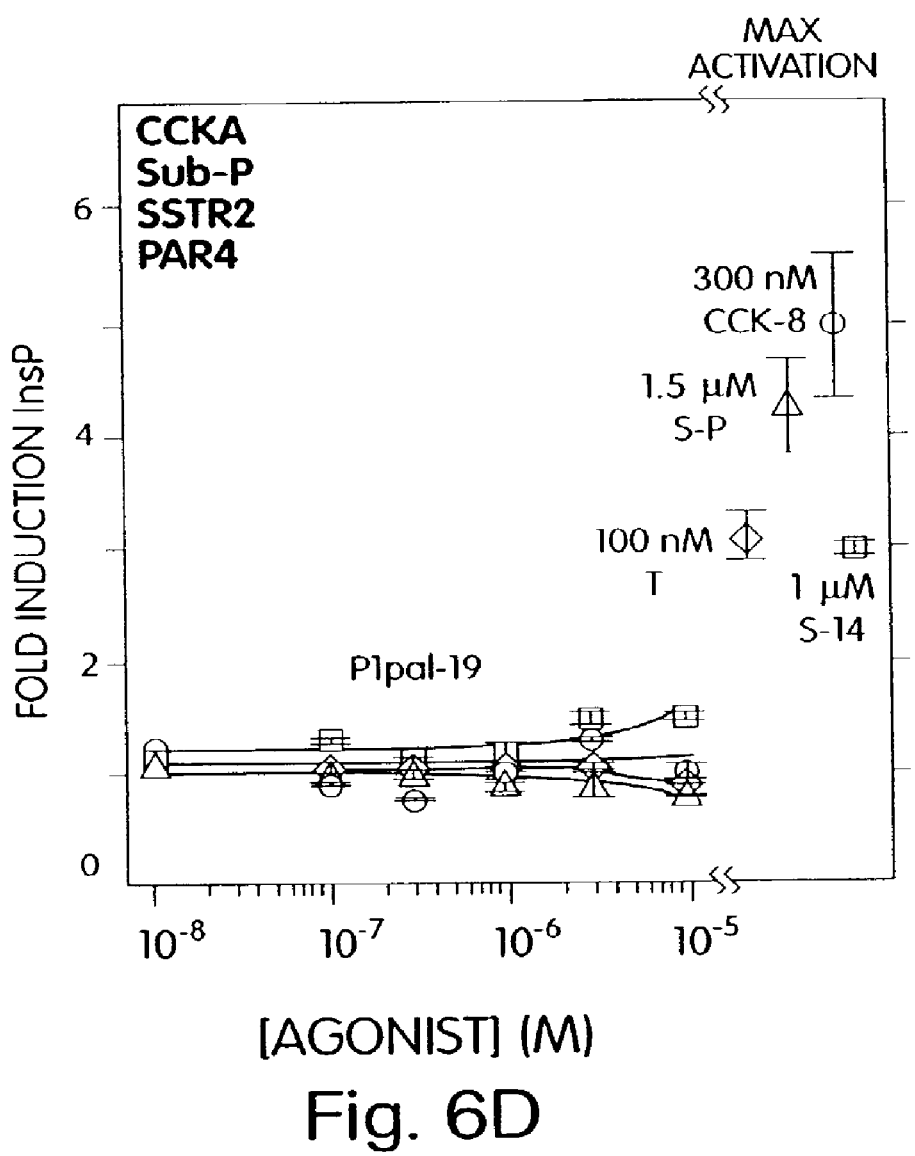

To further define the selectivity of inhibition of the P4pal-10 pepducin, its ability to block PAR1 and PAR4-dependent $Ca^{2+}$ transients generated through the $G_q$/PLC-β signaling pathway (Offermanns et al., Nature 389, 183 (1997)) in platelets was examined. Stimulation of PAR4 with the AYPGKF (SEQ ID NO:26) agonist gives rise to a prolonged $Ca^{2+}$ signal whereas stimulation of PAR1 with SFLLRN (SEQ ID NO:23) gives a distinct spike response. Covic et al., Biochemistry 39, 5458 (2000). Preincubation of human platelets with 1.2-5 µM P4pal-10 attenuated 50-80% of the PAR4 response, and 17-67% of the PAR1 $Ca^{2+}$ signal subsequently induced by SFLLRN (SEQ ID NO:23) (FIG. 10d). When the order of peptide agonists is reversed (SFLLRN (SEQ ID NO:23) followed by AYPGKF SEQ ID NO:26)) the specificity of P4pal-10 is higher in favor of PAR4 over PAR1. As shown in FIG. 10E, 5 µM P4pal-10 inhibits only 36% of the PAR1 $Ca^{2+}$ response while inhibiting 97% of the PAR4 response. The PAR4 $Ca^{2+}$ response to peptide agonists (FIG. 10E) is typically desensitized by ~2-fold when it follows SFLLRN (SEQ ID NO:23) stimulation of PAR1. Covic et al., Biochemistry 39, 5458 (2000). This may explain the relative differences in magnitude of the inhibitory effects of P4pal-10 on the $Ca^{2+}$ response for the two receptors depending on the order of addition of agonists. Unlike P1pal-12, P4pal-10 can inhibit signaling from both PAR4 and PAR1 thrombin receptors with higher selectivity for PAR4 over PAR1.

Example 11

Pepducin Modulation of Platelet Aggregation

It is shown herein that P1pal-12 and P4pal-10 pepducins are effective inhibitors of the soluble peptide ligands of PAR1 and PAR4. Previous studies have shown that it is considerably more difficult to generate effective antagonists of the tethered ligands of PARs produced by proteolytic cleavage of the extracellular domains (Seiler et al., Mol. Pharm. 49, 190 (1996); and Bematowicz et al., J. Med. Chem. 39, 4879 (1996)). More recently, small molecule antagonists have been described that do block thrombin activation of PAR1 (Andrade-Gordon et al., J. Pharm. Exp. Therap. 298, 34 (2001); and Proc. Natl. Acad. Sci. (USA) 96, 12257 (1999)) in human platelets and rodent model systems, and peptide-ligand antagonists of PAR4 (Ma, et al., Br. J. Pharm. 134, 701 (2001)) have been shown to block thrombin-induced endostatin release from human platelets. Concentrations of thrombin as low as 3 nM cleave sufficient PAR1 to fully activate human platelets (Covic et al., Biochemistry 39, 5458 (2000); and Covic et al., Thromb. Haemost. 87, 722 (2002)). PAR4 is also activated by 3 nM thrombin but does not generate a sufficiently strong signal to fully aggregate human platelets until the thrombin concentration exceeds ~5 nM (Covic et al., Thromb. Haemost. 87, 722 (2002)).

Figure 11:
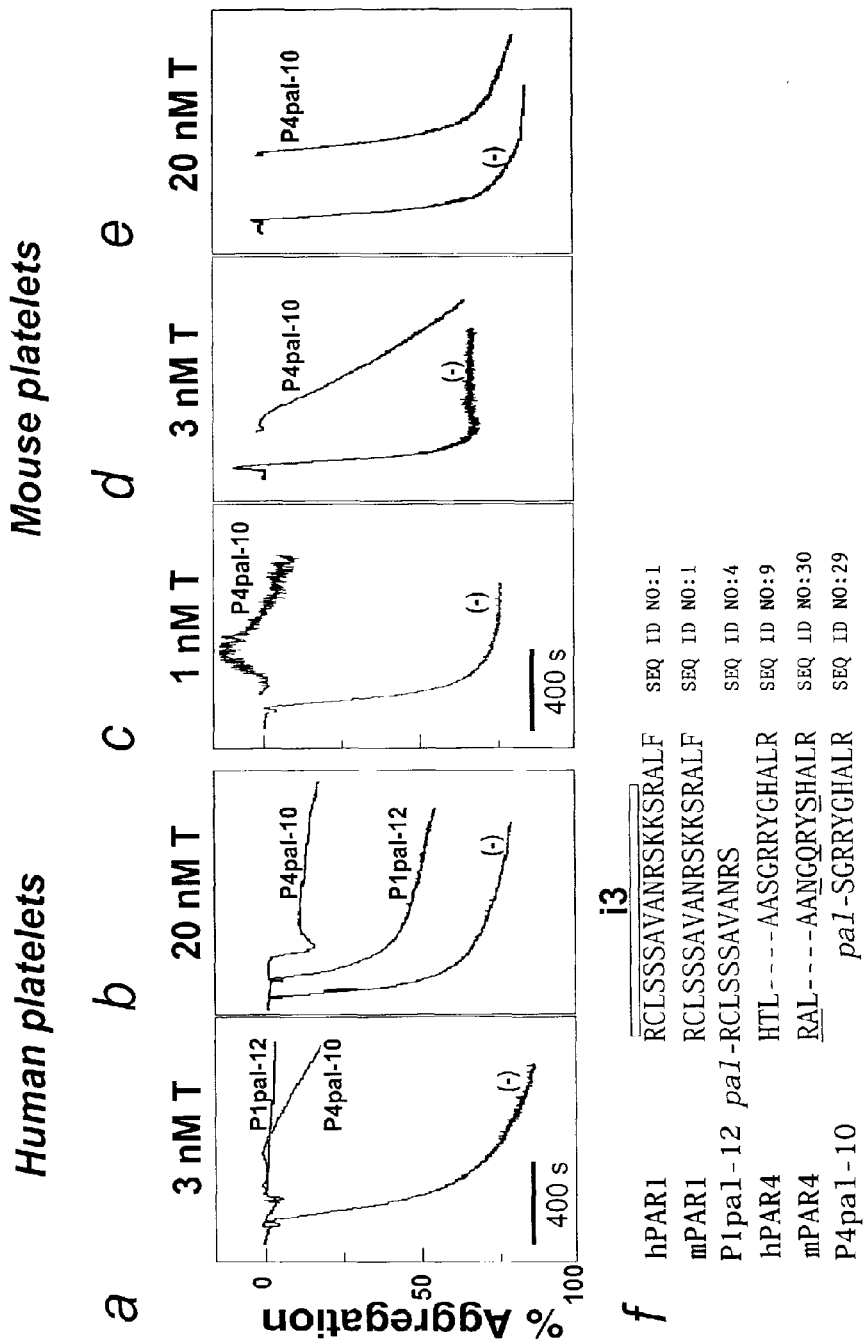
FIGS. 11A through 11F show the effect of p4pal-10 on human and mouse platelets, and an alignment of the third intracellular loops of human and murine PAR4.

In FIGS. 11 a-b, aggregation was performed with human platelets pretreated for 1 min with 3 µM P1pal-12 or 3 µM P4pal-10 as indicated and stimulated with 3 nM thrombin (T) or 20 nM thrombin. Aggregation was monitored as % light transmittance of stirred platelets at 37° C. Full platelet aggregation traces (–) are also shown for each agonist in the absence of inhibitors. Pretreatment of human platelets with the anti-PAR1 pepducin, P1pal-12, completely blocked aggregation in response to 3 nM thrombin (FIG. 11a). Challenge of platelets with 20 nM thrombin was not appreciably blocked by P1pal-12, presumably due to the additional signal from the cleaved PAR4 receptor (FIG. 11b).

The PAR4 pepducin, P4pal-10, also inhibited human platelet aggregation to 3 nM thrombin though not as efficiently as P1pal-12 (FIG. 11a). Strikingly, P4pal-10 inhibited 85% of human platelet aggregation in response to 20 nM thrombin-conditions where normally both PAR1 and PAR4 would be fully activated (Covic et al., Thromb. Haemost. 87, 722 (2002)) (FIG. 11b). The efficient blockade of thrombin-induced platelet aggregation by P4pal-10 is consistent with the inhibition data (FIG. 10c) which show that the anti-PAR4 pepducin completely blocks PAR4 and cross-inhibits PAR1. The cross-inhibition of PAR1 by the anti-PAR4 pepducin may have important ramifications for the therapeutic utility of anti-PAR pepducins by blocking a higher range of thrombin concentrations. One possible explanation for the cross-specificity of P4pal-10 is the sequence similarity of the C-terminal region of the i3 loops in human PAR1 and PAR4, both of which include a stretch of basic residues (FIG. 11f). Thus, the P1pal-12 pepducin based on the N-terminal region of the PAR1 i3 loop does not appreciably cross-inhibit PAR4 which has poor homology to PAR1 in this region. Conversely, the P4pal-10 pepducin based on the more highly conserved C-terminal region of the i3 loop has markedly higher cross-reactivity between PAR1 and PAR4.

Example 12

Pepducin Modulation of Thrombosis In Vivo

The anti-PAR4 pepducin was tested as an anti-thrombotic agent under in vivo conditions using a mouse model system. The anti-PAR4 pepducin was investigated rather than the anti-PAR1 pepducin because mouse platelets lack PAR1 and generate thrombin signals solely through PAR4 (Sambrano et al., Nature 413, 74 (2001)). In FIGS. 11 c-e, aggregation was performed on washed murine platelets pretreated with 3 µM P4pal-10 for 1 min and challenged with 1-20 nM thrombin. In FIG. 11f, alignment of the third intracellular loops (i3) from human and murine PAR1 and PAR4 is shown.

It was determined that the P4pal-10 pepducin based on the human PAR4 i3 loop, inhibits activation of mouse platelets by thrombin. As shown in FIGS. 11C-D, 3 µM P4pal-10 completely blocks aggregation of murine platelets by 1 nM thrombin ($EC_{50}$=0.6 nM) and causes a 7-fold inhibition of the rate of aggregation to 3 nM thrombin. In addition, 3 µM P4pal-10 blocked 75% of aggregation of murine platelets in response to 100 µM AYPGKF (SEQ ID NO:26), the soluble PAR4 peptide ligand. Together, these data suggest that the 70% identity between human and murine PAR4 in the region of P4pal-10 (FIG. 11F) provides enough homology for the human anti-PAR4 pepducin to be effective in both species. Unlike the case in human platelets, however, the inhibition of murine platelets by P4pal-10 is overcome at 20 nM thrombin (FIG. 11E). This may be due in part to sequence differences between human and murine PAR4 (77% overall identity).

It was then determined that fluorescently-labeled palmitoylated i3 loop peptides based on PAR1 (fluorescently-labeled PAR4 i3 loop pepducins were insoluble) could be delivered to circulating mouse platelets.

Figure 12:
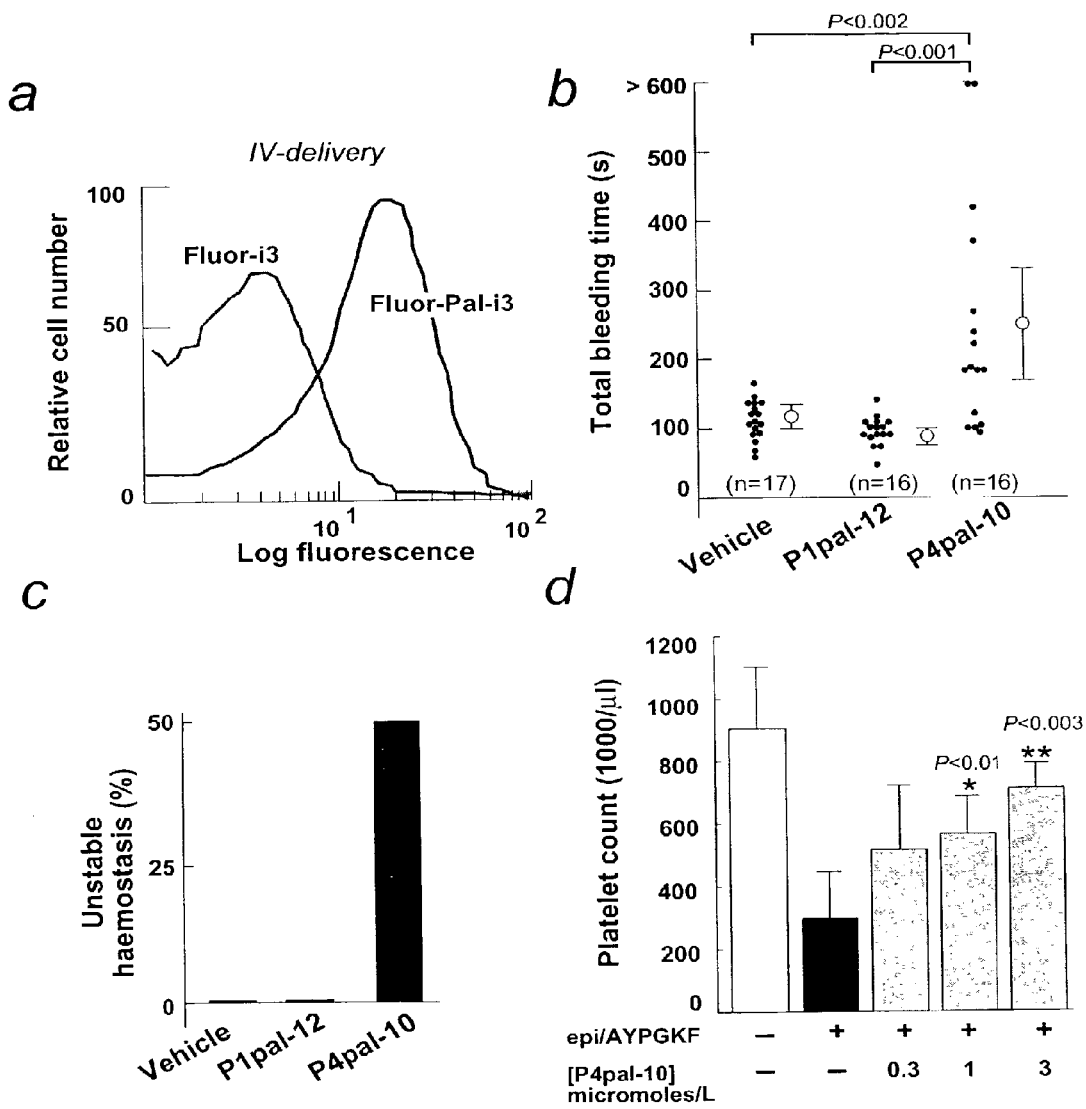
FIGS. 12A through 12D indicate that P4pal-10 prolongs bleeding time and protects against systemic platelet activation.

FIG. 12 indicates that the human P4pal-10 pepducin prolongs bleeding time and protects against systemic platelet activation in mice. FIG. 12A shows that the palmitoylated i3-loop peptide accumulates in circulating mouse platelets. Palmitoylated and non-palmitoylated PAR1-i3 loop peptides were tagged with fluorescein (Covic et al., PNAS 99, 643 (2002)) and injected into the mouse via a catheter in the internal jugular vein. Mice were injected with 1 µmoles/L of palmitoylated (Fluor-Pal-i3: Pal-RC(Fluor-5EX)LSSSA-VANRSK(Fluor-5EX)K(Fluor-5EX)SRALF) (SEQ ID NO: 1) or nonpalmitoylated (Fluor-i3: (Fluor-5EX)-NH RSLSS-SAVANRSK(Fluor-5EX)K(Fluor-5EX)SRALF) (SEQ ID NO: 45) fluorescein-labeled PAR1 i3-loop peptides. The fluorescently-labeled peptides were allowed to circulate for 15 min, then whole blood was collected and the platelets purified by centrifugation and treated with 2 U of pronase (to remove peripherally-bound peptides) for 15 min prior to flow cytometry (Azam et al., Mol. Cell. Biol. 21, 2213 (2001), Covic et al., PNAS, 99:643-648 (2002)). 10,000 platelets were analyzed for fluorescence using a FACS Scan flow cytometer and the data plotted as a histogram of relative cell number versus fluorescence (FIG. 12A). Flow cytometry revealed that circulating mouse platelets exposed to the palmitoylated Fluor-Pal-i3 acquired 5-fold higher fluorescence relative to platelets exposed to the non-palmitoylated Fluor-i3 (FIG. 12A). This demonstrates that the intravenously-injected Pal-i3 loop peptides are delivered to circulating platelets and are supportive of the proposed mechanism of FIG. 10A that palmitoylation is sufficient for delivery of the i3 peptide through the plasma-cell membrane. Because murine platelets lack PAR1, yet accumulated the fluorescently-labeled PAR1 i3 loop pepducin, it is unlikely that pepducins distribute to cells according to the tissue-expression of their cognate receptor.

The effect of blockade of PAR4 with parenterally-administered P4pal-10 on primary haemostasis was examined. It is known that knockout of the PAR4 gene results in uncontrolled tail-bleeding (Sambrano et al., Nature 413: 74 (2001)). P4pal-10 (3 µmoles/L) was infused into the mouse jugular vein and allowed to circulate for 5 min prior to tail-bleed measurements. FIG. 12B demonstrates that intravenous administration of P4pal-10 results in rebleeding from amputated tail tips in mice. 50% of the mice (8/16) that were injected with P4pal-10 formed unstable thrombi at the amputated tail tips. Thus, in several cases after initial cessation of bleeding, the stream of blood reappeared after 54-280 s, and the tail re-bled for an additional 1-10 min (mean=3.2 min). The re-bleeding phenomena was not observed in any of the negative control experiments. In these experiments, mice were infused with the anti-PAR1 pepducin, P1pal-12 or injected with vehicle (0/17) alone. P1pal-12 (3 µmoles/L, n=16), P4pal-10 (3 µmoles/L, n=16), or vehicle (DMSO, n=17) alone were allowed to circulate for 5 min prior to tail-bleed measurements. The re-bleeding observed in the mice treated with the anti-PAR4 pepducin is consistent with the predicted physiological role of PAR4 in humans where PAR4 has been shown to control the stability of platelet-platelet aggregates (Covic et al., Biochemistry 39, 5458 (2000); and Covic et al., Thromb. Haemost. 87, 722 (2002)).

The total mean bleeding time was markedly prolonged in the mice treated with P4pal-10 as compared to mice injected with vehicle alone (FIG. 12C). FIG. 12C shows that blocking PAR4 with P4pal-10 extends tail-bleeding time in mice, the mean total bleeding times ±2 S.E. are shown as open circles (P<0.002). The mean total bleeding time of the P4pal-10-treated mice was 249 s, compared to 119 s for the vehicle-treated mice or 95 s for the P1pal-12-treated mice.

Thus, treatment of mice with P1pal-12 (3 mmoles/L) did not prolong tail-bleeding time or result in unstable haemostasis (FIGS. 12B-C) as was observed with P4pal-10. The PAR1 pepducin antagonist was predicted to have no effect on haemostasis since platelets that are derived from mice genetically deficient in PAR1 have no defects in thrombin signaling and aggregation and have normal bleeding times (Connolly et al., Nature 381: 516 (1996)).

In FIG. 12 D, platelets were systemically activated by intravenous infusion of an AYPGKF (SEQ ID NO:26)/epinephrine cocktail without or with varying amounts of P4pal-10, and platelet count was measured. As shown in the figure, the PAR4 pepducin P4pal-10 protects against systemic platelet activation in mice. P4pal-10 (0.3-3 µmoles/L) or vehicle alone (DMSO) were delivered intravenously and allowed to circulate for 5 min.

Example 13

Pepducins as Protective Agents In Vivo

The efficacy of the anti-PAR4 pepducin as a protective agent against systemic platelet activation in vivo was assessed. Intravascular platelet activation was induced with a cocktail containing the PAR4 agonist AYPGKF (SEQ ID NO:26) plus epinephrine. Epinephrine activates the $G_{i(z)}$- coupled α₂-adrenergic receptor (Woulfe et al., J. Clin. Invest. 107, 1503 (2001)) which serves to potentiate the response of G$_q$-coupled receptors like PAR4. Infusion of the platelet agonist cocktail caused a precipitous drop in mean platelet count from 900×10³ to 300×10³/μL (FIG. 12d) which is due to incorporation of platelets into systemic thrombi (Fabre et al., Nat. Med. 5:1199 (1999); and Smyth et al., Blood 15:1055 (2001)). In contrast, pre-infusion with 0.3 μmoles/L of P4pal-10 provided 36% protection against systemic thrombus formation (P<0.08). Higher concentrations of P4pal-10 (1 and 3 mmoles/L) resulted in 45-70% protection against systemic platelet activation (P<0.01-0.003). The protective effect of blockade of PAR4 with the P4pal-10 pepducin strongly correlates with the results obtained with mice genetically-deficient in PAR4 which were shown to be resistant to arteriolar thrombosis (Sambrano et al., Nature 413:74 (2001)). Together, these data demonstrate that pharmacologic blockade of PAR4 with the P4pal-10 pepducin protects against systemic platelet activation and suggest that PAR4 may be an important target in the prevention of thrombosis in humans.

The deployment of i3-loop pepducins provides a simple and powerful approach to determine the effect of pharmacologic disruption of GPCRs which lack a known extracellular antagonist. The application of pepducins in in vivo model systems, such as mice, is useful to validate and extend the information generated from genetic knockout of a GPCR, particularly in cases where embryonic lethality resulting from genetic disruption of the GPCR precludes analysis in the mature animal.

Example 14

Inhibition of the P2Y$_{12}$ ADP Nucleotide Receptor with Pepducins

Figure 13:
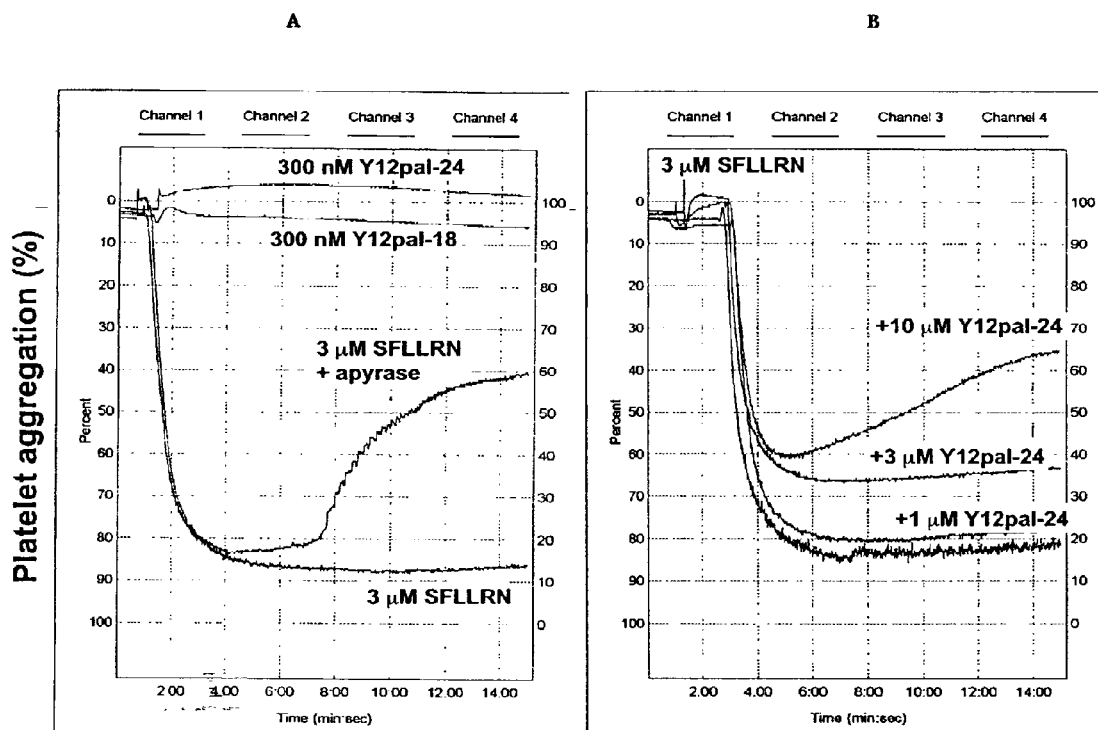
FIGS. 13A and B are graphs showing inhibition of platelet aggregation by $P2Y_{12}$-based i3 loop pepducins. Figures disclose "SFLLRN" as SEQ ID NO: 23.

Recently, the P2Y$_{12}$ adenosine diphosphate (ADP) receptor was cloned by three independent groups (Hollopeter et al., Nature 409:202 (2001); Zhang et al., J. Biol. Chem. 276:8605 (2001); and Takasaki et al., Mol. Pharmacol. 60:432 (2001)) and shown to be the long-sought after target of the thienopyridine drugs clopidogrel and ticlopidine (Gachet et al., Biochem Pharmacol 40:2683 (1990); Mills et al., Arterioscler Thromb 12:430 (1992)). These anti-P2Y$_{12}$ drugs are highly effective antithrombotic agents for the treatment of patients with acute coronary syndromes. P2Y$_{12}$ plays such a critical role in thrombus formation because it can modulate the strength of platelet-platelet adhesive interactions via multiple receptors such as PAR1. Inputs from P2Y$_{12}$ stabilize the critical transition point of platelet-platelet aggregates during the progression from early reversible GPIIb-IIIa-fibrinogen binding to the late phase of irreversible binding to fibrinogen. For example, the PAR1 agonist, SFLLRN (SEQ ID NO: 23), causes full and irreversible platelet aggregation (FIG. 13A). If the ADP nucleosidase apyrase is added, aggregation becomes reversible to SFLLRN (SEQ ID NO: 23). This is because apyrase destroys the ADP that is released from the platelet dense granules and the P2Y$_{12}$ ADP receptor can no longer stabilize the platelet-platelet aggregates initiated by addition of the PAR1 agonist, SFLLRN (SEQ ID NO: 23). Pepducins based on the i3-loop of P2Y$_{12}$ (Y12pal-18 and Y12pal-24) were made, and were determined to have no agonist activity in platelet aggregation assays (FIG. 13A).

Y12pal-24 was an effective inhibitor of irreversible platelet aggregation (FIG. 13B) and at 10 μM was equivalent in efficacy as addition of saturating amounts of apyrase which completely ablates the ADP autocrine response (FIG. 13A). Human platelets (gel-purified) were activated with 3 μM SFLLRN (SEQ ID NO: 23) in the presence of 0, 1, 3, or 10 μM pepducin. Aggregometry was performed by light scattering.

These data demonstrate that pepducins can be made to inhibit nucleotide-liganded GPCRs which further underscores their general applicability across the various classes of GPCRs.

Example 15

Activation and Inhibition of a Class B GPCR (Glucagon-Like Peptide Receptor-1) with Pepducins Glucose-induced insulin secretion is modulated by a number of hormones and neurotransmitters. In particular, two gut hormones, glucagon-like peptide-1 (GLP-1) and gastric inhibitory peptide (GIP) potentiate the effect of glucose on insulin secretion and are thus called gluco-incretins (Dupre, The Endocrine Pancreas, E. Samois Ed. (Raven Press, New York, 253-281 (1991)) and Ebert and Creutzfeld, Diabetes Metab. Rev. 3, (1987)). Glucagon-like peptide-1 is a gluco-incretin both in rat and in man (Kreymann et al., Lancet 2:1300 (1987)). It is part of the preproglucagon molecule (Bell et al., Nature 304:368 (1983)) which is proteolytically processed in intestinal L cells to GLP-1 (1-37) and GLP-1 (7-36)amide or GLP-1 (7-37) (Mojsov et al., J. Biol. Chem. 261:11880 (1986) and Habener et al., The Endocrine Pancreas E. Samois Ed. Raven Press, New York 53-71 (1991)). The stimulatory effect of these gluco-incretin hormones is mediated by activation of adenylate cyclase and a rise in the intracellular concentration of cyclic AMP (Drucker et al., Proc. Natl. Acad. Sci. USA 84:3434 (1987) and G'ke et al., Am. J. Physiol. 257:G397 (1989)). GLP-1 has also a stimulatory effect on insulin gene transcription (Drucker et al., Proc. Natl. Acad. Sci. USA 84: 3434 (1987)). In a rat model, non-insulin-dependent diabetes mellitus (NIDDM) is associated with a reduced stimulatory effect of GLP-1 on glucose-induced insulin secretion (Suzuki et al., Diabetes 39:1320 (1990)). In humans, in one study, GLP-1 levels were elevated in NIDDM patients both in the basal state and after glucose ingestion; however, following a glucose load there was only a very small rise in plasma insulin concentration (Qrskov et al., J. Clin. Invest. 87:415 (1991)). Another recent study (Nathan et al., Diabetes Care 15: 270 (1992)) showed that GLP-1 infusion could ameliorate postprandial insulin secretion and glucose disposal in NIDDM patients.

Figure 14:
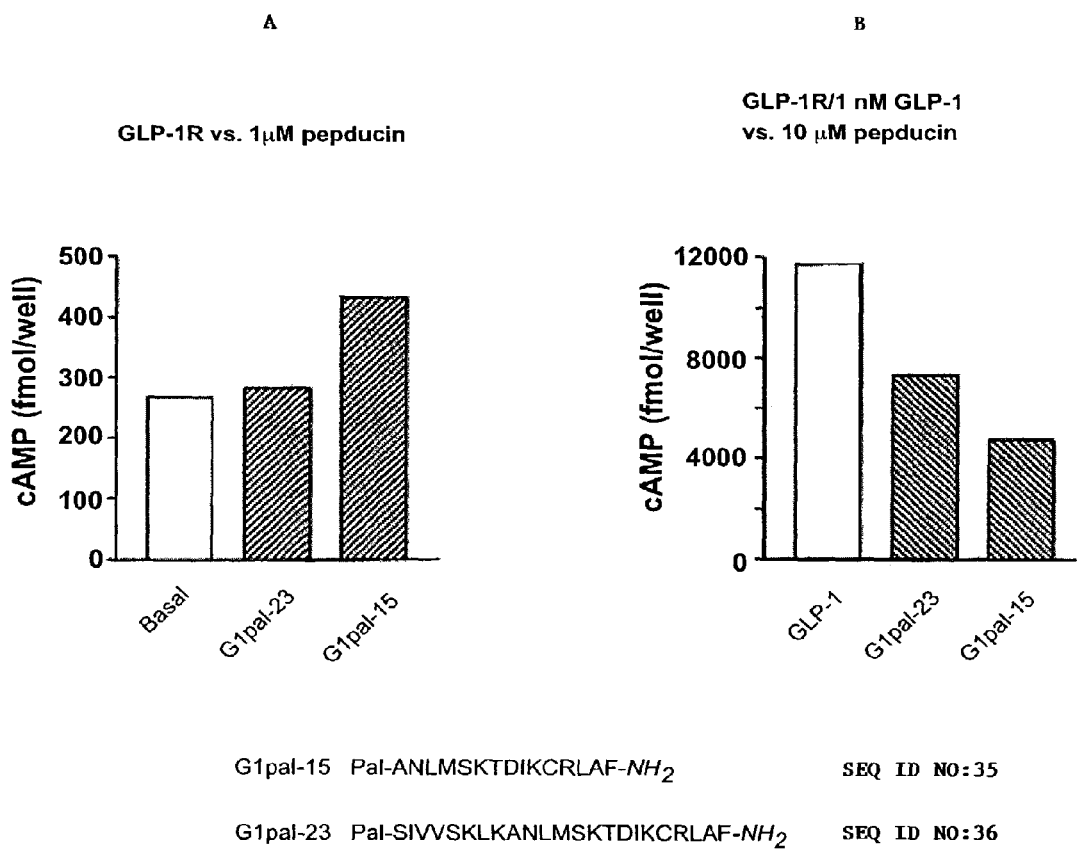
FIGS. 14A and B are bar graphs showing activation and inhibition of glucagon-like peptide-1 receptor (GLP-1R) by GLP-1R-based i3 loop pepducins.

Pepducins based on the i3 loop of glucagon-like peptide receptor-1 (GLP-1R) were generated, and both activated and inhibited this class B GPCR. As shown in FIG. 14 A, 1 μM G1pal-15 pepducin (SEQ ID NO:35) caused 1.7-fold activation of GLP-1R as measured by enhancement of cAMP in Cos7 fibroblasts transiently transfected with human GLP-1R (cAMP accumulation was measured by radioimmunoassay in a 96 well plate). Conversely, at higher concentration (10 μM, FIG. 14 B), both G1pal-23 (SEQ ID NO:36) and G1pal-15 (SEQ ID NO:35) inhibited 40-60% of the activity of GLP-1R in response to its authentic ligand, 1 nM GLP-1 peptide.

Example 16

Figure 15:
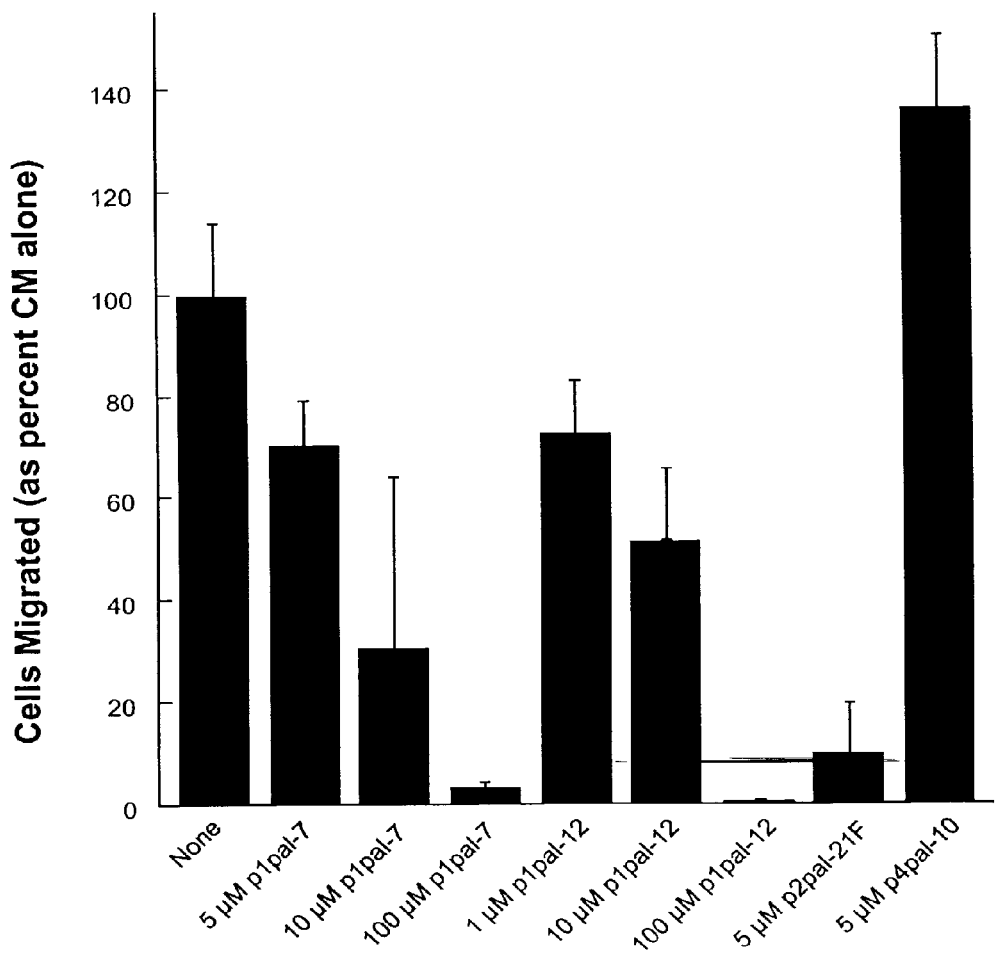
FIG. 15 is a bar graph showing the inhibition of chemoinvasion of MDA-MB-231 breast cancer cells with PAR1 and PAR2-based i3 loop pepducins.

Inhibition of Chemoinvasion of Metastatic Breast Cancer Cells by PAR1 and PAR2-Based Pepducins Recently, PAR1 has been shown to act as a chemokine receptor in inflammatory cells and its expression is tightly correlated with metastatic propensity of breast cancer cells. Experiments were performed in order to determine if application of pepducins based on the i3 loops of PAR1, PAR2, or PAR4 would inhibit migration and invasion of breast cancer cells. It was determined that the highly invasive MDA-MB-231 breast cancer cell line expressed very high levels of functional PAR1, PAR2 and PAR4. As shown in FIG. 15, addition of the PAR1 pepducin antagonist, P1pal-7 (SEQ ID NO:3), inhibited chemoinvasion of MDA-MB-231 cells by 30%. Notably, addition of the PAR2 i3loop pepducin P2pal-21F (SEQ ID NO:8) inhibited 90% of chemoinvasion of the breast cancer cells. In contrast, the anti-PAR4 pepducin, P4pal-10 (SEQ ID NO:29) stimulated chemoinvasion by 40%, suggesting that P4pal-10 has chemokine activity potentially via PAR4. These findings suggest that pepducins targeted towards GPCRs that are expressed in cancer cells could prove beneficial in halting the progression of invasive cancer. Pepducins were added with NIH3T3 Conditioned medium (CM) to the bottom well of a Transwell apparatus.

Example 17

Inhibition of Trypsin Activation of the PAR2 Receptor with an Anti-PAR2 Pepducin PAR2 is rapidly attracting interest from researchers in the field of chronic inflammation. The cellular responses to PAR2 activation are generally pro-inflammatory. Whenever tissues in the body are disturbed an inflammatory response is mounted in order to protect the tissues from potential pathogen entry so that normal healing process can proceed. When inappropriately activated, chronic inflammatory diseases result. For example, in asthma, inappropriate activation occurs in response to a false (non-infectious) airway stimulus, while in chronic obstructive pulmonary disease (COPD), the inappropriate stimulus is cigarette smoke, industrial chemicals, or notably—a genetic defect in α1-antitrypsin. PAR2 is selectively activated by trypsin and trypsin-like enzymes and importantly, PAR2 is expressed ubiquitously by barrier cells of a variety of organs, i.e. epithelia and endothelia. The epithelial expression of PAR2 is particularly striking and leads to the suggestion that PAR2 may be involved in defensive reactions at these barriers. Cells that express PAR2 in the human lung include epithelial cells, airway smooth muscle and fibroblasts, as well as vascular smooth muscle and endothelial cells. PAR2 is also known to be expressed by human mast cells, macrophages and neutrophils, kerotinocytes and myocytes. Moreover, PAR2 is expressed in the epithelia of the small and large intestines, the pancreatic duct, and myenteric neurons where it may participate in a variety of intestinal inflammatory syndromes and in visceral pain. PAR2 is coexpressed with pro-inflammatory neuropeptides substance P (SP) and calcitonin gene-related peptide (CGRP) on sensory nerves, where it mediates neurogenic inflammation. New evidence now links peripheral PAR2 activation to hyperalgesic responses via release of SP in the spinal cord. In summary, therapeutic exploitation of anti-PAR2 compounds might have relevance in the generation of new analgesics, anti-inflammatories, anti-asthmatics and anti-proliferative agents.

Figure 16:
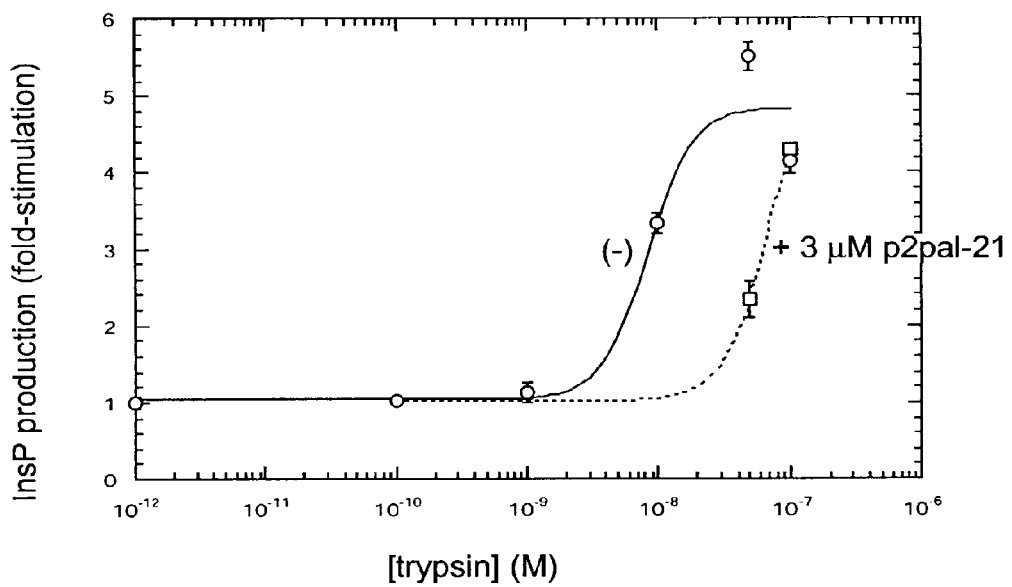
FIG. 16 is a graph showing P2 Pal-21 inhibition of trypsin activation of PAR2.

The ability of the anti-PAR2 pepducin, p2pal-21, was tested for its ability to antagonize one of the authentic protease agonists of PAR2, namely trypsin. As shown in FIG. 16, 3 µM p2pal-21 is able to shift the EC50 of trypsin activation of PAR2 (as measured by InsP production in Cos7 stably expressing PAR2) by 10-fold. Thus, the p2pal-21 pepducin can inhibit both the intramolecularly-activated PAR2 (FIG. 16) and the intermolecularly-activated PAR2 (FIG. 4D).

Example 18

Screening and Detection Methods

The composition of the invention can be used to screen drugs or compounds that modulate GPCR activity or expression as well as to treat disorders characterized by insufficient or excessive production of GPCR protein or production of GPCR protein forms that have decreased or aberrant activity compared to GPCR wild-type protein.

The invention provides a method (also referred to herein as a "screening assay") for identifying modulators, i.e., candidate or test compounds or agents (e.g., peptides, peptidomimetics, small molecules or other drugs) that bind to GPCRs or have a stimulatory or inhibitory effect on, e.g., GPCR protein expression or GPCR activity. The invention also includes compounds identified in the screening assays described herein.

The invention provides assays for screening candidate or test compounds which bind to or modulate the activity of the membrane-bound form of a pepducin-GPCR complex or biologically-active portion thereof. The test compounds of the invention can be obtained using any of the numerous approaches in combinatorial library methods known in the art, including for example, biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. Anticancer Drug Design 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carrell, et al., 1994. Angew. Chem. Int. Ed. Engl. 33: 2061; and Gallop, et al., 1994. J. Med. Chem. 37:1233.

Libraries of compounds may be presented in solution (e.g., Houghten, 1992. Biotechniques 13: 412-421), or on beads (Lam, 1991. Nature 354: 82-84), on chips (Fodor, 1993. Nature 364: 555-556), bacteria (Ladner, U.S. Pat. No. 5,223,409), spores (Ladner, U.S. Pat. No. 5,233,409), plasmids (Cull, et al., 1992. Proc. Natl. Acad. Sci. USA 89: 1865-1869) or on phage (Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; Ladner, U.S. Pat. No. 5,233,409).

An assay is a cell-based assay in which a cell which expresses a membrane-bound form of a GPCR, or a biologically-active portion thereof on the cell surface, plus a pepducin, is contacted with a test compound and the ability of the test compound to bind to the GPCR and displace the pepducin determined. The test compound could bind at the extracellular surface, transmembrane domains, or intracellular surfaces of the GPCR target and inhibit or enhance the pepducin activation of the GPCR. The cell, for example, is of mammalian origin or a yeast cell. Determining the ability of the test compound to displace the pepducin from the GPCR protein can be accomplished, for example, by coupling the pepducin to a radioisotope or enzymatic label such that binding of the test compound displaces the pepducin from the GPCR or biologically-active portion thereof. Alternatively, the test compounds can be labeled with $^{125}$I, $^{35}$S, $^{14}$C, or $^3$H, either directly or indirectly, and the pepducin could displace the radio-labeled test compound from the GPCR and the free radio-labeled test compound detected by direct counting of radioemission or by scintillation counting. Alternatively, test compounds can be enzymatically-labeled with, for example, horseradish peroxidase, alkaline phosphatase, or luciferase, and the enzymatic label detected by increases or decreases in conversion of an appropriate substrate to product upon addition of pepducin.

In another embodiment, an assay is a cell-based assay comprising contacting a cell expressing a membrane-bound form of GPCR protein, or a biologically-active portion thereof, on the cell surface with a test compound and determining the ability of the test compound to modulate (e.g., stimulate or inhibit) the binding, activity of the pepducin for the GPCR As used herein, a "target molecule" is a molecule with which a GPCR protein binds or interacts in nature, for example, a molecule on the surface of a cell which expresses a GPCR interacting protein, a molecule on the surface of a second cell, a molecule in the extracellular milieu, a molecule associated with the internal surface of a cell membrane or a cytoplasmic molecule. A GPCR target molecule can be a non-GPCR molecule or a GPCR peptide of the invention. In one embodiment, a GPCR target molecule is a component of a signal transduction pathway that facilitates transduction of an extracellular signal (e.g. a signal generated by binding of a compound to a membrane-bound GPCR) through the cell membrane and into the cell. The target, for example, can be a second intercellular protein that has catalytic activity or a protein that facilitates the association of downstream signaling molecules with GPCR.

Determining the ability of the test molecule to interact with a GPCR target molecule can be accomplished by one of the methods described above for determining direct binding. In one embodiment, determining the ability of the test molecule to inhibit the GPCR peptide interaction with a GPCR target molecule can be accomplished by determining the activity of the target GPCR-pepducin complex. For example, the activity of the target molecule can be determined by inhibiting GPCR-peptide induction of a cellular second messenger of the GPCR target (i.e. intracellular $Ca^{2+}$, diacylglycerol, $IP_3$, etc.), detecting catalytic/enzymatic activity dependent on GPCR activation or inhibition, detecting the induction or inhibition of a reporter gene (comprising a GPCR-responsive regulatory element operatively linked to a nucleic acid encoding a detectable marker, e.g., luciferase), or detecting a cellular response, for example, cell survival, cellular differentiation, or cell proliferation.

Alternatively, an assay of the invention is a cell-free assay comprising contacting a GPCR peptide or biologically-active portion thereof with a test compound and determining the ability of the test compound to bind or modulate (e.g. stimulate or inhibit) the activity of the GPCR protein or biologically-active portion thereof.

Binding of the test compound to the GPCR can be determined either directly or indirectly as described above. For example, the assay comprises contacting the pepducin plus the GPCR or biologically-active portion thereof with a known compound which binds GPCR to form an assay mixture, contacting the assay mixture with a test compound, and determining the ability of the test compound to interact with a GPCR protein, wherein determining the ability of the test compound to interact with a GPCR protein comprises determining the ability of the test compound to preferentially bind to GPCR or biologically-active portion thereof as compared to the known compound.

Determining the ability of the test compound to modulate the activity of GPCR can be accomplished, for example, by determining the ability of the GPCR peptide to bind to a GPCR target molecule by one of the methods described above for determining direct binding.

Alternatively, determining the ability of the test compound to modulate the activity of GPCR peptide can be accomplished by determining the ability of the GPCR peptide to further modulate a GPCR target molecule. For example, the catalytic/enzymatic activity of the target molecule on an appropriate substrate can be determined as described above.

The cell-free assay comprises contacting the GPCR peptide or biologically-active portion thereof with a known compound which binds the GPCR to form an assay mixture, contacting the assay mixture with a test compound, and determining the ability of the test compound to interact with a GPCR, wherein determining the ability of the test compound to interact with a GPCR comprises determining the ability of the GPCR peptide to preferentially bind to or modulate the activity of a GPCR target molecule.

The cell-free assays of the invention are amenable to use of both the soluble form or the membrane-bound form of GPCR protein. In the case of cell-free assays comprising the membrane-bound form of GPCR protein, it may be desirable to utilize a solubilizing agent such that the membrane-bound form of GPCR protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

It may be desirable to immobilize either GPCR peptide or its target molecule to facilitate separation of complexed from uncomplexed forms of one or both of the proteins, as well as to accommodate automation of the assay. Binding of a test compound to GPCR protein, or interaction of GPCR protein with a pepducin in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-GPCR fusion peptides or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or GPCR peptide, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, vide supra. Alternatively, the complexes can be dissociated from the matrix, and the level of GPCR peptide binding or activity determined using standard techniques.

Other techniques for immobilizing proteins on matrices are also used in the screening assays of the invention. For example, either the GPCR peptide or its target molecule can be immobilized utilizing conjugation of biotin and streptavidin. Biotinylated GPCR peptide or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with GPCR peptide or target molecules, but which do not interfere with binding of the GPCR peptide to its cognate GPCR, can be derivatized to the wells of the plate, and unbound target or GPCR peptide trapped in the wells by antibody conjugation. Methods for detecting such complexes, in addition to those described above for the GST-immobilized complexes, include immunodetection of complexes using antibodies reactive with the GPCR peptide or target molecule, as well as enzyme-linked assays that rely on detecting an enzymatic activity associated with the GPCR peptide or target molecule.

Modulators of GPCR protein expression are identified in a method wherein a cell is contacted with a candidate compound and the expression of GPCR mRNA or protein in the cell is determined. The level of expression of GPCR mRNA or protein in the presence of the candidate compound is compared to the level of expression of GPCR mRNA or protein in the absence of the candidate compound. The candidate compound can then be identified as a modulator of GPCR mRNA or protein expression based upon this comparison. For example, when expression of GPCR mRNA or protein is greater (i.e., statistically significantly greater) in the presence of the candidate compound than in its absence, the candidate compound is identified as a stimulator of GPCR mRNA or protein expression. Alternatively, when expression of GPCR mRNA or protein is less (statistically significantly less) in the presence of the candidate compound than in its absence, the candidate compound is identified as an inhibitor of GPCR mRNA or protein expression. The level of GPCR mRNA or protein expression in the cells can be determined by methods described herein for detecting GPCR mRNA or protein.

The peptide sequences discussed herein are presented in Table 3.

TABLE 3

SEQUENCES

| SEQ ID NO: | SEQUENCE | Name/Identifier |
|---|---|---|
| 1 | RCLSSSAVANRSKKSRALF | P1Pal19 |
| 2 | AVANRSKKSRALF | P1Pal13 |
| 3 | KKSRALF | P1Pal7 |
| 4 | RCLSSSAVANRS | P1Pal12 |
| 5 | RCLSSSAVANQSQQSQALF | P1Pal19Q |
| 6 | RCESSSAEANRSKKERELF | P1Pal19E |
| 7 | RMLRSSAMDENSEKKRKRAIK | P2Pal21 |
| 8 | RMLRSSAMDENSEKKRKRAIF | P2Pal21F |
| 9 | HTLAASGRRYGHALR | P4Pal15 |
| 10 | HTLAASGRRYGHALF | P4Pal15F |
| 11 | KVKSSGIRVGSSKRKKSEKKVTK | S2Pal23 |
| 12 | KVRSSGIRVGSSKRKKSEKKVTF | S2Pal23F |
| 13 | RIRSNSSAANLMAKKRVIR | APal19 |
| 14 | RIRSNSSAANLMAKKRVIEF | APal19F |
| 15 | SGSRPTQAKLLAKKRVVR | BPal18 |
| 16 | SGSRPTQAKLLAKKRVVF | BPal18F |
| 17 | SLIGKV | PAR2 Extracellular Agonist |
| 18 | AGCKNFFWKTFTSC | Somatostatin Receptor Extracellular Agonist |
| 19 | RELYLGLRFDGDSDSQSRVRNQGGLPGAVHQNGRCRPETGAVGEDSDGCYVQLPRSRPALELTALTAPGPGSGSRPTQAKLLAKKRVVR | CCKB i3 loop |
| 20 | LELYQGIKFEASQKKSAKERKPSTTSSGKYEDSDGCYLKTRPPRKLELRQLSTGSSSRANRIRSNSSAANLMAKKRVIR | CCKA i3 loop |
| 21 | ITLWASEIPGDSSDRYHEQVSAKRKVVK | SubP i3 loop |

TABLE 3-continued

SEQUENCES

| SEQ ID NO: | SEQUENCE | Name/Identifier |
|---|---|---|
| 22 | KVKSSGIRVGSSKRKKSEKKVTR | SSTR2 i3 loop |
| 23 | SFLLRN | PAR 1 Extracellular Ligand |
| 24 | INLKALAALAKKIL | Mastoparan (wasp venom peptide) |
| 25 | RPKPQQFFGLM | SubP agonist |
| 26 | AYPGKF | PAR4 Agonist |
| 27 | PAFISEDASGYLC | LBS-1 |
| 28 | TGAIRQGANMKGAI | MC4pal-14 |
| 29 | SGRRYGHALR | P4Pal10 |
| 30 | RALAANGQRYSHALR | murine PAR4 i3 loop |
| 31 | PAFIS | fragment for LBS-1 |
| 32 | EDASGYLC | modified fragment for LBS-1 |
| 33 | YVRTRGVGKVPRKKVNVF | Y12pal-18 |
| 34 | KELYRS YVRTRGVGKVPRKKVNVF | Y12pal-24 |
| 35 | ANLMSKTDIKCRLAF | G1pal-15 |
| 36 | SIVVSKLKANLMSKTDIKCRLAF | G1pal-23 |
| 37 | EDASGYLT | WT fragment for LBS-1 |
| 38 | MEGISIYTSDNYTEEMGSGDYDSMKEPCFREENANFNKIFLPTIYSIIFLTGIVGNGLVILVMGYQKKLRSMTDKYRLHLSVADLLFVITLPFWAVDAVANWYFGNFLCKAVHVIYTVNLYSSVLILAFISLDRYLAIVHATNSQRPRKLLAEKVVYVGVWIPALLLTIPDFIFANVSEADDRYICDRFYPNDLWVVVFQFQHIMVGLILPGIVILSCYCIIISKLSHSKGHQKRKALKTTVILILAFFACWLPYYIGISIDSFILLEIIKQGCEFENTVHKWISITEALAFFHCCLNPILYAFLGAKFKTSAQHALTSVSRGSSLKILSKGKRGGHSSVSTESESSSFHSS | CXCR4 |
| 39 | IFLPTIYSIIFLTGIVGNGLVILV | TM1 of CXCR4 |
| 40 | VCYVSIIRSLSSSAVANRSKKSRALF | P1-i3-26 |
| 41 | RALF | Transmembrane domain of P1pal7 |
| 42 | LDPRSFLLRN | PAR1 Thrombin cleavage site |
| 43 | FSAVFFFVPLIISTVCYVSIIRCLSSSAVANRSKKSRALF | P1-i3-40 |
| 44 | VPLIISTVCYVSIIRCLSSSAVANRSKKSRALF | P1-i3-33 |
| 45 | RSLSSSAVANRSKKSRALF | P1-i3-19 |
| 46 | FSAFSAVFFFVPLIISTVCYVSIIRCLSSSAVANRSKKSRALF | TM5-i3-TM6 |
| 47 | Pal-RCLSSSAVANRSKKSRALF | P1pal19 (N-palmitate modified) |
| 48 | Pal-AVANRSKKSRALF | P1pal13 (N-palmitate modified) |
| 49 | Pal-KKSRALF | P1pal (N-palmitate modified) |
| 50 | Pal-RCLSSSAVANRS | P1pal12 (N-palmitate modified) |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The instant application contains a Sequence Listing which has been submitted in ASCII format via EFS-Web and is hereby incorporated by reference in its entirety. Said ASCII copy, created on Sep. 25, 2012, is named 086432-0022-sequence listing.txt and is 19,277 bytes in size.

What is claimed is:

1. A method of treating a cardiovascular disorder in a mammal, comprising administering to a mammal in need thereof in an amount sufficient to reduce the severity of the disorder a polypeptide comprising:
   a) a first domain comprising a third intracellular loop, or a fragment thereof of a Protease-Activated Receptor (PAR); and
   b) a second domain, attached to the first domain, wherein the second domain comprises a cell-penetrating, membrane-tethering moiety comprising: a lipid, a cholesterol, a phospholipid, a steroid, a sphingosine, a ceramide, an octyl-glycine, a 2-cyclohexylalanine, or a benzolylphenylalanine;
   wherein the polypeptide is a PAR antagonist,
   wherein the first domain does not comprise an extracellular portion of the PAR, and
   wherein the first domain comprises at least 3 contiguous amino acid residues of the third intracellular loop.

2. The method of claim 1, wherein the cardiovascular disorder is selected from the group consisting of arterial thrombosis, atherosclerosis and restenosis.

3. The method of claim 1 or 2, wherein the PAR is Protease-Activated Receptor 1 (PAR-1) or PAR-4.

4. The method of claim 3, wherein the PAR antagonist comprises SEQ ID NO: 3 or SEQ ID NO: 4.

5. The method of claim 3, wherein the PAR antagonist comprises SEQ ID NO: 29.

6. The method of claim 1, wherein the second domain comprises a palmitoyl group, a myristoyl group, or a pentadecanoyl group.

7. The method of claim 1, wherein the second domain comprises a lipid.

8. The method of claim 1, wherein the polypeptide is infused into a vascular lumen.

9. The method of claim 8, wherein the vascular lumen is the lumen of a jugular or peripheral vein.

10. The method of claim 1, wherein the polypeptide is infused into a perivascular space.

11. The method of claim 1, wherein the polypeptide is administered transdermally, subdermally, or subcutaneously.

12. The method of claim 1, wherein the polypeptide is administered into the lung tissue of said mammal.

13. The method of claim 1, wherein said mammal is human.

14. The method of claim 1, wherein said PAR antagonist comprises an amino acid sequence selected from the group consisting of: SEQ ID NO: 3, SEQ ID NO: 4, SEQ ID NO: 9, and SEQ ID NO: 10.

15. The method of claim 1, wherein the second domain comprises a cholesterol.

16. The method of claim 1, wherein PAR antagonist is P1pal-7.

17. A method of treating atherosclerosis in a mammal, comprising administering to a mammal in need thereof in an amount sufficient to reduce the severity of atherosclerosis a polypeptide comprising:
   a) a first domain comprising a third intracellular loop, or a fragment thereof of a Protease-Activated Receptor (PAR); and
   b) a second domain, attached to the first domain, wherein the second domain comprises a cell-penetrating, membrane-tethering moiety comprising: a lipid, a cholesterol, a phospholipid, a steroid, a sphingosine, a ceramide, an octyl-glycine, a 2-cyclohexylalanine, or a benzolylphenylalanine;
   wherein said polypeptide is a PAR antagonist,
   wherein the first domain does not comprise an extracellular portion of the PAR, and
   wherein the first domain comprises at least 3 contiguous amino acid residues of the third intracellular loop.

18. The method of claim 17, wherein the PAR is PAR-1 or PAR-4.

19. The method of claim 18, wherein the PAR antagonist comprises SEQ ID NO: 3 or SEQ ID NO: 4.

20. The method of claim 18, wherein the PAR antagonist comprises SEQ ID NO: 29.

21. The method of claim 17, wherein the second domain comprises a palmitoyl group, a myristoyl group, or a pentadecanoyl group.

22. The method of claim 21, wherein the polypeptide is P1pal-7.

23. The method of claim 17, wherein the second domain comprises a lipid.

24. The method of claim 17, wherein said polypeptide is infused into a vascular lumen.

25. The method of claim 24, wherein the vascular lumen is the lumen of a jugular or peripheral vein.

26. The method of claim 17, wherein the polypeptide is infused into a perivascular space.

27. The method of claim 17, wherein the polypeptide is administered transdermally, subdermally, or subcutaneously.

28. The method of claim 17, wherein the polypeptide is administered into the lung tissue of said mammal.

29. The method of claim 17, wherein said mammal is human.

30. The method of claim 17, wherein the second domain comprises a cholesterol.

* * * * *

```
                          SEQUENCE LISTING

<160> NUMBER OF SEQ ID NOS: 50

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Cys Leu Ser Ser Ser Ala Val Ala Asn Arg Ser Lys Lys Ser Arg
1               5                   10                  15

Ala Leu Phe

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Val Ala Asn Arg Ser Lys Lys Ser Arg Ala Leu Phe
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Lys Ser Arg Ala Leu Phe
1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Cys Leu Ser Ser Ser Ala Val Ala Asn Arg Ser
1               5                   10

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
```

```
                        peptide

<400> SEQUENCE: 5

Arg Cys Leu Ser Ser Ser Ala Val Ala Asn Gln Ser Gln Gln Ser Gln
1               5                  10                  15

Ala Leu Phe

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Cys Glu Ser Ser Ser Ala Glu Ala Asn Arg Ser Lys Lys Glu Arg
1               5                  10                  15

Glu Leu Phe

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Met Leu Arg Ser Ser Ala Met Asp Glu Asn Ser Glu Lys Lys Arg
1               5                  10                  15

Lys Arg Ala Ile Lys
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Met Leu Arg Ser Ser Ala Met Asp Glu Asn Ser Glu Lys Lys Arg
1               5                  10                  15

Lys Arg Ala Ile Phe
            20

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Thr Leu Ala Ala Ser Gly Arg Arg Tyr Gly His Ala Leu Arg
1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
                                  peptide

<400> SEQUENCE: 10

His Thr Leu Ala Ala Ser Gly Arg Arg Tyr Gly His Ala Leu Phe
1               5                   10                  15

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Val Lys Ser Ser Gly Ile Arg Val Gly Ser Ser Lys Arg Lys Lys
1               5                   10                  15

Ser Glu Lys Lys Val Thr Lys
            20

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Val Arg Ser Ser Gly Ile Arg Val Gly Ser Ser Lys Arg Lys Lys
1               5                   10                  15

Ser Glu Lys Lys Val Thr Phe
            20

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ile Arg Ser Asn Ser Ser Ala Ala Asn Leu Met Ala Lys Lys Arg
1               5                   10                  15

Val Ile Arg

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ile Arg Ser Asn Ser Ser Ala Ala Asn Leu Met Ala Lys Lys Arg
1               5                   10                  15

Val Ile Glu Phe
            20

<210> SEQ ID NO 15
<211> LENGTH: 18
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 15

Ser Gly Ser Arg Pro Thr Gln Ala Lys Leu Leu Ala Lys Lys Arg Val
1               5                   10                  15

Val Arg

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gly Ser Arg Pro Thr Gln Ala Lys Leu Leu Ala Lys Lys Arg Val
1               5                   10                  15

Val Phe

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Leu Ile Gly Lys Val
1               5

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Gly Cys Lys Asn Phe Phe Trp Lys Thr Phe Thr Ser Cys
1               5                   10

<210> SEQ ID NO 19
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Arg Glu Leu Tyr Leu Gly Leu Arg Phe Asp Gly Asp Ser Asp Ser Asp
1               5                   10                  15

Ser Gln Ser Arg Val Arg Asn Gln Gly Gly Leu Pro Gly Ala Val His
            20                  25                  30

Gln Asn Gly Arg Cys Arg Pro Glu Thr Gly Ala Val Gly Glu Asp Ser
        35                  40                  45

Asp Gly Cys Tyr Val Gln Leu Pro Arg Ser Arg Pro Ala Leu Glu Leu
    50                  55                  60

Thr Ala Leu Thr Ala Pro Gly Pro Gly Ser Gly Ser Arg Pro Thr Gln
65                  70                  75                  80

```
Ala Lys Leu Leu Ala Lys Lys Arg Val Val Arg
            85                  90
```

<210> SEQ ID NO 20
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Leu Glu Leu Tyr Gln Gly Ile Lys Phe Glu Ala Ser Gln Lys Lys Ser
1               5                   10                  15

Ala Lys Glu Arg Lys Pro Ser Thr Thr Ser Ser Gly Lys Tyr Glu Asp
            20                  25                  30

Ser Asp Gly Cys Tyr Leu Gln Lys Thr Arg Pro Pro Arg Lys Leu Glu
        35                  40                  45

Leu Arg Gln Leu Ser Thr Gly Ser Ser Ser Arg Ala Asn Arg Ile Arg
    50                  55                  60

Ser Asn Ser Ser Ala Ala Asn Leu Met Ala Lys Lys Arg Val Ile Arg
65                  70                  75                  80
```

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Ile Thr Leu Trp Ala Ser Glu Ile Pro Gly Asp Ser Ser Asp Arg Tyr
1               5                   10                  15

His Glu Gln Val Ser Ala Lys Arg Lys Val Val Lys
            20                  25
```

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Lys Val Lys Ser Ser Gly Ile Arg Val Gly Ser Ser Lys Arg Lys Lys
1               5                   10                  15

Ser Glu Lys Lys Val Thr Arg
            20
```

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Ser Phe Leu Leu Arg Asn
1               5
```

<210> SEQ ID NO 24
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Asn Leu Lys Ala Leu Ala Ala Leu Ala Lys Lys Ile Leu
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Pro Lys Pro Gln Gln Phe Phe Gly Leu Met
1               5                   10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Tyr Pro Gly Lys Phe
1               5

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Ala Phe Ile Ser Glu Asp Ala Ser Gly Tyr Leu Cys
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Gly Ala Ile Arg Gln Gly Ala Asn Met Lys Gly Ala Ile
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gly Arg Arg Tyr Gly His Ala Leu Arg
1               5                   10
```

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ala Leu Ala Ala Asn Gly Gln Arg Tyr Ser His Ala Leu Arg
1               5                   10                  15

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Ala Phe Ile Ser
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Glu Asp Ala Ser Gly Tyr Leu Cys
1               5

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Val Arg Thr Arg Gly Val Gly Lys Val Pro Arg Lys Lys Val Asn
1               5                   10                  15

Val Phe

<210> SEQ ID NO 34
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Glu Leu Tyr Arg Ser Tyr Val Arg Thr Arg Gly Val Gly Lys Val
1               5                   10                  15

Pro Arg Lys Lys Val Asn Val Phe
            20

<210> SEQ ID NO 35
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 35

Ala Asn Leu Met Ser Lys Thr Asp Ile Lys Cys Arg Leu Ala Phe
1               5                   10                  15

<210> SEQ ID NO 36
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Ile Val Val Ser Lys Leu Lys Ala Asn Leu Met Ser Lys Thr Asp
1               5                   10                  15

Ile Lys Cys Arg Leu Ala Phe
            20

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Asp Ala Ser Gly Tyr Leu Thr
1               5

<210> SEQ ID NO 38
<211> LENGTH: 352
<212> TYPE: PRT
<213> ORGANISM: Homo sapiens

<400> SEQUENCE: 38

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
        50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
        130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
```

```
                    165                 170                 175
Val Ser Glu Ala Asp Asp Arg Tyr Ile Cys Asp Arg Phe Tyr Pro Asn
            180                 185                 190

Asp Leu Trp Val Val Phe Gln Phe Gln His Ile Met Val Gly Leu
        195                 200                 205

Ile Leu Pro Gly Ile Val Ile Leu Ser Cys Tyr Cys Ile Ile Ser
        210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
            275                 280                 285

Ala Leu Ala Phe Phe His Cys Cys Leu Asn Pro Ile Leu Tyr Ala Phe
        290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 39
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Phe Leu Pro Thr Ile Tyr Ser Ile Ile Phe Leu Thr Gly Ile Val
1               5                   10                  15

Gly Asn Gly Leu Val Ile Leu Val
            20

<210> SEQ ID NO 40
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Cys Tyr Val Ser Ile Ile Arg Ser Leu Ser Ser Ser Ala Val Ala
1               5                   10                  15

Asn Arg Ser Lys Lys Ser Arg Ala Leu Phe
            20                  25

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41
```

```
Arg Ala Leu Phe
 1

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      PAR1 thrombin cleavage site

<400> SEQUENCE: 42

Leu Asp Pro Arg Ser Phe Leu Leu Arg Asn
 1               5                  10

<210> SEQ ID NO 43
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Phe Ser Ala Val Phe Phe Val Pro Leu Ile Ile Ser Thr Val Cys
 1               5                  10                  15

Tyr Val Ser Ile Ile Arg Cys Leu Ser Ser Ser Ala Val Ala Asn Arg
                20                  25                  30

Ser Lys Lys Ser Arg Ala Leu Phe
            35                  40

<210> SEQ ID NO 44
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Val Pro Leu Ile Ile Ser Thr Val Cys Tyr Val Ser Ile Ile Arg Cys
 1               5                  10                  15

Leu Ser Ser Ser Ala Val Ala Asn Arg Ser Lys Lys Ser Arg Ala Leu
                20                  25                  30

Phe

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ser Leu Ser Ser Ser Ala Val Ala Asn Arg Ser Lys Lys Ser Arg
 1               5                  10                  15

Ala Leu Phe

<210> SEQ ID NO 46
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 46

Phe Ser Ala Phe Ser Ala Val Phe Phe Phe Val Pro Leu Ile Ile Ser
1               5                   10                  15

Thr Val Cys Tyr Val Ser Ile Ile Arg Cys Leu Ser Ser Ala Val
            20                  25                  30

Ala Asn Arg Ser Lys Lys Ser Arg Ala Leu Phe
        35                  40

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term palmitate

<400> SEQUENCE: 47

Arg Cys Leu Ser Ser Ser Ala Val Ala Asn Arg Ser Lys Lys Ser Arg
1               5                   10                  15

Ala Leu Phe

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term palmitate

<400> SEQUENCE: 48

Ala Val Ala Asn Arg Ser Lys Lys Ser Arg Ala Leu Phe
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term palmitate

<400> SEQUENCE: 49

Lys Lys Ser Arg Ala Leu Phe
1               5

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term palmitate

<400> SEQUENCE: 50

Arg Cys Leu Ser Ser Ser Ala Val Ala Asn Arg Ser
1               5                   10